United States Patent
Klaenhammer et al.

(10) Patent No.: US 9,340,792 B2
(45) Date of Patent: May 17, 2016

(54) RECOMBINANT LACTOBACILLUS WITH DECREASED LIPOTEICHOIC ACID TO REDUCE INFLAMMATORY RESPONSES

(75) Inventors: Todd R. Klaenhammer, Raleigh, NC (US); Erika Pfeiler, Greeneville, TN (US); Mansour Mohamadzadeh, Gainesville, FL (US)

(73) Assignees: North Carolina State University, Raleigh, NC (US); Northwestern University, Evanston, IL (US)

( * ) Notice: Subject to any disclaimer, the term of this patent is extended or adjusted under 35 U.S.C. 154(b) by 0 days.

(21) Appl. No.: 13/805,037

(22) PCT Filed: Jun. 16, 2011

(86) PCT No.: PCT/US2011/040674
§ 371 (c)(1),
(2), (4) Date: May 10, 2013

(87) PCT Pub. No.: WO2011/159880
PCT Pub. Date: Dec. 22, 2011

(65) Prior Publication Data
US 2013/0224153 A1    Aug. 29, 2013

Related U.S. Application Data

(60) Provisional application No. 61/356,165, filed on Jun. 18, 2010, provisional application No. 61/433,598, filed on Jan. 18, 2011.

(51) Int. Cl.
| | |
|---|---|
| *C12N 15/74* | (2006.01) |
| *A61K 35/744* | (2015.01) |
| *C12N 1/20* | (2006.01) |
| *C12N 9/12* | (2006.01) |
| *C12R 1/23* | (2006.01) |
| *A61K 35/00* | (2006.01) |

(52) U.S. Cl.
CPC ............ *C12N 15/746* (2013.01); *A61K 35/744* (2013.01); *C12N 1/20* (2013.01); *C12N 9/1288* (2013.01); *C12R 1/23* (2013.01); *A61K 2035/115* (2013.01)

(58) Field of Classification Search
None
See application file for complete search history.

(56) References Cited

PUBLICATIONS

Azcarate-Peril et al., J Dairy Science, 2009, 92(3)870-886.*
Vos et al. 2009; ISME Journal 3:199-208.*

Altermann, E., et al., "Complete genome sequence of the probiotic lactic acid bacterium *Lactobacillus acidophilus* NCFM," *PNAS*, 2005, vol. 102(11), pp. 3906-3912.
Claes, I., et al., "Impact of lipoteichoic acid modification on the performance of the probiotic *Lactobacillus rhamnosus* GG in experimental colitis," *Clinical and Experimental Immunology*, 2010, vol. 162(2), pp. 306-314.
Duncker, S., et al., "The D-alanine content of lipoteichoic acid is crucial for *Lactobacillus plantarum*-mediated protection from visceral pain perception in a rat colorectal distention model," *Neurogastroenterol Motil*, 2008, vol. 20(7), pp. 843-850.
Fedtke, I., et al., "A *Staphylococcus aureus ypfP* mutant with strongly reduced lipoteichoic acid (LTA) content: LTA governs bacterial surface properties and autolysin activity," *Molecular Microbiology*, 2007, vol. 65(4), pp. 1078-1091.
Grangette, C., et al., "Enhanced anti-inflammatory capacity of a *Lactobacillus plantarum* mutant synthesizing modified teichoic acids," *PNAS*, 2005, vol. 102(29), pp. 10321-10326.
Gründling, A., et al., "Synthesis of glycerol phosphate lipoteichoic acid in *Staphylococcus aureus*," *PNAS*, 2007, vol. 104(20), pp. 8478-8483.
Harrington, D., et al., "Multiple Changes in Cell Wall Antigens of Isogenic Mutants of *Streptococcus mutans*," *Journal of Bacteriology*, 1993, vol. 175(18), pp. 5925-5933.
Hirose, Y, et al., "Lipoteichoic acids on *Lactobacillus plantarum* cell surfaces correlate with induction of interleukin-12p40 production," *Microbiol Immunol*, 2010, vol. 54(3), pp. 143-151.
Mohamadzadeh, M., et al., "Regulation of induced colonic inflammation by *Lactobacillus acidophilus* deficient in lipoteichoic acid," *PNAS*, 2011, vol. 108(Supp 1), pp. 4623-4630.
Oku, Y., et al., "Pleiotropic Roles of Polyglycerolphosphate Synthase of Lipoteichoic Acid in Growth of *Staphylococcus aureus* Cells," *Journal of Bacteriology*, 2009, vol. 191(1), pp. 141-151.
Saber, R., et al., "Lipoteichoic acid-deficient *Lactobacillus acidophilus* regulates downstream signals," *Immunotherapy*, 2011, vol. 3(3), pp. 337-347.

* cited by examiner

*Primary Examiner* — Doug Schultz
(74) *Attorney, Agent, or Firm* — Womble Carlyle Sandridge & Rice LLP

(57) ABSTRACT

Methods and compositions for treating or preventing inflammatory disorders are provided. The compositions of the invention comprise a recombinant bacterium genetically modified to decrease the display of lipoteichoic acid on the cell surface. Methods of the invention comprise administering to a subject a recombinant bacterium modified to decrease the display of lipoteichoic acid on the cell surface. Administration of the recombinant bacterium promotes a desired therapeutic response. The recombinant bacterium may be administered in a single dose or series of doses. Methods of the invention find use in treating or preventing a variety of inflammatory disorders including, for example, treating or preventing inflammatory bowel disease, colitis, or Crohn's disease.

17 Claims, 23 Drawing Sheets

Figure 7A

| | Distal | | | Proximal | | |
|---|---|---|---|---|---|---|
| | DSS | NCK56 | NCK2025 | DSS | NCK56 | NCK2025 |
| Immune Regulatory | | | | | | |
| Ccl3 | 13.99 | 46.26 | 8.09 | 2.72 | 17.83 | 1.96 |
| Ccl5 | 14.44 | 67.45 | 10.64 | 2.14 | 13.43 | 3.75 |
| Ccl7 | 24.43 | 107.23 | 22.97 | 3.97 | 16.95 | 2.09 |
| Ccr1 | 10.14 | 27.50 | 5.74 | 4.05 | 5.56 | 1.21 |
| Ccr6 | 7.15 | 25.51 | 6.08 | 3.50 | 8.71 | 2.07 |
| Cx3cr1 | 1.17 | 0.99 | 1.41 | 4.72 | 2.55 | 2.78 |
| Cxcr4 | 1.13 | 1.55 | 1.47 | 1.58 | 1.53 | 1.01 |
| Il13 | 1.28 | 1.31 | 1.48 | 2.01 | 1.69 | 1.43 |
| Il3 | 0.91 | 1.06 | 1.08 | 2.76 | 2.17 | 2.24 |
| Pla2g7 | 3.23 | 10.42 | 5.50 | 3.29 | 4.83 | 2.12 |
| Plaa | 1.07 | 1.76 | 2.41 | 1.12 | 1.24 | 0.96 |
| Srf | 0.97 | 1.41 | 1.78 | 1.16 | 1.11 | 1.10 |
| Tgfb1 | 2.23 | 4.49 | 2.62 | 2.05 | 2.77 | 1.50 |
| Signaling | | | | | | |
| Jak2 | 0.79 | 0.96 | 0.95 | 1.02 | 0.88 | 1.07 |
| Map2k4 | 1.09 | 1.03 | 1.36 | 1.06 | 1.20 | 0.86 |
| Map3k1 | 1.07 | 0.93 | 1.08 | 1.09 | 1.31 | 1.01 |
| Mapk9 | 0.72 | 0.63 | 1.06 | 1.32 | 1.22 | 0.93 |
| Pak1 | 0.70 | 0.61 | 1.33 | 1.34 | 1.23 | 1.05 |
| Ptprc/CD45 | 6.59 | 13.72 | 4.44 | 1.95 | 2.84 | 1.64 |
| Raf1 | 0.99 | 1.38 | 1.79 | 1.21 | 1.28 | 1.04 |
| Socs2 | 0.74 | 1.40 | 1.11 | 1.84 | 1.20 | 1.40 |
| Sp1 | 1.01 | 1.65 | 1.46 | 1.38 | 1.24 | 1.51 |
| Stat6 | 1.06 | 1.47 | 1.95 | 1.88 | 1.49 | 1.25 |
| Timp1 | 23.09 | 56.33 | 27.02 | 4.74 | 20.73 | 1.78 |
| Tyk2 | 0.91 | 1.42 | 1.91 | 1.55 | 1.63 | 1.16 |
| Immune Stimulatory | | | | | | |
| Ccl11 | 4.17 | 10.87 | 3.31 | 2.79 | 6.54 | 1.76 |
| Ccl2 | 28.59 | 125.23 | 23.96 | 3.15 | 14.98 | 1.53 |
| Ccr7 | 2.19 | 4.64 | 2.58 | 2.32 | 2.53 | 1.19 |
| Cd40 | 3.83 | 17.92 | 4.11 | 2.49 | 4.09 | 1.61 |
| Cd69 | 4.36 | 13.18 | 1.63 | 3.18 | 2.40 | 0.65 |
| Cd80 | 3.06 | 4.60 | 3.03 | 4.41 | 2.38 | 1.18 |
| Cd86 | 3.49 | 6.26 | 2.70 | 3.08 | 2.66 | 1.65 |
| Il15 | 0.65 | 0.61 | 0.73 | 1.66 | 0.83 | 1.06 |
| Il1b | 66.69 | 146.65 | 33.46 | 4.93 | 44.98 | 2.17 |
| Il23a | 0.80 | 0.68 | 0.79 | 2.34 | 2.16 | 1.46 |
| Il6 | 7.87 | 28.37 | 9.26 | 2.11 | 12.61 | 0.34 |
| Irf3 | 0.92 | 0.66 | 1.08 | 1.17 | 1.23 | 0.98 |
| Mal | 0.90 | 1.45 | 4.16 | 0.57 | 0.57 | 1.09 |
| Nfkb1 | 1.60 | 1.62 | 1.46 | 0.83 | 1.15 | 0.86 |
| Nfkbib | 1.03 | 1.62 | 1.73 | 2.92 | 1.54 | 1.38 |
| Nos2 | 5.49 | 21.95 | 5.72 | 2.23 | 3.89 | 1.41 |
| P2rx7 | 0.86 | 0.86 | 1.32 | 3.67 | 1.27 | 0.98 |
| Stat1 | 5.19 | 17.39 | 3.77 | 1.62 | 3.15 | 1.42 |
| Stat4 | 3.65 | 7.27 | 3.40 | 2.87 | 3.57 | 2.17 |
| Tnf | 3.46 | 9.28 | 3.37 | 1.36 | 3.80 | 1.36 |
| Tnfrsf11a | 0.89 | 1.26 | 1.70 | 2.01 | 1.76 | 1.78 |
| Tnfrsf7 | 0.88 | 1.79 | 1.79 | 3.57 | 3.35 | 2.15 |
| Tnfrsf8 | 1.05 | 1.46 | 1.71 | 2.36 | 0.93 | 0.71 |
| Tnfsf11 | 3.42 | 11.64 | 3.54 | 2.71 | 2.08 | 0.54 |
| Traf1 | 1.57 | 3.37 | 2.14 | 1.40 | 2.73 | 2.07 |
| Traf2 | 1.16 | 1.71 | 2.25 | 1.03 | 1.50 | 1.10 |
| Traf3 | 1.31 | 2.14 | 1.99 | 1.38 | 1.51 | 1.18 |
| Traf6 | 1.10 | 2.38 | 2.62 | 1.44 | 1.47 | 0.86 |
| Proliferation/Apoptosis/Angiogenesis/Adhesion | | | | | | |
| Csf1 | 1.37 | 2.05 | 1.94 | 1.31 | 1.45 | 0.89 |
| Cxcl1 | 2.82 | 9.42 | 5.26 | 2.45 | 8.33 | 0.38 |
| Cxcl12 | 1.48 | 2.29 | 1.75 | 1.37 | 1.94 | 1.25 |
| Fasl | 1.37 | 4.03 | 1.10 | 2.66 | 1.53 | 0.52 |
| Icam1 | 4.13 | 7.71 | 2.61 | 1.43 | 2.86 | 1.07 |
| Kitl | 0.66 | 0.77 | 0.95 | 0.95 | 1.09 | 0.88 |
| Nrg1 | 5.77 | 15.07 | 4.99 | 3.36 | 4.30 | 1.36 |
| Plau | 0.75 | 1.78 | 1.51 | 3.32 | 1.54 | 1.38 |
| Ptgs2/Cox2 | 6.81 | 23.04 | 5.93 | 1.50 | 8.06 | 1.00 |
| Sell | 5.74 | 16.52 | 4.40 | 1.95 | 8.78 | 1.30 |
| Tnfaip3 | 1.44 | 4.03 | 2.46 | 1.29 | 1.74 | 1.33 |
| Vcam1 | 5.24 | 19.10 | 4.26 | 1.49 | 9.10 | 1.65 |

Figure 8A

SEQ ID NOS: 3 and 4
LBA0444 Glycosyltransferase
GenBank Accession No. AAV42334

```
  1 - ATGAATATTGGTCTTTATACCGATACATATTTTCCCCAAATAAGTGGCGTAGCT - 54
  1 - M   N   I   G   L   Y   T   D   T   Y   F   P   Q   I   S   G   V   A   - 18

55 - ACTTCTATTAGGACGCTAAAAGATGCGCTTGAAAGACAGGGGCATAATGTATTT - 108
 19 - T   S   I   R   T   L   K   D   A   L   E   R   Q   G   H   N   V   F   - 36

109 - ATTTTTACAACTACAGATCCAAATGTAGAAAAGGGCACTGTTGAGCCAAATGTT - 162
 37 - I   F   T   T   T   D   P   N   V   E   K   G   T   V   E   P   N   V   - 54

163 - TTTCGTTTTAGCAGTATACCTTTTGTTTCATTCACAGATCGTAGAATTGCATTT - 216
 55 - F   R   F   S   S   I   P   F   V   S   F   T   D   R   R   I   A   F   - 72

217 - AGAGGCTTATTTGAAGCAACTAAGGTAGCTAAGGAAGTAAATTTGGATATTGTA - 270
 73 - R   G   L   F   E   A   T   K   V   A   K   E   V   N   L   D   I   V   - 90

271 - CATACACAAACTGAATTTGCTTTAGGTACAATTGGCAAATATGTAGCCCACCAA - 324
 91 - H   T   Q   T   E   F   A   L   G   T   I   G   K   Y   V   A   H   Q   - 108

325 - TTAGATATTCCTGCAATTCATACTTATCACACAATGTATGAAGATTATTTGCAT - 378
109 - L   D   I   P   A   I   H   T   Y   H   T   M   Y   E   D   Y   L   H   - 126

379 - TATATTTTAAATGGTCACTTATTGCGACCATATCATGTTAAACAATTCGTAAAA - 432
127 - Y   I   L   N   G   H   L   L   R   P   Y   H   V   K   Q   F   V   K   - 144

433 - AGCTATTTAAAAAATATGGATGGCTGTATTGCCCCAAGTGGACGTGTAGAAGAT - 486
145 - S   Y   L   K   N   M   D   G   C   I   A   P   S   G   R   V   E   D   - 162

487 - TTGTTAAAGCGATATGGCGTGCAAATTCCAATTAGGGTAATTCCTACTGGAGTA - 540
163 - L   L   K   R   Y   G   V   Q   I   P   I   R   V   I   P   T   G   V   - 180

541 - GATTTGCAGGGAATGAATGGCGATGCTGAACGTGATGTACGTCAGGAATTAGGA - 594
181 - D   L   Q   G   M   N   G   D   A   E   R   D   V   R   Q   E   L   G   - 198

595 - ATCGACAAAGATGCTCCTGTAATTTTAACTTTAAGTAGAATTGCAGCAGAAAAG - 648
199 - I   D   K   D   A   P   V   I   L   T   L   S   R   I   A   A   E   K   - 216

649 - AAAATAAATCATATTCTTAATGTGATGCCAGCAATTGTAGAAGAATTTCCAAAT - 702
217 - K   I   N   H   I   L   N   V   M   P   A   I   V   E   E   F   P   N   - 234

703 - ATTAAATTTGTAATTGCCGGTGATGGACCTGATGTTAAAGTGCTGAAAGAACAA - 756
235 - I   K   F   V   I   A   G   D   G   P   D   V   K   V   L   K   E   Q   - 252

757 - GTTGAACGTTTAACTTTAGAAGATTATGTTTTATTTGTCGGTAACGTTGATCAT - 810
253 - V   E   R   L   T   L   E   D   Y   V   L   F   V   G   N   V   D   H   - 270

811 - GGAGATGTAGGCAATTATTATCGAATGGCCGATCTTTTTGTTTCTGCCAGTGAC - 864
```

865 - ACTGAAACCCAAGGTCTTACTTATATAGAAGCTTTGGCTGCAGGTACACCATGT - 918
 289 - T   E   T   Q   G   L   T   Y   I   E   A   L   A   A   G   T   P   C   - 306

919 - GTAGTTTACGACACTGATTACACTGAAAATATTTTTGATAATGATGTCTTTGGA - 972
 307 - V   V   Y   D   T   D   Y   T   E   N   I   F   D   N   D   V   F   G   - 324

973 - CGTACTTTTGTTACACAGAAGGAAATGTTGCAAGAAATTATTGAATTATTGAAA - 1026
 325 - R   T   F   V   T   Q   K   E   M   L   Q   E   I   I   E   L   L   K   - 342

1027 - AAAGGACACAATAGAATTCCACAAGATCTTTTACAAAATAAATTGCAGAAGATT - 1080
 343 - K   G   H   N   R   I   P   Q   D   L   L   Q   N   K   L   Q   K   I   - 360

1081 - TCATCGGAGCAATTTGCTACAAATGTCCATGATTTTTATAAATACGCGATTGAT - 1134
 361 - S   S   E   Q   F   A   T   N   V   H   D   F   Y   K   Y   A   I   D   - 378

1135 - CATTATCAACCTAAACATGAAGAAATA - 1161
 379 - H   Y   Q   P   K   H   E   E   I   - 387
```

SEQ ID NOS: 5 and 6
LBA0445 Glycosyltransferase
GenBank Accession No. AAV42335

```
   1 - ATGATTAGAATTAATATGTTCTCACAAGCTGATTCAGTTAAAGGTCAAGGAGTG - 54
   1 - M   I   R   I   N   M   F   S   Q   A   D   S   V   K   G   Q   G   V   - 18

55 - GGCTCAGCCTACAATGAATTGATCAAATTATTGAGAACCCGCTTAGTAGATGAG - 108
  19 - G   S   A   Y   N   E   L   I   K   L   L   R   T   R   L   V   D   E   - 36

109 - TTTTATGTAACAATTAATAGATATGGTAATAGTGATTTAACGCACTATCATACA - 162
  37 - F   Y   V   T   I   N   R   Y   G   N   S   D   L   T   H   Y   H   T   - 54

163 - ATTAATCCAACTTATTTCGTAAATAGTTTTTCACCTGCTCGTGGAAGAAAAATA - 216
  55 - I   N   P   T   Y   F   V   N   S   F   S   P   A   R   G   R   K   I   - 72

217 - GGATATGTTCATTTTTTGCCTGATACATTAGATGGATCGCTTAAGTTGCCGGGA - 270
  73 - G   Y   V   H   F   L   P   D   T   L   D   G   S   L   K   L   P   G   - 90

271 - ATAGCTAAAAATGTGGTTTATGATTACGTGATTGATTTTTATAAGCGAATGGAT - 324
  91 - I   A   K   N   V   V   Y   D   Y   V   I   D   F   Y   K   R   M   D   - 108

325 - CAAATCGTAGTTGTAAATCCAATTTTTATTGATAAATTGGTTGATTATGGCATT - 378
 109 - Q   I   V   V   V   N   P   I   F   I   D   K   L   V   D   Y   G   I   - 126

379 - GAACGCGATAGGGTTAAATACATTCCTAATTTTGTTTCTAAAGAAGAATTTTAT - 432
 127 - E   R   D   R   V   K   Y   I   P   N   F   V   S   K   E   E   F   Y   - 144

433 - GAAGAATCATTGGCAAGTAAGAATGCCTTTCGACATGAATTAAAGATTCCACTT - 486
 145 - E   E   S   L   A   S   K   N   A   F   R   H   E   L   K   I   P   L   - 162
```

Figure 8C

```
487  - GATAAGTTTGTTGTTTTGGTGATGGACAAGTTCAAGAACGTAAAGGAATTGAT - 540
163  - D   K   F   V   V   F   G   D   G   Q   V   Q   E   R   K   G   I   D   - 180

541  - GATTTTGTAAAAATGGCTAAAGCTAATCCAGATGTTCAGTTTATTTGGGCTGGT - 594
181  - D   F   V   K   M   A   K   A   N   P   D   V   Q   F   I   W   A   G   - 198

595  - GGATTTTCGTTTGGCAAAATTACAGATGGATATAATCACTATAAAGAAATGGTG - 648
199  - G   F   S   F   G   K   I   T   D   G   Y   N   H   Y   K   E   M   V   - 216

649  - GATAATCCACCTGAAAATTTGATTTTTACAGGAATCGTAGATCGTACAAAATTA - 702
217  - D   N   P   P   E   N   L   I   F   T   G   I   V   D   R   T   K   L   - 234

703  - GTTAAGTATTTGAATATTGCTGATTTATTTGTTTTACCATCATACGATGAACTA - 756
235  - V   K   Y   L   N   I   A   D   L   F   V   L   P   S   Y   D   E   L   - 252

757  - TTCCCAATGTCTGTTCTTGAAGCGTTTAGTTGTGGGACACCAGTGCTTTTGCGC - 810
253  - F   P   M   S   V   L   E   A   F   S   C   G   T   P   V   L   L   R   - 270

811  - GATCTTGACTTATATAAGGCAATTATTGATGGCTATTATATGAGTGGAAAAGAC - 864
271  - D   L   D   L   Y   K   A   I   I   D   G   Y   Y   M   S   G   K   D   - 288

865  - TTTAGTGAAATGAATCAAATTTTGCAAAACGTAATTAAAAATCCACAATTATTG - 918
289  - F   S   E   M   N   Q   I   L   Q   N   V   I   K   N   P   Q   L   L   - 306

919  - AAAAAATATAGTGATTTATCGTTGAAGGCCAGCCAAGAATATTCAGAAGAACGA - 972
307  - K   K   Y   S   D   L   S   L   K   A   S   Q   E   Y   S   E   E   R   - 324

973  - TTAGCTAAAATTTGGAATGAATTTTATCATGAGCAATATAAATTGGGCAAAGAA - 1026
325  - L   A   K   I   W   N   E   F   Y   H   E   Q   Y   K   L   G   K   E   - 342

1027 - CTAGGACAAATTCAT - 1041
343  - L   G   Q   I   H   - 347
```

SEQ ID NOS: 7 and 8
LBA0446 Integral membrane protein
GenBank Accession No. AAV42336

```
1  - ATGAATAAAAAACATATGTGGGGCATCTTGGTTGTTTTGGCAATCAGTGTCTTT - 54
1  - M   N   K   K   H   M   W   G   I   L   V   V   L   A   I   S   V   F   - 18

55 - GTACTTTATACAGATCTAAAGTCTACACCATTATCTGACATTTTGAAGGCTGCT - 108
19 - V   L   Y   T   D   L   K   S   T   P   L   S   D   I   L   K   A   A   - 36

109 - CATGGCTTGAATGTTGGAGCATTGATAATGGTGTTTTGCTTAATGCTTTTGTCT - 162
37  - H   G   L   N   V   G   A   L   I   M   V   F   C   L   M   L   L   S   - 54

163 - TATGTATGCGAAGCAGGAATTCTTGCCGTTTTAGCACATCGAAAATCAGAGCCT - 216
55  - Y   V   C   E   A   G   I   L   A   V   L   A   H   R   K   S   E   P   - 72
```

Figure 8D

```
217 - AAGCGATCGGCATGGTCTTTTTTACGTATCCCTATTATTCAAGCACTATTTAAT - 270
 73 - K   R   S   A   W   S   F   L   R   I   P   I   I   Q   A   L   F   N   -  90

271 - GCGATAACTCCTATGTCTACAGGAGGACAGCCTTCGCAACTTGCAGCTATGATT - 324
 91 - A   I   T   P   M   S   T   G   G   Q   P   S   Q   L   A   A   M   I   - 108

325 - CAAATGGGAATGGAAGGTGGTCGATCGACTTCTATTTTGTTAATGAAATTTATT - 378
109 - Q   M   G   M   E   G   G   R   S   T   S   I   L   L   M   K   F   I   - 126

379 - ATTTATCAAATAGTTGTTTTATTTGCCTATGTATTTACCATTTTATTTGGTTTC - 432
127 - I   Y   Q   I   V   V   L   F   A   Y   V   F   T   I   L   F   G   F   - 144

433 - CATATGGTAATGACCAAGTTTGCAGGTCTCGCTATTTTTATTGCAATTGGCTTT - 486
145 - H   M   V   M   T   K   F   A   G   L   A   I   F   I   A   I   G   F   - 162

487 - TTAATCCATGTCAGTTCAATTATCTTTTTGTTGGCAATTATGTTTGCCTATCGC - 540
163 - L   I   H   V   S   S   I   I   F   L   L   A   I   M   F   A   Y   R   - 180

541 - TTTACTAAAAGAACTACTAATTGGATTATGGATTTATTGGCTAAATTTATGAAA - 594
181 - F   T   K   R   T   T   N   W   I   M   D   L   L   A   K   F   M   K   - 198

595 - AAAGAACGCGTTGAAAAATGGCGTACGGCAACTTTAGAAAAAATAGATACATTT - 648
199 - K   E   R   V   E   K   W   R   T   A   T   L   E   K   I   D   T   F   - 216

649 - TATGCTGAAAGCCAAAAGTTAAAAAAAGAGAAGAAGAAGTTAATTATGGCTTCG - 702
217 - Y   A   E   S   Q   K   L   K   K   E   K   K   K   L   I   M   A   S   - 234

703 - ATTTTAACGATTCTACAATTACTCTTTTTCTACTCAATTCCATTTATGATTTTG - 756
235 - I   L   T   I   L   Q   L   L   F   F   Y   S   I   P   F   M   I   L   - 252

757 - TCAGCTCTTAATGTTCCATGTTCATGGCTTAGTGTTACGCAGATGAATATTATG - 810
253 - S   A   L   N   V   P   C   S   W   L   S   V   T   Q   M   N   I   M   - 270

811 - ATTATTATGTTTATGGCAATTATTCCAATTCCAGGCGCATCCGGTGGAGCAGAA - 864
271 - I   I   M   F   M   A   I   I   P   I   P   G   A   S   G   G   A   E   - 288

865 - TATAGTTTTCAGACGTTATTTTCAACATTTATTTCTACGCATGGTGCCTTAATT - 918
289 - Y   S   F   Q   T   L   F   S   T   F   I   S   T   H   G   A   L   I   - 306

919 - TTGGCAATGTTTATCTGGCGTTTTTCAACTTATTTCTTTGGAATGATCTTAGGA - 972
307 - L   A   M   F   I   W   R   F   S   T   Y   F   F   G   M   I   L   G   - 324

973 - ATATTTGGTTGGATTTTTAAGCCTAAAAAGATAAAAAGCTCAGAAAGTAAT    - 1023
325 - I   F   G   W   I   F   K   P   K   K   I   K   S   S   E   S   N       - 341
```

Figure 8E

SEQ ID NOS: 1 and 2
LBA0447 Phosphoglycerol transferase
GenBank Accession No. AAV42337

```
  1 - ATGGAACGTACCAAATCTTTTTTTAAATGGTTGACGCAAACTAAGCTGGGATTT - 54
  1 - M   E   R   T   K   S   F   F   K   W   L   T   Q   T   K   L   G   F  - 18

55 - TTTACAATAGTTTTAGTATTGTTTTGGCTAAAAACATATTATATTTATTTAACT - 108
 19 - F   T   I   V   L   V   L   F   W   L   K   T   Y   Y   I   Y   L   T  - 36

109 - AAGTTCAACTTGGGTGCAGTTGGTCCTATGCAGCAATTTTTGCTTTTAATTAAC - 162
 37 - K   F   N   L   G   A   V   G   P   M   Q   Q   F   L   L   L   I   N  - 54

163 - CCTATTCCATCAGGGATGCTGCTACTAGGTATTGGCCTATTTTTTAAGGGACGA - 216
 55 - P   I   P   S   G   M   L   L   L   G   I   G   L   F   F   K   G   R  - 72

217 - AAATCTTATTGGATTATTCTGATAATCGATTTTTTATTAACGCTGTGGCTTTTT - 270
 73 - K   S   Y   W   I   I   L   I   I   D   F   L   L   T   L   W   L   F  - 90

271 - TCTAATATTTTATATTATCGAGAATTTTCTAATTTCTTGTCTTTTTCAATTATT - 324
 91 - S   N   I   L   Y   Y   R   E   F   S   N   F   L   S   F   S   I   I  - 108

325 - AAGACATCAGGATCGACATCCGATAATCTGGGAAAAAGTATTGCAGGAATAACT - 378
109 - K   T   S   G   S   T   S   D   N   L   G   K   S   I   A   G   I   T  - 126

379 - TTAGCAAGTGATTTTTTAGCATTTTTGGATATTGCAGTTATTATTGCGTTATTA - 432
127 - L   A   S   D   F   L   A   F   L   D   I   A   V   I   I   A   L   L  - 144

433 - GCTACTAAAGTTATTAAAATGGATGTGCGTCCATTAAAGTTAAAAGTGAGTCTT - 486
145 - A   T   K   V   I   K   M   D   V   R   P   L   K   L   K   V   S   L  - 162

487 - TTAATTGAATTTTTGGCACTTAGTTTAATGGGACTTAATTTATTGATGGCCCAA - 540
163 - L   I   E   F   L   A   L   S   L   M   G   L   N   L   L   M   A   Q  - 180

541 - AAAGATAGATCAGGTCTTTTAACTAGAACCTTTGATAATAACTATATTGTTAAA - 594
181 - K   D   R   S   G   L   L   T   R   T   F   D   N   N   Y   I   V   K  - 198

595 - TATCTAGGAATTAATGAATACGCTATTTATGATGGATATAAAACAGCCCAAACA - 648
199 - Y   L   G   I   N   E   Y   A   I   Y   D   G   Y   K   T   A   Q   T  - 216

649 - AGCGCCCAAATGGCTAAGGCAAACGTATCTGATTTAAAATCTGTACGTAATTAT - 702
217 - S   A   Q   M   A   K   A   N   V   S   D   L   K   S   V   R   N   Y  - 234

703 - TTAAATGCAAACAAGGTAAAACCTAATCCAGAATATACGGGTGTAGCAAAAGGA - 756
235 - L   N   A   N   K   V   K   P   N   P   E   Y   T   G   V   A   K   G  - 252

757 - AAAAACGTTTTAGTTATTCACCTTGAAAGTTTTCAACAATTTTTAATTGGCTAT - 810
253 - K   N   V   L   V   I   H   L   E   S   F   Q   Q   F   L   I   G   Y  - 270

811 - AAATGGAAGGGTAAAGAAGTAACACCTAATTTAAATAAAATATATCATCAAAAA - 864
271 - K   W   K   G   K   E   V   T   P   N   L   N   K   I   Y   H   Q   K  - 288
```

Figure 8F

```
 865 - GATACGATTAGCTTTGATAATTTCTTTAACCAGGTAGGACAAGGTAAAACTTCA -  918
 289 - D   T   I   S   F   D   N   F   F   N   Q   V   G   Q   G   K   T   S   -  306

919 - GATGCTGAAATGATGTTAGAAAATTCATTATATGGTTTGCAGTCTGGGTCAGCT -  972
 307 - D   A   E   M   M   L   E   N   S   L   Y   G   L   Q   S   G   S   A   -  324

973 - ATGTCTACTTATGGCACGTCAAATACGTTTGAAAGTGCACCAGCGATTTTGCAC - 1026
 325 - M   S   T   Y   G   T   S   N   T   F   E   S   A   P   A   I   L   H   -  342

1027 - CAACAAGCAGGTTATACTACTGCAGTAATGCATGGTGGTGCAGGATCGTTCTGG - 1080
 343 - Q   Q   A   G   Y   T   T   A   V   M   H   G   G   A   G   S   F   W   -  360

1081 - AATAGAAATAATGCATATAAATCATTTGGTTATCAATATTTTATGCCATTATCA - 1134
 361 - N   R   N   N   A   Y   K   S   F   G   Y   Q   Y   F   M   P   L   S   -  378

1135 - TTTTATGAAAATAAACCCAGCTATTATATTGGATATGGTTTAAAAGATAAGATT - 1188
 379 - F   Y   E   N   K   P   S   Y   Y   I   G   Y   G   L   K   D   K   I   -  396

1189 - TTCTTTGATCAATCAATTAAATATATTGAACGTTTACCACAGCCATTTTATTTA - 1242
 397 - F   F   D   Q   S   I   K   Y   I   E   R   L   P   Q   P   F   Y   L   -  414

1243 - AAGATGATCACAGTAACTAATCATTATCCATACGATATTGACAAGAAGAATCAA - 1296
 415 - K   M   I   T   V   T   N   H   Y   P   Y   D   I   D   K   K   N   Q   -  432

1297 - TCCATTGCTAAGACTAATACTGGGGATGAAACTGTTGATGGTTACGTTCAAACA - 1350
 433 - S   I   A   K   T   N   T   G   D   E   T   V   D   G   Y   V   Q   T   -  450

1351 - GCGCATTATCTTGATCAAGCAATTGGAGAACTAATGAGCTGGATGAAGAAGACT - 1404
 451 - A   H   Y   L   D   Q   A   I   G   E   L   M   S   W   M   K   K   T   -  468

1405 - GGACTAGATAAAAAGACATTGATTGTCTTTTATGGCGATCACTATGGTATTTCT - 1458
 469 - G   L   D   K   K   T   L   I   V   F   Y   G   D   H   Y   G   I   S   -  486

1459 - GGAAATCACCATAAAGCTAGTGCACAACTTCTTAAGAAAAAATCATTTAATGAT - 1512
 487 - G   N   H   H   K   A   S   A   Q   L   L   K   K   K   S   F   N   D   -  504

1513 - TTTGATAATTTGCAGTTTCAAAGAGTGCCTTTAATGTTTCATATGAAAGGATTA - 1566
 505 - F   D   N   L   Q   F   Q   R   V   P   L   M   F   H   M   K   G   L   -  522

1567 - AAGGGTGGAATAAATCATACTTATGGTGGTGAAATTGATGTTTTACCAACTTTG - 1620
 523 - K   G   G   I   N   H   T   Y   G   G   E   I   D   V   L   P   T   L   -  540

1621 - TTAAATTTACTCGGTATTAAAGATAGCGATACTATTCAATTTGGCTACGATTTA - 1674
 541 - L   N   L   L   G   I   K   D   S   D   T   I   Q   F   G   Y   D   L   -  558

1675 - CTTAGCAAAAACGCACCCCAAATTGTAGCCCAAAGAAATGGAGACTTTATTACA - 1728
 559 - L   S   K   N   A   P   Q   I   V   A   Q   R   N   G   D   F   I   T   -  576

1729 - CCAGAATATTCAAAAGTTGGTAGCGATTATTATTACACTAAGACTGGTAAAAGA - 1782
 577 - P   E   Y   S   K   V   G   S   D   Y   Y   Y   T   K   T   G   K   R   -  594

1783 - ATTAAGCCTAATAAGAAATTAAAAGCTGAATTGACGGCAATTTCTAACACTGTG - 1836
```

1837 - ACAACGCAGCTTTCTTTATCAGATCGTGTAATTAACGGTAATTTATTACGGTTT - 1890
 613 - T   T   Q   L   S   L   S   D   R   V   I   N   G   N   L   L   R   F  -  630

1891 - TATCGTCCTAAGTGGTTTACTAAGGTTAAGCCAAAAGACTACGATTATAATAAG - 1944
 631 - Y   R   P   K   W   F   T   K   V   P   K   D   Y   D   Y   N   K  -  648

1945 - GAACCATCGTTAAAACGTTTATTTAATGATCCAAGTAAAACGTCTCTATGGTAT - 1998
 649 - E   P   S   L   K   R   L   F   N   D   P   S   K   T   S   L   W   Y  -  666

1999 - CAAAATCATAAAAAGACGACGCAAAAGATTTTAAAACTGATGCGCCTGAGTTG - 2052
 667 - Q   N   H   K   K   T   T   Q   K   D   F   K   T   D   A   P   E   L  -  684

2053 - AAAAAA - 2058
 685 - K   K       - 686
```

SEQ ID NOS: 9 and 10
LBA1926 D-alanine--D-alanyl carrier protein ligase, DltA
GenBank Accession No. AAV43723

```
   1 - ATGATTCAAGATGTTATTAAGAGAATTGACGAGATAGCTGAAAATGAACCAGAT -  54
   1 - M   I   Q   D   V   I   K   R   I   D   E   I   A   E   N   E   P   D  -  18

55 - CGTGTAGTTTACGATTATCTCGGTGAAACCAATACATATGGTGACCTTAAGAAG - 108
  19 - R   V   V   Y   D   Y   L   G   E   T   N   T   Y   G   D   L   K   K  -  36

109 - CGTTCAAACGCTTGGGCACACAAGATTGCTAGTATGGATATCCCAGAACATGCA - 162
  37 - R   S   N   A   W   A   H   K   I   A   S   M   D   I   P   E   H   A  -  54

163 - CCAATCATGATCTGGGGTGGTCAAACATTTGAAATGATTGCTAGTTTCTTAGGT - 216
  55 - P   I   M   I   W   G   G   Q   T   F   E   M   I   A   S   F   L   G  -  72

217 - TGTGTTAAATCAGGCCACGCATATATTCCAATTGCAAGTTATTCAAATGCTGAA - 270
  73 - C   V   K   S   G   H   A   Y   I   P   I   A   S   Y   S   N   A   E  -  90

271 - CGTTTAACAATGATTCAAGATGTTTCAAAATCACCTATGGTTTTGGAAATTGAT - 324
  91 - R   L   T   M   I   Q   D   V   S   K   S   P   M   V   L   E   I   D  -  108

325 - CCATTGCCAGACGTTAATTTAGACGGCATCAAGGTACTTAAAGCTAATGAAGTT - 378
 109 - P   L   P   D   V   N   L   D   G   I   K   V   L   K   A   N   E   V  -  126

379 - GAAGATGGCGACTTTACAGTTGATGAAAGTAATTTCGTTGAAGGCGACGAAAAT - 432
 127 - E   D   G   D   F   T   V   D   E   S   N   F   V   E   G   D   E   N  -  144

433 - TACTATATTATCTTTACTTCAGGTACTACTGGTAAGCCAAAGGGTGTACAAATC - 486
 145 - Y   Y   I   I   F   T   S   G   T   T   G   K   P   K   G   V   Q   I  -  162

487 - AGTCATGATAATTTGTTGAGTTTTGTAAACTGGGAATTATCAGATTTTAATTTG - 540
```

541 - CCAGAACACCCAAGCTTTTTGGCACAAGCTCCATACTCATTTGACTTGTCAGTT -  594
 181 - P   E   H   P   S   F   L   A   Q   A   P   Y   S   F   D   L   S   V   -  198

595 - ATGAGCCTTTATCCTGCACTTGTTTCAGCAGGAAAGCTTGTTGTTTTACCACAT -  648
 199 - M   S   L   Y   P   A   L   V   S   A   G   K   L   V   V   L   P   H   -  216

649 - GATGTTACGCAAAACTTTGGTCAATTGTTCCAAACTTTACCAAAAATGCAATTT -  702
 217 - D   V   T   Q   N   F   G   Q   L   F   Q   T   L   P   K   M   Q   F   -  234

703 - AATGTTTGGGTATCAACTCCATCATTTGCACAAATGTGTTTCTTAGATAAAACC -  756
 235 - N   V   W   V   S   T   P   S   F   A   Q   M   C   F   L   D   K   T   -  252

757 - TTTGATGCAGAACATCATCCAGACTTAACTCACTTCTTATTCTGTGGTGAAGAA -  810
 253 - F   D   A   E   H   H   P   D   L   T   H   F   L   F   C   G   E   E   -  270

811 - TTACCACATAGTGAAGCTGATATGCTTAAGAAGAAGTTCCCAGAAAGTCATATT -  864
 271 - L   P   H   S   E   A   D   M   L   K   K   K   F   P   E   S   H   I   -  288

865 - TTTAATACTTACGGTCCTACTGAAACTACAGTTGCTGTGACTCAAGTAGAGATC -  918
 289 - F   N   T   Y   G   P   T   E   T   T   V   A   V   T   Q   V   E   I   -  306

919 - ACTGATGAAATACTTGAAAAGTATGATCGTCTACCAATTGGTAGAGTAAAAGAA -  972
 307 - T   D   E   I   L   E   K   Y   D   R   L   P   I   G   R   V   K   E   -  324

973 - GACACTAAGATTACTATTGATACTTCAAAGGGAGATAAGCCTGGCGAAGGTGAA - 1026
 325 - D   T   K   I   T   I   D   T   S   K   G   D   K   P   G   E   G   E   -  342

1027 - ATCATTATCAGTGGTCCTAGCGTTTCAAAAGGGTACATGAATAACCCTGAAAAG - 1080
 343 - I   I   I   S   G   P   S   V   S   K   G   Y   M   N   N   P   E   K   -  360

1081 - ACCGAAGCTGCTTTCTTCCAAAATGAGGGCGACAAGTATCGCAGCTACCGTAGT - 1134
 361 - T   E   A   A   F   F   Q   N   E   G   D   K   Y   R   S   Y   R   S   -  378

1135 - GGAGATGCTGGATTCTTTGATGGTGATATGCTATTTTATCGCGGTAGAATCGAC - 1188
 379 - G   D   A   G   F   F   D   G   D   M   L   F   Y   R   G   R   I   D   -  396

1189 - TTCCAAATCAAGTTCAATGGTTACAGAATCGAACTTGAAGAAATTAATTTCTAC - 1242
 397 - F   Q   I   K   F   N   G   Y   R   I   E   L   E   E   I   N   F   Y   -  414

1243 - TTGTCAAAGAATGAATTTGTACGTTATGGTGTCGCAGCACCTAAATACAATAAA - 1296
 415 - L   S   K   N   E   F   V   R   Y   G   V   A   A   P   K   Y   N   K   -  432

1297 - GATCATACTGTAAAGCAAATTGTTGCTGAAATCGAATTGAAGCATGGCGTTCGT - 1350
 433 - D   H   T   V   K   Q   I   V   A   E   I   E   L   K   H   G   V   R   -  450

1351 - CGTAAGTATTCTGATGCACAACTTACTAAGTTGATTCGTGAAGACTTAGCTAAG - 1404
 451 - R   K   Y   S   D   A   Q   L   T   K   L   I   R   E   D   L   A   K   -  468

1405 - AACGTGATGCCTTACATGATTCCACAGCGTTATGTTTACCAAGATACATTACCA - 1458
 469 - N   V   M   P   Y   M   I   P   Q   R   Y   V   Y   Q   D   T   L   P   -  486
```

Figure 8I

```
1459 - ATTTCTCAAAACGGTAAGGTGGATATTAAGGCAGTTATTAAGGAGGTTAATAAG - 1512
 487 - I   S   Q   N   G   K   V   D   I   K   A   V   I   K   E   V   N   K  - 504
```

SEQ ID NOS: 11 and 12
LBA1925 D-alanyl transfer protein DltB
GenBank Accession No. AAV43722

```
  1 - GTGAATTTTAATTTCATTAACTTACAACCTTACTCAAATCCGCAATATTTTGTT -  54
  1 - M   N   F   N   F   I   N   L   Q   P   Y   S   N   P   Q   Y   F   V  -  18

55 - TACTTGATGATCGCGTTAATTCCTATTATTATTGGACTTTACTATGGTCATCGT - 108
 19 - Y   L   M   I   A   L   I   P   I   I   I   G   L   Y   Y   G   H   R  -  36

109 - CTCAAGACATATGAAGCGATTTTCTCAATTGTTTTCTTATTCTTGATTTTTGAC - 162
 37 - L   K   T   Y   E   A   I   F   S   I   V   F   L   F   L   I   F   D  -  54

163 - GGTAGTCACTGGCAACAAGGTGTAAACTTGCTAATCTGGCTGGTTTATGAATTT - 216
 55 - G   S   H   W   Q   Q   G   V   N   L   L   I   W   L   V   Y   E   F  -  72

217 - GCTTTGACGTTTGCTTATCAGTATTATCGTCATCATGGTAAAAATAAGACTTGG - 270
 73 - A   L   T   F   A   Y   Q   Y   Y   R   H   H   G   K   N   K   T   W  -  90

271 - GTATTTAGCTTGGCTGTAATTTTAGCGATTATTCCGCTGGCTGCAGTTAAGTAT - 324
 91 - V   F   S   L   A   V   I   L   A   I   I   P   L   A   A   V   K   Y  - 108

325 - TTGACCGCATTCCCACTTAATTCAATCAACTTTGTTATTGGATTTTTAGGTATT - 378
109 - L   T   A   F   P   L   N   S   I   N   F   V   I   G   F   L   G   I  - 126

379 - TCTTACGTAACTTTCAAAACAGTGCAAGTTATTATGGAAATGCGTGACGGTGCG - 432
127 - S   Y   V   T   F   K   T   V   Q   V   I   M   E   M   R   D   G   A  - 144

433 - ATTAAGAAGGTGGATCCTGTAACCTATGCAAGATTCTTACTCTTCTTCCCAACT - 486
145 - I   K   K   V   D   P   V   T   Y   A   R   F   L   L   F   F   P   T  - 162

487 - ATTTCATCAGGTCCTATTGATCGATATCGTAGATTTAAGAAAGATTACGATAAA - 540
163 - I   S   S   G   P   I   D   R   Y   R   R   F   K   K   D   Y   D   K  - 180

541 - GTTCCTACAAGAGACGCATATATTACAGATTTACAATATGCTGTAAGATATTTG - 594
181 - V   P   T   R   D   A   Y   I   T   D   L   Q   Y   A   V   R   Y   L  - 198

595 - TTCCAAGGATTTTTATACAAATTTATTATTGGTTGGTTCTTTGGTACTTATTGG - 648
199 - F   Q   G   F   L   Y   K   F   I   I   G   W   F   F   G   T   Y   W  - 216

649 - CTTCCTAAGATTAGTGCCGCTGCTTTAGCGGTGGGAAATGCTAATGGTGGTTTG - 702
217 - L   P   K   I   S   A   A   A   L   A   V   G   N   A   N   G   G   L  - 234

703 - AAGTTATCATGGTGGCTTCTTGCTTACATGTATTGCTACAGTATGTACCTGTTC - 756
235 - K   L   S   W   W   L   L   A   Y   M   Y   C   Y   S   M   Y   L   F  - 252
```

Figure 8J

```
757  - TTTGACTTTGCAGGTTACTCACTATTTGCTGTATCAATTTCATACTTCATGGGT - 810
253  - F   D   F   A   G   Y   S   L   F   A   V   S   I   S   Y   F   M   G   - 270

811  - ATTCATACCCCAATGAACTTCAACAAACCATTTATTTCTAAGAATATTAAAGAC - 864
271  - I   H   T   P   M   N   F   N   K   P   F   I   S   K   N   I   K   D   - 288

865  - TTCTGGAACCGTTGGCACATTACACTTTCATTCTGGTTCCGTGATTATATCTAC - 918
289  - F   W   N   R   W   H   I   T   L   S   F   W   F   R   D   Y   I   Y   - 306

919  - ATGCGATTCACTTTCTTTGCAATGAAAAAAAAGTTGTTTAAGAATCGTATTAGA - 972
307  - M   R   F   T   F   F   A   M   K   K   K   L   F   K   N   R   I   R   - 324

973  - TTGTCACAGGTATCATATTTCCTATTATTCTTGATAATGGGATTCTGGCATGGG - 1026
325  - L   S   Q   V   S   Y   F   L   L   F   L   I   M   G   F   W   H   G   - 342

1027 - TTAACATGGTATTATATTGTTTATGGTATATTCCATGCCACTGCTATCTGTGTC - 1080
343  - L   T   W   Y   Y   I   V   Y   G   I   F   H   A   T   A   I   C   V   - 360

1081 - AACGATATGTGGCTAAGATTTAAGAGAAAGCATAAGAAACAAATTCCACATAAC - 1134
361  - N   D   M   W   L   R   F   K   R   K   H   K   K   Q   I   P   H   N   - 378

1135 - AAGTTTACTGAATGGTTTGCCATTTTCTTAACTTTCAATATGGTATGTTTCAGT - 1188
379  - K   F   T   E   W   F   A   I   F   L   T   F   N   M   V   C   F   S   - 396

1189 - TTCTTGATTTTCTCAGGATTCCTTAGTCAATTGTGGTTTGGCTGGAAG - 1236
397  - F   L   I   F   S   G   F   L   S   Q   L   W   F   G   W   K   - 412
```

SEQ ID NOS: 13 and 14

LBA1924 D-alanine--poly(phosphoribitol) ligase subunit 2, DltC
GenBank Accession No. AAV43721

```
1  - ATGGACACTAAACAAGGCGTATTAGACATTTTAAACGATTTAACTGGTGAAGAT - 54
1  - M   D   T   K   Q   G   V   L   D   I   L   N   D   L   T   G   E   D   - 18

55 - TTATCAGATCAAATGGATGAAAACATCTTTGATAATGGTTTGATGGACTCAATG - 108
19 - L   S   D   Q   M   D   E   N   I   F   D   N   G   L   M   D   S   M   - 36

109 - GCAAGTGTACAAATGCTTTTGAGTTTACAAGAAAAATTTGATATTGATGTTCCT - 162
37  - A   S   V   Q   M   L   L   S   L   Q   E   K   F   D   I   D   V   P   - 54

163 - GTATCAGAATTTAATCGTGAAGAATGGGACACTCCTAACAAGATTGTTGCAAAG - 216
55  - V   S   E   F   N   R   E   E   W   D   T   P   N   K   I   V   A   K   - 72

217 - GTGGAAAGCTTAGAAAATGAG - 237
73  - V   E   S   L   E   N   E   - 79
```

Figure 8K

SEQ ID NOS: 15 and 16
LBA1923  D-alanyl transfer protein DltD
GenBank Accession No. AAV43720

```
  1 - ATGAGTAATAAACGCCGGCTGTGGCAAATTTTTGGCCCAGTTCTTTGCGCTTTT -  54
  1 - M  S  N  K  R  R  L  W  Q  I  F  G  P  V  L  C  A  F  -  18

55 - ATCCTTTTATTAGTTGTATTTCTTATTCCCTGGGAAAGAACTTTTTCTAAGCAA - 108
 19 - I  L  L  V  V  F  L  I  P  W  E  R  T  F  S  K  Q     -  36

109 - ACTATCTATGAAGCAGCTGCCTCACAAAATAGTACTGTATTTAAGGGCAGTACA - 162
 37 - T  I  Y  E  A  A  A  S  Q  N  S  T  V  F  K  G  S  T  -  54

163 - ATGAAGCAAGAAGCTTATAAAGATGGTTATGTACCATTCTATGGTTCAAGTGAA - 216
 55 - M  K  Q  E  A  Y  K  D  G  Y  V  P  F  Y  G  S  S  E  -  72

217 - TTGTCTAGATTTGATCCACTTCACCCTAGTGTTATTGCTGAAAAGTATCACAGA - 270
 73 - L  S  R  F  D  P  L  H  P  S  V  I  A  E  K  Y  H  R  -  90

271 - AATTACCGTCCATTTCTTCTAGGTGGACCAGGTAGTCAATCTTTGGCTCAATTC - 324
 91 - N  Y  R  P  F  L  L  G  G  P  G  S  Q  S  L  A  Q  F  - 108

325 - TTGGGGATGCAGGGTACAACTAAACAGCTTAAAAACAAAAAGGCTGTAGTGATT - 378
109 - L  G  M  Q  G  T  T  K  Q  L  K  N  K  K  A  V  V  I  - 126

379 - ATTTCACCACAATGGTTTACCAAGAAAGGCCAAGATCCTAATGCATTTGCTTTA - 432
127 - I  S  P  Q  W  F  T  K  K  G  Q  D  P  N  A  F  A  L  - 144

433 - TATTATTCACCACTTCAAGCATGTAACTTCTTGTTAAGTGCTAAGAATAATAAG - 486
145 - Y  Y  S  P  L  Q  A  C  N  F  L  L  S  A  K  N  N  K  - 162

487 - ACTGATCGTTATGCTGCTAAGCGTCTGCTTGATATGCCAGATGTAAAGGGTGAA - 540
163 - T  D  R  Y  A  A  K  R  L  L  D  M  P  D  V  K  G  E  - 180

541 - ATTAGAAACAGTCTTAAGCAAATTGCTGCAGGTAAAAAGCTAACTACTTTTGAA - 594
181 - I  R  N  S  L  K  Q  I  A  A  G  K  K  L  T  T  F  E  - 198

595 - AGATTTTATTTAGAAAATCGTCGTAGAATGTTACGTAACGAAGATAACTTCTTT - 648
199 - R  F  Y  L  E  N  R  R  R  M  L  R  N  E  D  N  F  F  - 216

649 - AGTTCATTCCAATTACGCGATCGTGTAAATAAGATTCAAAATAGAGCTAAAGTA - 702
217 - S  S  F  Q  L  R  D  R  V  N  K  I  Q  N  R  A  K  V  - 234

703 - TTACCTAATACTTATTCTGTAGCTGCTTTGAACAAGGTGGCTGAAGAACAGGCT - 756
235 - L  P  N  T  Y  S  V  A  A  L  N  K  V  A  E  E  Q  A  - 252

757 - GCAGCACATACTACTTCAAATAACTTGGGAATTGACAATACTTTCTATAGAACT - 810
253 - A  A  H  T  T  S  N  N  L  G  I  D  N  T  F  Y  R  T  - 270

811 - CGTTTGCCTAGAAAGGTATTAAAGAGACTCAAGGGTAGTCAACGTCACTTTGAT - 864
```

865 - TACGTTAGATCTGTTGAATATGGCGACTTCCAGTTAATGCTGGAACAATTTGCC - 918
 289 - Y  V  R  S  V  E  Y  G  D  F  Q  L  M  L  E  Q  F  A    -  306

919 - AAGCAACATACTAATGTGTTGTTCATTATTCCACCAATTAATGGTAAGTGGATG - 972
 307 - K  Q  H  T  N  V  L  F  I  I  P  P  I  N  G  K  W  M    -  324

973 - AAGTATACTGGTTTATCACAAAAAATGTATCAAGAATCAGTTGCTAAAATTGAA - 1026
 325 - K  Y  T  G  L  S  Q  K  M  Y  Q  E  S  V  A  K  I  E    -  342

1027 - CAACAATTGACTAGTCAAGGTTTTGAAAATATTGCAGATCTTTCTAAACGTGGT - 1080
 343 - Q  Q  L  T  S  Q  G  F  E  N  I  A  D  L  S  K  R  G    -  360

1081 - AATGAAAAGTACTTCATGCAAGATACTATTCACCTTGGTTGGAAAGGCTGGGTA - 1134
 361 - N  E  K  Y  F  M  Q  D  T  I  H  L  G  W  K  G  W  V    -  378

1135 - GCTGTTGATCAAGCTGTTAGACCATTTATGAAGTTGCCTAACGAACGTTACAAC - 1188
 379 - A  V  D  Q  A  V  R  P  F  M  K  L  P  N  E  R  Y  N    -  396

1189 - TATGATATGTCTAACTACTACTTCTCAAAGAAGTGGCAGAATAAAGATAACGTT - 1242
 397 - Y  D  M  S  N  Y  Y  F  S  K  K  W  Q  N  K  D  N  V    -  414

1243 - AAACGTGTAAATTTAAATAATAAAGATCGTTTAAAAGTGAAG - 1284
 415 - K  R  V  N  L  N  N  K  D  R  L  K  V  K       -  428
```

RECOMBINANT LACTOBACILLUS WITH DECREASED LIPOTEICHOIC ACID TO REDUCE INFLAMMATORY RESPONSES

This application is the U.S. National Stage of International Application PCT/US2011/040674, filed Jun. 16, 2011, which designates the U.S. and was published by the International Bureau in English on Dec. 22, 2011, and which claims the benefit of U.S. Provisional Application Nos. 61/356,165, filed Jun. 17, 2010 and 61/433,598, filed Jan. 18, 2011, all of which are hereby incorporated by reference in their entirety.

FIELD OF THE INVENTION

The present invention relates to methods and compositions for decreasing inflammation.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 406734seqlist.txt, a creation date of Jun. 16, 2011, and a size of 15.7 KB. The sequence listing filed via EFS-Web is part of the specification and is hereby incorporated in its entirety by reference herein.

BACKGROUND OF THE INVENTION

The maintenance of intestinal immune homeostasis involves the balanced interaction of bacterial microflora, gut epithelium and host innate immune cells. Deregulation of these immunological interactions can result in immune dysfunction and lead to overt inflammation typical of human inflammatory bowel disease (IBD), including ulcerative colitis (UC) and Crohn's disease. Although the cellular and molecular mechanisms of IBD are not fully understood, data indicate that chronic intestinal inflammation induced by inflammatory cytokines (e.g. IL-12) plays a pivotal role. These cytokines initiate the differentiation of pathogenic CD4+ T cells that are strongly involved in disease progression. Accordingly, studies show that regulation of these cells mitigates experimental colitis. Additionally, like IL-12, secreted IL-23 from activated dendritic cells (DCs) that utilize the IL-12p40 subunit is also implicated in the development of various autoimmune diseases, including IBD. The inflammatory nature of IL-23 has been attributed to induction of Th17. Furthermore, this cytokine also activates the production of inflammatory cytokines such as TNFα and IL-6 in DCs. Together, studies show that blocking the IL-12p40 subunit signaling significantly reduces inflammation, and indicate that both IL-12 and IL-23 participate in the inflammatory cascade causing IBD. In contrast to both of these cytokines, IL-10 exerts regulatory effects on the inflammatory signals, thereby modulating the immune response elicited by inflammatory cytokines.

Probiotic microbes can interact with the host's immune cells and specific probiotic *Lactobacillus* species may stimulate DCs to produce inflammatory cytokines (i.e. IL-12) and regulatory IL-10. Lactobacilli are normal inhabitants of the human gastrointestinal tract and major components of the natural microbiota in the small bowel. These bacteria are considered beneficial commensals and some species and strains are generally recognized as safe due to a long history of human consumption.

Further methods and compositions are needed in the art to improve the treatment of inflammatory gastrointestinal disorders, such as IBD.

BRIEF SUMMARY OF THE INVENTION

Methods and compositions for decreasing inflammation in a subject are provided. The compositions comprise a recombinant bacterium genetically modified to decrease the display of lipoteichoic acid on the cell surface. Methods comprise administering to a subject a recombinant bacterium modified to decrease the display of lipoteichoic acid on the cell surface. Administration of the recombinant bacterium promotes a desired therapeutic response. The recombinant bacterium may be administered in a single dose or series of doses. Methods find use in treating or preventing a variety of inflammatory disorders including, for example, treating or preventing inflammatory bowel disease, colitis, or Crohn's disease.

BRIEF DESCRIPTION OF THE DRAWINGS

FIG. 8 provides the sequences of SEQ ID NOS: 1-16.

DETAILED DESCRIPTION OF THE INVENTION

Figure 1:
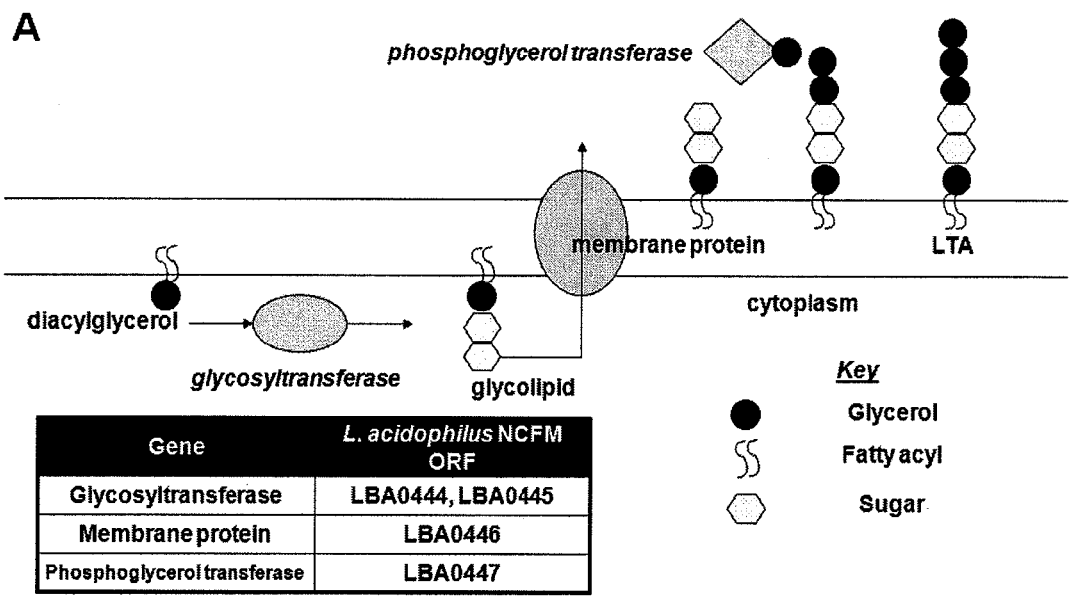
FIGS. 1 (A and B) shows the pathway and genes involved in LTA biosynthesis. C-D shows two noncontiguous fragments flanking an internal region of the target ORF amplified and joined using splicing by overlap extension (SOEing) PCR (Horton, R M (1995) *Mol Biotechnol*. April; 3(2):93-9). The resulting fragments were cloned into pORI28 and transformed into *L. acidophilus* NCK1392 containing the temperature sensitive helper plasmid pTRK669. ERM-sensitive cells were screened for a deletion mutation using PCR with primers flanking the targeted region and confirmed by sequencing the region containing the deletion.
Figure 1:
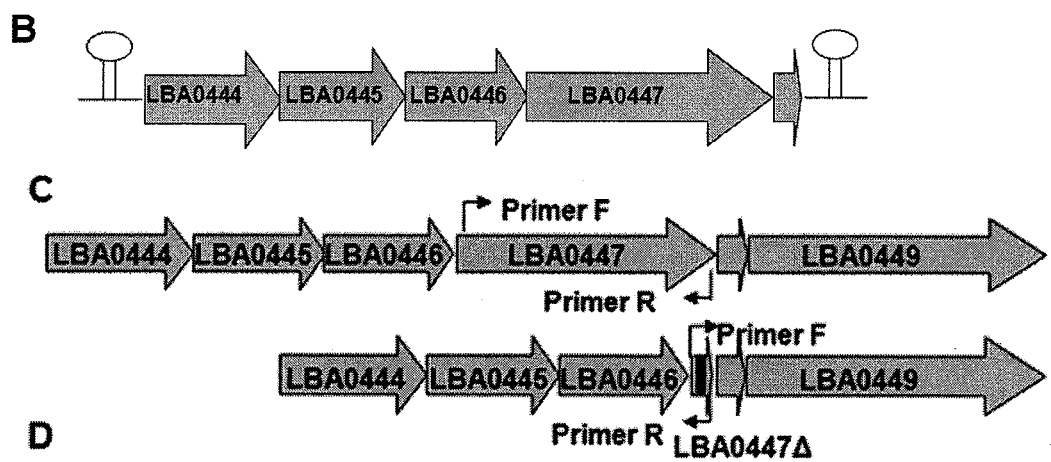
Figure 1:
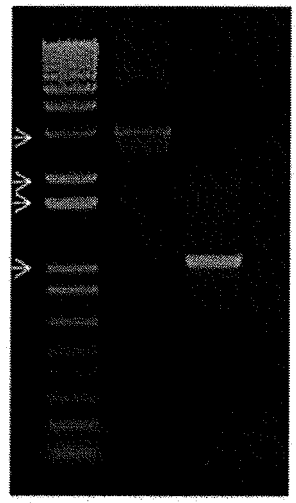

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Overview

Methods and compositions for decreasing inflammation in a subject are provided, including methods and compositions for treating or preventing inflammatory disorders. Such methods and compositions can be employed to reduce inflammation in the gastrointestinal tract using recombinant bacteria modified to decrease the display of LTA on the bacterial cell surface. Overt inflammation of the gastrointestinal tract is representative of human IBD, including uncreative colitis and Crohn's disease. By decreasing the display of LTA on the cell surface, the recombinant bacteria of the present invention reduce the net inflammatory response significantly more than the corresponding wild-type bacterial cells. Accordingly, various recombinant bacteria and methods of their use are provided which reduce the inflammatory response by stimulating the production of anti-inflammatory cytokines and limiting the production of pro-inflammatory cytokines in a subject in need thereof.

Recombinant Bacterial Cells with Decreased Display of LTA

Methods and compositions are provided which decrease the display of LTA on the surface of a cell. As used here, a decrease in the display of LTA on the surface of a cell comprises any statistically significant decrease in the level of LTA displayed on the surface of a cell, when compared to an appropriate control. Such decrease can include, for example, at least a 5%, 10%, 20%, 30%, 40%, 50%, 60%, 70%, 80%, 90%, or 100% decrease in the amount of LTA displayed on the surface of a cell. Methods to assay for the amount of LTA on the surface of a cell include, for example, butanol and hydrophobic interaction chromatography (Morath S, Geyer A, & Hartung T (2001) *J Exp Med* 193(3):393-397) or enzyme-linked immunosorbent assay (ELISA) (Tadler et al. (2005) *J Clin Lab Anal.* 1989; 3(1):21).

The term "surface," "cell surface" or "bacterial surface," as used herein refers to an area of the bacterial cell including and external to the plasma membrane. Gram positive bacteria contain a layer of peptidoglycan external to the plasma membrane with teichoic acids interspersed within. Gram negative bacteria further contain an outer membrane covering the peptidoglycan layer. Thus, display of the LTA on the surface according to the invention can be in or on the plasma membrane or peptidoglycan layer of Gram positive bacteria, or in or on the plasma membrane, peptidoglycan layer, or outer membrane of Gram negative bacteria.

Recombinant bacterial cells are provided which have been genetically modified to decrease the display of LTA on the cell surface. As used herein, the terms "recombinant bacterium" or "recombinant bacterial cells" refer to a bacterium or plurality or bacterial cells in which at least one genetic alteration, has been effected as to a gene of interest, or a cell which is descended from a cell so altered and which comprises the genetic alteration. Accordingly, as used herein, the term "genetically modified" or "genetic modification" refers to a genetic alteration, such as a deletion, addition or substitution, which has been effected as to a gene or nucleic acid sequence of interest. In some embodiments, the genetic alteration is an alteration caused by a recombinant technique at the hand of man.

In some embodiments a genetic alteration comprises the introduction of a heterologous polynucleotide into the genome of the bacterial cell. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

Any bacteria of interest can be used in the methods and compositions described herein. In specific embodiments, the bacterium comprises a probiotic bacterium. The term "probiotic" as used herein refers to "live microorganisms, which when administered in adequate amounts confer a health benefit on a host (FAO 2001: see the website at isapp.net/docs/ProbioticDefinition.pdf) or at least one organism that contributes to the health and balance of the intestinal tract of a subject. In specific embodiments, it is also referred to as "friendly", "beneficial", or "good" bacteria, which when ingested by a subject assists in the maintenance of a healthy intestinal tract and assists in partially or completely alleviating one or more symptoms of an illness and/or disease. As used herein, "probiotic properties" comprises enhanced gut function and stability; improved protection against infectious and non-infectious diseases; immune system modulation; alleviated lactose intolerance; improved digestion and nutrient absorption; reduced blood cholesterol; reduced allergy risk; and reduced risk of urinary tract infections. In some embodiments, probiotic properties comprise an increase in anti-inflammatory cytokine production in the subject receiving the probiotic bacterium, a decrease in pro-inflammatory cytokine production in the subject receiving the probiotic bacterium, or an increase in the ratio of anti-inflammatory to pro-inflammatory cytokine production in the subject receiving the probiotic bacterium.

In some embodiments, the bacteria described herein have been modified to enhance one or more than one probiotic property. For example, in some embodiments, bacteria are provided having been modified to increase adhesion to the gastrointestinal epithelium and having been further modified to decrease the display of LTA on the cell surface. In other embodiments, bacteria are provided having been modified to increase resistance to acid or bile and having further been modified to decrease the display of LTA on the cell surface.

In other embodiments, the bacteria are lactic acid bacteria. As used herein, "lactic acid bacteria" is intended bacteria from a genus selected from the following: *Aerococcus, Carnobacterium, Enterococcus, Lactococcus, Lactobacillus, Leuconostoc, Oenococcus, Pediococcus, Streptococcus, Melissococcus, Alloiococcus, Dolosigranulum, Lactosphaera, Tetragenococcus, Vagococcus*, and *Weissella* (Holzapfel et al. (2001) *Am. J. Clin. Nutr.* 73:365 S-373S; Sneath, ed. (1986) *Bergey's Manual of Systematic Bacteriology Vol* 2, Lippincott, Williams and Wilkins, Hagerstown, Md.).

In still other embodiments, *Lactobacillus* is used. By "*Lactobacillus*" is meant any bacteria from the genus *Lactobacillus*, including but not limited to *L. casei, L. paracasei, L. reuteri, L. rhamnosus, L. johnsonni, L. gasseri, L. acidophilus, L. plantarum, L. fermentum, L. salivarius, L. bulgaricus*, and numerous other species outlined by Wood et al. (Holzapfel and Wood, eds. (1995) *The Genera of Lactic Acid Bacteria, Vol.* 2., Springer, N.Y.). In a specific embodiment, the bacterium is *L. acidophilus* NCFM.

The production of bacteria with a decreased display of LTA, the preparation of starter cultures of such bacteria, and methods of fermenting substrates, particularly food substrates such as milk, may be carried out in accordance with known techniques, including but not limited to those described in Mäyrä-Mäkinen and Bigret (1993) *Lactic Acid Bacteria*. Salminen and vonWright eds. Marcel Dekker, Inc. New York. 65-96.; Sandine (1996) *Dairy Starter Cultures* Cogan and Accolas eds. VCH Publishers, New York. 191-206; Gilliland (1985) *Bacterial Starter Cultures for Food.* CRC Press, Boca Raton, Fla.

Bacterial cells described herein can be cultured in suitable media, as described generally in Sambrook et al. (1989) *Molecular Cloning, A Laboratory Manual* (2d ed., Cold Spring Harbor Laboratory Press, Cold Spring Harbor, N.Y.).

In some embodiments, bacterial strains described herein are biologically pure cultures of a bacterium comprising at least one genetic alteration resulting in decreased display of LTA on the cell surface as described herein. In further embodiments, the bacterium comprises one or several nucleotide additions, deletions and/or substitutions. These strains may include but are not limited to: *Lactobacillus acidophilus, L. gasseri, L. johnsonii*, or *L. plantarum*. By "biologically pure" is intended 90%, 95%, 96%, 97%, 98%, 99%, or 100% free of other bacterial cells. In other embodiments, bacterial strains described herein are found in combination with other bacterial strains to produce mixed cultures.

A "control" or "control cell" or "control bacteria" provides a reference point for measuring changes in phenotype of the recombinant bacterial cells. A control bacteria may comprise, for example: (a) a wild-type bacterium, i.e., of the same genotype as the starting material for the genetic alteration which resulted in the subject bacterium; or (b) a bacterium of the same genotype as the starting material but which has been transformed with a null construct (i.e. with a construct which has no known effect on the trait of interest, such as a construct comprising a marker gene).

LTA-Related Polypeptides and Polynucleotides

The recombinant bacteria having a decreased display of LTA on the cell surface have been altered such that the level of activity of at least one LTA-related polynucleotide or polypeptide has been modulated (i.e. increased or decreased). As used herein, the terms "LTA" refers to lipoteichoic acid, a macroamphiphilic molecule with a glycolipid anchored in the membrane and poly(glycerophosphate) (Gro-P) chain extending into the wall. In some embodiments, the terms "LTA" or "lipoteichoic acid" includes wall teichoic acids (WTA), a teichoic acid covalently linked to the peptidoglycan layer of the cell wall. Biosynthesis of LTA begins with the transfer of carbohydrate units via glycosyltransferase to form a glycolipid anchored to the membrane on the inside of the cell. The glycolipid is transported out of the cell via a membrane protein and anchored to the cell membrane outside of the cell. Finally, phosphoglycerol transferase transports glycerophosphate (Gro-P) units to the anchored glycolipid to form elongated LTA (FIG. 1). Thus, LTA-related polynucleotides and polypeptides of the invention are understood to encompass those polynucleotides and polypeptides involved with the production, composition, transport, assembly, and display of LTA on the cell surface. In some embodiments, the display of LTA on the bacterial surface is decreased in order to modulate the inflammatory response in a subject administered the bacterium.

Fragments and variants of these LTA-related sequences can also be used to practice the methods described herein. As used herein, the terms "gene" and "recombinant gene" refer to nucleic acid molecules comprising an open reading frame, particularly those encoding proteins involved in the production, assembly, or display of LTA. In one embodiment, LTA-related polynucleotides and polypeptides comprise SEQ ID NOS: 1 and 2, or an active fragment or variant thereof. In further embodiments, the LTA-related polynucleotides and polypeptides comprise SEQ ID NOS: 3-16 or active fragments or variants thereof.

An LTA-related polynucleotide comprises both the coding sequence encoding the LTA-related protein, but also regulatory sequences such as the promoter. An LTA-related polynucleotide can further comprise sites essential for correct translation of LTA-related mRNA, such as the ribosomal binding site.

Isolated polypeptides and proteins associated with LTA, the cell wall, cell membrane, cell surface, or that are secreted, and variants and fragments thereof, are encompassed. For purposes of the present invention, the terms "protein" and "polypeptide" are used interchangeably.

The term "expression", as used herein, refers to the transcription of sense (mRNA) or antisense RNA derived from the nucleic acid fragment of the invention. Expression may also refer to translation of mRNA into a polypeptide.

Decreasing the Display of LTA

Methods and compositions are provided which modulate the level of expression (concentration and/or activity) of a target LTA-related polynucleotide. As used herein, a "target sequence" comprises any sequence that one desires to modulate the level of expression. The target sequence includes sequences which both encode and do not encode polypeptides. A functional LTA-related polynucleotide or polypeptide is understood to encode proteins, sequences, or RNA responsible for the production, assembly, transport, or display of LTA on the surface of a bacterium. Thus, a LTA-related polynucleotide or polypeptide whose expression has been decreased would result in a bacterium having a decreased surface display of LTA when compared to its wild-type counterpart. In some embodiments, a bacterium with decreased surface display of LTA can reduce or prevent the inflammatory response of a subject suffering from an IBD, such as colitis.

By "reduces" or "reducing" the expression level of a polynucleotide or a polypeptide encoded thereby is intended to mean, the polynucleotide or polypeptide level of the target sequence is statistically lower than the polynucleotide level or polypeptide level of the same target sequence in an appropriate control. In particular embodiments, reducing the polynucleotide level and/or the polypeptide level of the target sequence according to the presently disclosed subject matter results in at least a 95% decrease, at least a 90% decrease, at least a 80% decrease, at least a 70% decrease, at least a 60% decrease, at least a 50% decrease, at least a 40% decrease, at least a 30% decrease, at least a 20% decrease, at least a 10% decrease, or at least a 5% decrease of the polynucleotide level, or the level of the polypeptide encoded thereby, of the same target sequence in an appropriate control. In other embodiments, reducing the polynucleotide level and/or the polypeptide level of the target sequence results in a decrease of about 3%-15%, 10%-25%, 20% to 35%, 30% to 45%, 40%-55%, 50%-65%, 60%-75%, 70%-90%, 70% to 80%, 70%-85%, 80%-95%, 90%-100% in the polynucleotide level, or the level of the polypeptide encoded thereby, when compared to an appropriate control. Methods to assay for the level of the RNA transcript, the level of the encoded polypeptide, or the activity of the polynucleotide or polypeptide are discussed elsewhere herein.

In some embodiments, increasing the level of a polynucleotide or polypeptide of interest can decrease the display of LTA on the cell surface. By "increases" or "increasing" the expression level of a polynucleotide or a polypeptide encoded thereby is intended to mean, the polynucleotide or polypeptide level of the target sequence is statistically greater than the polynucleotide level or polypeptide level of the same target sequence in an appropriate control. In particular embodiments, increasing the polynucleotide level and/or the polypeptide level of the target sequence according to the presently disclosed subject matter results in at least a 95% increase, at least a 90% increase, at least a 80% increase, at least a 70% increase, at least a 60% increase, at least a 50% increase, at least a 40% increase, at least a 30% increase, at least a 20% increase, at least a 10% increase, or at least a 5% increase of the polynucleotide level, or the level of the polypeptide encoded thereby, of the same target sequence in an appropriate control. In other embodiments, increasing the polynucleotide level and/or the polypeptide level of the target sequence results in an increase of about 3%-15%, 10%-25%, 20% to 35%, 30% to 45%, 40%-55%, 50%-65%, 60%-75%, 70%-90%, 70% to 80%, 70%-85%, 80%-95%, 90%-100% in the polynucleotide level, or the level of the polypeptide encoded thereby, when compared to an appropriate control. Methods to assay for the level of the RNA transcript, the level of the encoded polypeptide, or the activity of the polynucleotide or polypeptide are discussed elsewhere herein.

Recombinant organisms having a decrease in the display of LTA on the surface may be constructed using a variety of techniques. In the present invention, the expression of polynucleotides or polypeptides encoding at least one of the enzymes of one of the LTA assembly pathways, for example, phosphoglycerol transferase or glycosyltransferase may be decreased, as described herein.

In one embodiment, the level of an LTA-related polypeptide comprising a phosphoglycerol transferase is decreased. In certain embodiments, the expression of the phosphoglycerol transferase set forth in SEQ ID NO: 2, or an active fragment or variant thereof, is decreased. Phosphoglycerol transferase is a polypeptide involved the transfer of Gro-P units to a glycolipid, thereby extending the LTA chain. Various phosphoglycerol transferase polypeptides and genes encoding the polypeptides are known. As used herein, phosphoglycerol transferase encompasses LTA synthase (LtaS), glycerol phosphotransferase, glycerophosphotransferase, and any other polypeptide that catalyzes the transfer of Gro-P units for the formation of the polyglycerolphosphate backbone of LTA. Phosphoglycerol transferase is a member of the alkaline phosphatase superfamily (MdoB [COG1368] Phosphoglycerol transferase). See, for example, NCBI Accession No. NZ_ACGX01000068.1 and NC_010609.1. Each of these references is herein incorporated by reference.

In another embodiment, the LTA-related polypeptide can comprise a glycosyltransferase. In this embodiment, the level of glycosyltransferase is decreased using any of the methods to decrease the level of a polynucleotide or polypeptide described elsewhere herein. In one embodiment, the expression of the glycosyltransferase set forth in SEQ ID NO: 4 or 6, or an active fragment or variant thereof, is decreased. Glycosyltransferase is a polypeptide involved in the synthesis of glycolipids and lipid anchors for LTA. The glycosyltransferase polypeptides and genes encoding the polypeptides are known. As used herein, the term glycosyltransferase refers to any polypeptide that catalyzes the synthesis of glycolipids or lipid anchors for LTA including, for example, YgpP, Ugt, BgsA, IagA, LafA, or LafB. Glycosyltransferase is a member of the Glycosyltransferase_GTB_type super family [cl10013]. Various glycosyltransferases are known. See, for example, NCBI Accession No. NC_010609.1 and EF138835.1. Each of these references is herein incorporated by reference.

The quality and level of D-Ala substitution on teichoic acids can decrease the display of LTA on the cell surface. The synthesis of D-alanyl-LTA requires four proteins that are encoded by the dlt operon, DltA, DltB, DltC, or DltD. Thus, in some embodiments, the LTA-related polynucleotide or polypeptide can comprise the polynucleotide or polypeptide set forth in the Dlt operon, including SEQ ID NOS: 9-16. Thus, in another embodiment, the level of DltA, DltB, DltC, or DltD is decreased using any of the methods to decrease the level of a LTA-related polynucleotide or polypeptide described elsewhere herein. Various members of the dlt operon are known. See, for example, NCBI Accession No. AAF09201 (DltA); NCBI Accession No. AAB17658.1 (DltB); NCBI Accession No. CAR86674.1 (DltC); and NCBI Accession No. CAQ65981.1 (DltD). Each of these references is herein incorporated by reference. The structure of LTA can be measured by NMR and MS using known techniques. See, for example, Morath S, Geyer A, & Hartung T (2001) *J Exp Med* 193(3):393-397.

A decrease in the expression of LTA-related polynucleotides or polypeptides can be achieved by a variety of techniques well known in the art. For example, gene expression can be decreased by a mutation. The mutation can be an insertion, a deletion, a substitution or a combination thereof, provided that the mutation leads to a decrease in the expression of a functional LTA-related protein or results in a decrease in expression of an LTA-related polynucleotide such that the display of LTA on the surface of the cell is decreased. Bacteria with decreased display of LTA can be used to reduce the inflammatory response of a subject, thereby treating or preventing inflammatory bowel diseases, such as colitis.

Recombinant DNA technology can be used to introduce a mutation into a specific site on the chromosome. Such a mutation may be an insertion, a deletion, a replacement of one nucleotide by another one or a combination thereof, as long as the mutated gene leads to a decrease in the expression of a functional LTA-related protein or results in a decrease in express of an LTA-related gene such that the display of LTA on the surface of the cell is decreased. Such a mutation can be made by deletion of a number of base pairs. In one embodiment, the deletion of one single base pair could render a LTA related protein non-functional, thereby decreasing the display of LTA on the bacterial surface, since as a result of such a mutation, the other base pairs are no longer in the correct reading frame. In other embodiments, multiple base pairs are removed e.g. 100 base pairs. In still other embodiments, the length of the entire LTA-related gene is deleted. Mutations introducing a stop-codon in the open reading frame, or mutations causing a frame-shift in the open reading frame could be used to reduce the expression of a LTA-related gene.

Other techniques for decreasing the expression of a LTA-related gene in order to decrease the display of LTA are well-known in the art. For example, techniques may include modification of the gene sequence by site-directed mutagenesis, restriction enzyme digestion followed by re-ligation, PCR-based mutagenesis techniques, allelic exchange, allelic replacement, RNA interference, or post-translational modification. Standard recombinant DNA techniques such as cloning the LTA-related gene into a plasmid, digestion of the gene with a restriction enzyme, followed by endonuclease treatment, re-ligation, and homologous recombination are all known in the art and described in Maniatis/Sambrook (Sambrook, J. et al. Molecular cloning: a laboratory manual. ISBN 0-87969-309-6). Site-directed mutations can be made by means of in vitro site directed mutagenesis using the TRANSFORMER kit sold by Clontech. PCR-techniques are extensively described in (Dieffenbach & Dreksler; PCR primers, a laboratory manual. ISBN 0-87969-447-3 and ISBN 0-87969-447-5).

Mutations in the coding regions and also mutations in those sequences essential for correct transcription and translation including regulatory sequences, such as promoters, are considered to fall within the scope of the invention.

In certain embodiments, the recombinant bacterium is modified by site-directed mutagenesis to have decreased display of LTA on the surface. In other embodiments, the bacterium having decreased display of LTA is isolated from a bacterial population. It will be understood that the term isolated as used herein, refers to a bacterium which is separated from its natural environment. This may be, for example, by purification from a mixed bacterial population or an environmental sample. An isolated bacterium is substantially free of other bacterial species and components of the natural environment of the bacterium. A bacterium that is substantially free of other bacterial species and components of the natural environment includes bacterial preparations having less than about 30%, 20%, 10%, 5%, or 1% of contaminating bacterial species or components of the natural environment.

Assays

Assays to detect expression of the disclosed polypeptides and/or nucleic acid molecules can include the detection and/or quantitation of LTA. Methods for the detection of LTA are described elsewhere herein. A decrease in the display of LTA on the surface of a bacterial cell can result in an increase in the anti-inflammatory response or a decrease in the pro-inflammatory response of host cells exposed to the bacterium. Assays to measure anti-inflammatory or pro-inflammatory response, for example, can also be used to evaluate the expression of LTA-related polypeptides of the present invention. Methods to measure inflammatory response are also described elsewhere herein.

Fragments and Variants

Depending on the context, "fragment" refers to a portion of the amino acid sequence of a polypeptide or protein, or polynucleotide encoding a portion of the amino acid sequence of a polypeptide or protein. Fragments may retain the activity of the original protein and hence, such "active" fragments include, for example, fragments of an LTA-related protein, such as a fragment of SEQ ID NO: 2 that retains phosphoglycerol transferase activity. A fragment of a LTA-related nucleotide sequence, such as a fragment of SEQ ID NO: 1 that encodes an active phosphoglycerol transferase, may encode a protein fragment that is biologically active. Additionally, fragments of LTA-related proteins include fragments of SEQ ID NOS: 2, 4, 6, 8, 10, 12, 14 and 16. A biologically active nucleotide fragment can be prepared by isolating a portion of an LTA-related polynucleotide or polypeptide, expressing the encoded portion of the LTA-related protein, and assessing the activity of the encoded portion of the LTA-related protein. In other embodiments, a fragment of nucleotide sequence of a LTA-related protein need not encode a biologically active polypeptide, but rather could comprise a polynucleotide which, when expressed, suppresses the expression of the target LTA-related polypeptide (i.e. sense, antisense, miRNA, or siRNA suppression). Fragments of LTA-related polynucleotides include fragments of SEQ ID NOS: 1, 3, 5, 7, 9, 11, 13 and 15. Fragments of LTA-related nucleic acid molecules comprise at least about 15, 20, 50, 75, 100, 150, 200, 250, 300, 350, 400, 450, 500, 550, 600, 650, 700, 750, 800, 850, 900, 950, 1000 nucleotides or up to the total number of nucleotides present in a full-length LTA-related nucleotide sequence as disclosed herein.

Fragments of amino acid sequences include peptides comprising amino acid sequences sufficiently identical to or derived from the amino acid sequence of a LTA-related protein, or a partial-length protein and exhibiting at least one activity of a LTA-related protein (i.e. modulate the level of LTA displayed on the cell surface), but which include fewer amino acids than the full-length LTA-related proteins disclosed herein. A biologically active portion of a LTA-related protein can be a polypeptide that is, for example, 10, 25, 50, 100, 150, 200 contiguous amino acids in length, or up to the total number of amino acids present in a full-length LTA-related protein of the current invention (i.e., of SEQ ID NO: 2, 4, 6, 8, 10, 12, 14 or 16). Such biologically active portions can be prepared by recombinant techniques and evaluated for one or more of the functional activities of a native LTA-related protein, such as phosphoglycerol transferase activity. As used here, a fragment comprises at least 5 contiguous amino acids of SEQ ID NOS: 2, 4, 6, 8, 10, 12, 14 or 16. The invention encompasses other fragments, however, such as any fragment in the protein greater than 6, 7, 8, or 9 amino acids.

In some embodiments recombinant bacteria are provided which have been modified to reduce the expression of variants of the nucleotide and amino acid sequences provided elsewhere herein. By "variant" is intended a sufficiently identical sequence. Accordingly, the invention encompasses bacteria, modified to reduce the expression of nucleic acid molecules that are sufficiently identical to the nucleotide sequences encoding LTA-related proteins in SEQ ID NOS: 2, 4, 6, 8, 10, 12, 14 or 16, or nucleic acid molecules that comprise the nucleotide sequence of SEQ ID NOS: 1, 3, 5, 7, 9, 11, 13 or 15, or a complement thereof. Variant polynucleotides further include sequences comprising one or several additions, deletions, or substitutions. Variants also include variant polypeptides encoded by the nucleotide sequences of the present invention. In addition, polypeptides of the current invention have an amino acid sequence that is sufficiently identical to an amino acid sequence put forth in SEQ ID NOS: 2, 4, 6, 8, 10, 12, 14 or 16. By "sufficiently identical" is intended that one amino acid sequence or nucleotide sequence contains a sufficient or minimal number of equivalent or identical amino acid residues or nucleotides as compared to a second amino acid sequence or nucleotide sequence, thus providing a common structural domain and/or indicating a common functional activity, such as LTA-related biological activity. Conservative variants include those nucleotide sequences that differ due to the degeneracy of the genetic code.

In general, amino acid sequences or nucleotide sequences that have at least about 45%, 55%, or 65% identity, preferably at least about 70% or 75% identity, more preferably at least about 80%, 85% or 90%, most preferably at least about 91%, 92%, 93%, 94%, 95%, 95%, 96%, 97%, 98%, 99%, or 99.5% sequence identity to any of the amino acid sequences of SEQ ID NOS: 2, 4, 6, 8, 10, 12, 14 or 16 or any of the nucleotide sequences of SEQ ID NOS: 1, 3, 5, 7, 9, 11, 13 or 15, respectively, are defined herein as sufficiently identical. Variant proteins encompassed by the present invention are biologically active, that is they retain the desired LTA-related biological activity of the native protein, such as phosphoglycerol transferase activity of SEQ ID NO: 2. See, for example, Varcamonti et al. (2003) *Appl. Environ. Microbiol.* 69: 1287-1289. A biologically active variant of a protein may differ from that protein by as few as 1-15 amino acid residues, as few as 1-10, such as 6-10, as few as 5, as few as 4, 3, 2, or even 1 amino acid residue.

LTA-related polypeptides may be altered in various ways including amino acid substitutions, deletions, truncations, and insertions. Methods for mutagenesis and polynucleotide alterations are well known in the art. See, for example, Kunkel (1985) *Proc. Natl. Acad. Sci. USA* 82: 488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made. One skilled in the art will appreciate that the activity of a LTA-related polypeptide disclosed herein can be evaluated by routine screening assays, such as those described elsewhere herein.

As used herein, a "native sequence" polypeptide comprises a polypeptide having the same amino acid sequence as the corresponding polypeptide derived from nature. Such native sequence polypeptides can be isolated from nature or can be produced by recombinant and/or synthetic means. The term "native sequence" specifically encompasses naturally-occurring truncated, soluble or secreted forms, naturally-occurring variant forms, and naturally-occurring allelic variants of the polypeptide.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Methods of Treatment and Prevention

Methods are provided for decreasing inflammation in a subject comprising administration of a recombinant bacterium described elsewhere herein. In some embodiments, administration of a recombinant bacterium with a decreased display of LTA can ameliorate the symptoms of IBD, such as colitis, in a subject. In other embodiments, administration of a recombinant bacterium with decreased display of LTA can prevent the onset of IBD, such as colitis, in a subject. In some embodiments, a recombinant bacterium with decreased expression of an LTA-related protein, including, for example, phosphoglycerol transferase, including, for example, decrease in expression of SEQ ID NO:1 or active fragments or variants thereof, has a decreased display of LTA on the cell surface and can ameliorate the symptoms of established colitis and prevent the onset of colitis. See Example 1 below. In some embodiments, methods for treating and/or preventing inflammation locally in the gastrointestinal tract, treating and/or preventing inflammatory disorders of the gastrointestinal tract, as well as treating pain locally in the intestines, in a subject are provided.

"Treatment" is herein defined as curing, healing, alleviating, relieving, altering, remedying, ameliorating, improving, or affecting the condition or the symptoms of a subject with a gastrointestinal disorder. The subject to be treated can be suffering from or at risk of developing a gastrointestinal disorder, including, for example, be suffering from an inflammatory bowel disease or be at risk of developing an inflammatory bowel disease.

Administration of the recombinant bacterium can be for either a prophylactic or therapeutic purpose. By "preventing" is intended that the recombinant bacterium is provided prophylactically, i.e., the bacterium is provided in advance of any symptom. The prophylactic administration of the recombinant bacterium serves to prevent or attenuate any subsequent symptom. When provided therapeutically, the bacterium is provided at (or shortly after) the onset of a symptom. The therapeutic administration of the substance serves to attenuate any actual symptom.

By "subject" is intended animals. In specific embodiments, subjects are mammals, e.g., primates or humans. In other embodiments, subjects include domestic animals, such as a feline or canine, or agricultural animals, such as a ruminant, horse, swine, poultry, or sheep. In specific embodiments, the subject undergoing treatment with the pharmaceutical formulations of the invention is a human. In some embodiments, the human undergoing treatment can be a newborn, infant, toddler, preadolescent, adolescent or adult. The subjects of the invention may be suffering from the symptoms of a gastrointestinal disorder or may be at risk for a gastrointestinal disorder (e.g. a subject that has undergone antibiotic treatment).

Gastrointestinal Disorders

The methods and compositions of the invention relate to treatment of inflammatory gastrointestinal disorders. As used herein, the term "inflammatory gastrointestinal disorder" or "gastrointestinal disorder" or "inflammatory disorder of the gastrointestinal tract" refers to a disease of the gastrointestinal tract or bowel that is mediated by the immune system or cells of the immune system. Inflammatory gastrointestinal disorders include, for example, inflammatory bowel diseases (IBD) such as Crohn's disease and ulcerative colitis, lymphocytic colitis, microscopic colitis, collagenous colitis, autoimmune enteropathy, allergic gastrointestinal disease and eosinophilic gastrointestinal disease, as well as diarrhea, bloating, flatulence, abdominal cramping, abdominal pain, or constipation. In certain embodiments, the methods of the invention relate to the treatment or prevention of obesity, or the symptoms of obesity including, IBD, diarrhea, bloating, flatulence, abdominal cramping, abdominal pain, or constipation. See, for example, Kadooka Y, et. al. (2010) *Eur J Clin Nutr.* 64(6):636-43, herein incorporated by reference.

In some embodiments, the decrease in inflammation may include stimulation of intestinal integrity; reduction of intestinal permeability; improvement of mucin synthesis, secretion, and/or quality; improvement of the maturation and differentiation of the intestinal epithelium; improvement of nutrient absorption; increase of the production of soluble factors that transfer antimicrobial activity; stimulation of, improvement of, or support of resistance to infection; support of cellular or humoral responses against viral or bacterial infection; increased cytotoxicity (both anti-viral and anti-tumor); support of systemic and/or mucosal vaccination responses; increase or support of cellular and/or humoral immunity; increase or support of natural immunity (including neutrophils, phagocytes, macrophages, and natural killer cell activity); increase or support of adaptive T and B cell immunity; stimulation of a helper T cell 1 (Th1) cytokine pattern (increased IL-1, IL-2, IFN-gamma, IL-12, TNF-alpha; human leukocyte antigen-Dr (HLA-Dr) expression); suppression of inflammation or production of systemic and mucosal inflammatory mediators (including cytokines and/or chemokines); reduction of sensitization by reducing total and/or allergen-specific IgE; reduction of the production of allergic cytokines; reduction of a Th2 supporting immunoglobulin profile; and combinations thereof.

As used herein, the term "anti-inflammatory cytokine" refers to a naturally occurring or recombinant protein, analog thereof or fragment thereof that elicits an anti-inflammatory response in a cell that has a receptor for that cytokine Anti-inflammatory cytokines of the invention can be immunoregulatory molecules that control the proinflammatory cytokine response. Anti-inflammatory cytokines of the invention include interleukin (IL)-1 receptor antagonist, IL-4, IL-10, IL-11, and IL-13, IL-16, IFN-alpha, TGF-beta, G-CSF.

As used herein, the term "proinflammatory cytokine" refers to an immunoregulatory cytokine that favors inflammation. Proinflammatory cytokines of the invention include IL1-alpha, IL1-beta, TNF-alpha, IL-2, IL-3, IL-6, IL-7, IL-9, IL-12, IL-17, IL-18, TNF-alpha, LT, LIF, Oncostatin, or IFN-alpha, IFN-beta, IFN-gamma.

In some embodiments, administration of the recombinant bacterium results in an increase in anti-inflammatory cytokine production. As used herein, an "increase in" or "increasing" anti-inflammatory cytokine production comprises any statistically significant increase the anti-inflammatory cytokine level when compared to an appropriate control. Such increases can include, for example, at least a 5%, 10%, 20%, 30%, 40%, 50%, 60%, 70%, 80%, 90%, 100%, 150%, 200% or greater increase in the anti-inflammatory cytokine level. Such increases can also include, for example, at least about a 3%-15%, 10%-25%, 20% to 35%, 30% to 45%, 40%-55%, 50%-65%, 60%-75%, 70%-85%, 80%-95%, 90%-105%, 100%-115%, 105%-120%, 115%-130%, 125%-150%, 140%-160%, 155%-500% or greater increase in the anti-inflammatory cytokine level. Methods to assay for the level of anti-inflammatory cytokine level, are known. See, for example, Leng S., et al. (2008) *J Gerontol A Biol Sci Med Sci* 63(8): 879-884. Methods to assay for the production of anti-inflammatory cytokines include multiplex bead assay, ELISPOT and flow cytometry. See, for example, Maecker et al. (2005) *BMC Immunology* 6:13.

Methods and compositions also include those which decrease proinflammatory cytokine production, which may decrease or prevent an inflammatory response. As used herein, a decrease in the level of pro-inflammatory cytokine production comprises any statistically significant decrease in the level of pro-inflammatory cytokine production in a subject when compared to an appropriate control. Such decreases can include, for example, at least a 5%, 10%, 20%, 30%, 40%, 50%, 60%, 70%, 80%, 90%, or 100% decrease in the level of proinflammatory cytokines Methods to assay for cytokine levels are known and include, for example Leng S., et al. (2008) *J Gerontol A Biol Sci Med Sci* 63(8): 879-884. Methods to assay for the production of pro-inflammatory cytokines include multiplex bead assay, ELISPOT and flow cytometry. See, for example, Maecker et al. (2005) *BMC Immunology* 6:13.

Inflammatory cytokine production can also be measured by assaying the ratio of anti-inflammatory cytokine production to proinflammatory cytokine production. In specific aspects, the ratio of anti-inflammatory cytokine production to proinflammatory cytokine production is increased by about 1, 2, 3, 4, 5, 6, 7, 8, 9, 10, 20, 30, 40, 50, 60, 70, 80, 90, 100, 300, 600, 900, 1000 fold or greater when compared to an appropriate control. In other aspects, the ratio of anti-inflammatory cytokine production to pro-inflammatory cytokine production is increased by about 1 to 5 fold, about 5 to 10 fold, about 10 to 20 fold, about 20 to 30 fold, about 30 to 40 fold, about 40 fold to 60 fold, about 60 fold to 80 fold, about 80 fold to about 100 fold, about 100 to 200 fold, about 200 fold to 300 fold, about 300 to 400 fold, about 400 to about 500 fold, about 500 to about 500 fold, about 500 fold to about 700 fold, about 700 fold to about 800 fold, about 800 fold to about 1000 fold or greater when compared to an appropriate control. Methods to determine the ratio of anti-inflammatory cytokine production to pro-inflammatory cytokine production can be found, for example, Leng S., et al. (2008) *J Gerontol A Biol Sci Med Sci* 63(8): 879-884. Methods to assay for the production of cytokines include multiplex bead assay, ELISPOT and flow cytometry. See, for example, Maecker et al. (2005) *BMC Immunology* 6:13.

Inflammatory Disorders

In some embodiments, by decreasing inflammation using the compositions and methods described elsewhere herein, immune and inflammatory disorders can be treated or prevented. For example, disorders that could be treated or prevented by the methods and compositions described herein include, but are not limited to: arthritis (rheumatoid arthritis, juvenile rheumatoid arthritis, osteoarthritis, psoriatic arthritis), psoriasis, dermatitis including atopic dermatitis; chronic autoimmune urticaria, polymyositis/dermatomyositis, toxic epidermal necrolysis, systemic scleroderma and sclerosis, respiratory distress syndrome, adult respiratory distress syndrome (ARDS), meningitis, allergic rhinitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), lupus (including nephritis, non-renal, discoid, alopecia), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, etc), graft versus host disease (GVHD), pemphigoid bullous, pemphigus (all including vulgaris, foliaceus), autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, Lymphoid interstitial pneumonitis (HIV), bronchiolitis obliterans (non-transplant) vs NSIP, Guillain-Barre' Syndrome, Large Vessel Vasculitis (including Polymyalgia Rheumatica and Giant Cell (Takayasu's) Arteritis), Medium Vessel Vasculitis (including Kawasaki's Disease and Polyarteritis Nodosa), ankylosing spondylitis, Berger's Disease (IgA nephropathy), Rapidly Progressive Glomerulonephritis, Primary biliary cirrhosis, Celiac sprue (gluten enteropathy), Cryoglobulinemia, ALS, or coronary artery disease.

In specific embodiments, by decreasing inflammation in a subject, a disorder of the heart is treated or prevented. As used herein a disorder of the heart includes but is not limited to: heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Pharmaceutical Composition

In some embodiments, bacterial strains having a decrease in the display of LTA are administered to a subject in the form of a nutraceutical composition such as a nutritional supplement and/or food additive. In specific embodiments, the pharmaceutical composition comprises a recombinant bacterium that has been modified to decrease the expression of a polynucleotide or polypeptide encoding a phosphoglycerol transferase (such as the polynucleotide and polypeptide set forth in SEQ ID NO: 1 and 2). In other embodiments, the extracts are administered to a subject in the form of a pharmaceutical composition. The administration may comprise a single dose or multiple dose administration, as described elsewhere herein.

The pharmaceutical composition may be a liquid formulation or a solid formulation. When the pharmaceutical composition is a solid formulation it may be formulated as a tablet, a sucking tablet, a chewing tablet, a chewing gum, a capsule, a sachet, a powder, a granule, a coated particle, a coated tablet, an enterocoated tablet, an enterocoated capsule, a melting strip or a film. When the pharmaceutical composition is a liquid formulation it may be formulated as an oral solution, a suspension, an emulsion or syrup. Said composition may further comprise a carrier material independently selected from, but not limited to, the group consisting of lactic acid fermented foods, fermented dairy products, resistant starch, dietary fibers, carbohydrates, proteins, and glycosylated proteins.

As used herein, the term "pharmaceutical composition" could be formulated as a food composition, a dietary supplement, a functional food, a medical food or a nutritional product as long as the required effect is achieved, i.e. treatment or prevention of an inflammatory disorder of the gastrointestinal tract. Said food composition may be chosen from the group consisting of beverages, yogurts, juices, ice creams, breads, biscuits, crackers, cereals, health bars, spreads and nutritional products. The food composition may further comprise a carrier material, wherein said carrier material is chosen from the group consisting of lactic acid fermented foods, fermented dairy products, resistant starch, dietary fibers, carbohydrates, proteins and glycosylated proteins.

The pharmaceutical composition according to the invention, used according to the invention or produced according to the invention may also comprise other substances, such as an inert vehicle, or pharmaceutical acceptable adjuvants, carriers, preservatives etc., which are well known.

The present disclosure also includes combinations of the recombinant bacteria with one another, and/or with one or more other agents useful in the treatment of an inflammatory disorder of the gastrointestinal tract. For example, bacteria of the invention may be administered in combination with effective doses of conventional anti-inflammatory agents for treatment of inflammatory disorders of the gastrointestinal tract, such as prednisone, mesalamine, azathioprine, TNF inhibitors, methotrexate, or 6-mercaptopurine. The term "administration in combination" refers to both concurrent and sequential administration of the active agents. The combination therapies are of course not limited to the agents provided herein, but include any composition for the treatment of inflammatory disorders.

Therapeutically Effective Amount

By "therapeutically effective dose," "therapeutically effective amount," or "effective amount" is intended an amount of the recombinant bacterium having a decreased display of LTA that, when administered to a subject, decreases the inflammatory response, or prevents an inflammatory response from increasing. "Positive therapeutic response" refers to, for example, improving the condition of at least one of the symptoms of an inflammatory gastrointestinal disorder.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual. Generally, the dosage of recombinant bacteria will vary depending upon such factors as the patient's age, weight, height, sex, general medical condition and previous medical history. In specific embodiments, it may be desirable to administer the bacterium in the range of about $10^4$ to about $10^{12}$ CFU, $10^5$ to $10^{11}$ CFU, $10^6$ to $10^{10}$ CFU, $10^8$ to $10^{10}$ CFU or $10^8$ to $10^{12}$ CFU.

In some embodiments of the invention, the method comprises administration of multiple doses of the bacterium. The method may comprise administration of 1, 2, 3, 4, 5, 6, 7, 8, 9, 10, 15, 20, 25, 30, 35, 40, or more therapeutically effective doses of a composition comprising the bacterium as described herein. In some embodiments, doses are administered over the course of 1 day, 2 days, 3 days, 4 days, 5 days, 6 days, 7 days, 10 days, 14 days, 21 days, 30 days, or more than 30 days. The frequency and duration of administration of multiple doses of the compositions is such as to reduce or prevent an inflammatory response and thereby treat or prevent a gastrointestinal disorder. Moreover, treatment of a subject with a therapeutically effective amount of the recombinant bacterium of the invention can include a single treatment or can include a series of treatments. It will also be appreciated that the effective dosage of a bacterium used for treatment may increase or decrease over the course of a particular treatment. Changes in dosage may result and become apparent from the results of diagnostic assays for detecting inflammation known in the art and described herein.

Deposits

Applicant made a deposit of *Lactobacillus acidophilus* NCK2025 with the American Type Culture Collection (ATCC), Manassas, Va. 20110 USA, ATCC Deposit No. PTA-11587 on Jan. 10, 2011. The bacterial culture deposited with the ATCC on Jan. 10, 2011 was taken from the deposit maintained by North Carolina State University, 100 Schaub Hall, Campus Box 7624, Raleigh, N.C., 27695 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. This deposit of *Lactobacillus acidophilus* NCK2025 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§1.801-1.809, including providing an indication of the viability of the sample upon deposit. Applicant has no authority to waive any restrictions imposed by law on the transfer of biological material or its transportation in commerce In light of the description provided above, the following embodiments are provided:

Numbered Embodiments

1. A recombinant or isolated bacterium having been genetically modified to decrease the display of lipoteichoic acid (LTA) on the surface of said bacterium.

2. The recombinant or isolated bacterium of embodiment 1, wherein said recombinant or isolated bacterium has been genetically modified to decrease the expression of a phosphoglycerol transferase.

3. The recombinant or isolated bacterium of embodiment 1 or 2, wherein said recombinant or isolated bacterium has been genetically modified to decrease the expression of a polynucleotide comprising the nucleotide sequence having at least 70%, 80%, 90%, 95%, 97%, 98%, or 99% sequence identity to the nucleic acid sequence as set forth in SEQ ID NO:1.

4. The recombinant or isolated bacterium of embodiment 1 or 2, wherein said recombinant or isolated bacterium has been genetically modified to decrease the expression of a polynucleotide comprising the nucleotide sequence as set forth in SEQ ID NO:1.

5. The recombinant or isolated bacterium of any one of the preceding embodiments, wherein said recombinant or isolated bacterium is a probiotic bacterium.

6. The recombinant or isolated bacterium of embodiment 5, wherein said probiotic bacterium is a lactic acid bacterium.

7. The recombinant or isolated bacterium of embodiment 6, wherein said lactic acid bacterium is a *Lactobacillus*.

8. The recombinant bacterium of embodiment 7, wherein said *Lactobacillus* is *Lactobacillus acidophilus*.

9. The recombinant or isolated bacterium of embodiment 8, wherein said genetic modification was performed on *Lactobacillus acidophilus* NCFM.

10. The recombinant or isolated bacterium of embodiment 8, wherein said *Lactobacillus acidophilus* is *Lactobacillus acidophilus* NCK2025, deposited under ATCC accession number PTA-11587.

11. A method of making a recombinant or isolated bacterium, said method comprising genetically modifying a bacterium to decrease the display of lipoteichoic acid (LTA) on the surface of said bacterium.

12. The method of embodiment 11, wherein said recombinant or isolated bacterium has been modified to decrease the expression of a phosphoglycerol transferase.

13. The method of embodiment 11 or 12, wherein said recombinant or isolated bacterium has been genetically modified to decrease the expression of a polynucleotide comprising a nucleotide sequence having at least 70%, 80%, 90%, 95%, 97%, 98% or 99% sequence identity to the nucleotide sequence as set forth in SEQ ID NO:1.

14. The method of any one of embodiments 11-13, wherein said recombinant bacterium is a probiotic bacterium.

15. The method of embodiment 14, wherein said probiotic bacterium is a lactic acid bacterium.

16. The method of embodiment 15, wherein said lactic acid bacterium is a *Lactobacillus*.

17. The method of embodiment 16, wherein said *Lactobacillus* is *Lactobacillus acidophilus*.

18. The method of embodiment 17, wherein said genetic modification was performed on *Lactobacillus acidophilus* NCFM.

19. The method of embodiment 17, wherein said *Lactobacillus acidophilus* is *Lactobacillus acidophilus* NCK2025, deposited under ATCC accession number PTA-11587.

20. The method of any one of embodiments 17 to 19, wherein said *Lactobacillus acidophilus* has been modified to decrease the expression of a polynucleotide comprising the nucleotide sequence as set forth in SEQ ID NO: 1.

21. A method of decreasing inflammation in a subject comprising, administering to said subject a therapeutically effective amount of the recombinant or isolated bacterium of any one of embodiments 1-10.

22. A method of treating or preventing an inflammatory disorder of the gastrointestinal tract of a subject comprising, administering to a subject a therapeutically effective amount of the recombinant or isolated bacterium according to any one of embodiments 1-10.

23. The method of any one of embodiments 21 or 22, wherein said subject is a animal.

24. The method of embodiment 23, wherein said subject is a mammal.

25. The method of embodiment 24, wherein said subject is a human.

26. The method of embodiment 23, wherein said subject is a domestic animal.

27. The method of embodiment 23, wherein said subject is an agricultural animal.

28. The method of any one of embodiments 21-27, wherein said subject has a gastrointestinal disorder.

29. The method of embodiment 28 wherein said gastrointestinal disorder is selected from the group consisting of: inflammatory bowel disease, Crohn's disease, irritable bowel syndrome, ulcerative colitis, obesity, diarrhea, bloating, flatulence, abdominal cramping, abdominal pain, constipation, and any combination thereof.

30. The method of any one of embodiments 21-29, wherein said bacterium increases the production of one or more anti-inflammatory cytokines in said subject.

31. The method of embodiment 30, wherein said anti-inflammatory cytokine is IL-10.

32. The method of any one of embodiments 21-31, wherein said bacterium decreases production of one or more pro-inflammatory cytokine in said subject.

33. The method of embodiment 32, wherein said pro-inflammatory cytokine is selected from the group consisting of: IL-12, IL-6, IFNγ, TNFα, and any combination thereof.

34. The method of any one of embodiments 21-33, wherein said therapeutically effective amount of the bacterium is about $10^8$ to $10^{12}$ CFU/day.

35. A pharmaceutical composition comprising the recombinant or isolated bacterium according to any one of embodiments 1-10.

36. The recombinant or isolated bacterium according to any one of embodiments 1-10 for use as a medicament.

37. The recombinant or isolated bacterium according to any one of embodiments 1-10 for use in treating or preventing an inflammatory disorder of the gastrointestinal tract of a subject, such as a subject according to any one of embodiments 23-27.

38. The recombinant or isolated bacterium for use according to embodiment 36 or 37, wherein said bacterium causes an increase in the anti-inflammatory cytokine production in said subject.

39. The recombinant or isolated bacterium according to embodiment 38 for use, wherein said anti-inflammatory cytokine is IL-10.

40. The recombinant or isolated bacterium for use according to any one of embodiments 36-39, wherein said bacterium decreases production of one or more pro-inflammatory cytokine in said subject.

41. The recombinant or isolated bacterium for use according to embodiment 40, wherein said pro-inflammatory cytokine is selected from the group consisting of: IL-12, IL-6, IFNγ, TNFα, and any combination thereof.

42. The recombinant or isolated bacterium for use according to any one of embodiments 36-41, wherein said bacterium is formulated to be administered to a subject in a therapeutically effective amount, wherein the therapeutically effective amount of the bacterium is about $10^8$ to $10^{12}$ CFU/day.

43. The recombinant or isolated bacterium for use according to any one of embodiments 36-42, wherein said gastrointestinal disorder is selected from the group consisting of: inflammatory bowel disease, Crohn's disease, irritable bowel syndrome, ulcerative colitis, obesity, diarrhea, bloating, flatulence, abdominal cramping, abdominal pain, constipation, and any combination thereof.

44. Use of a bacterium according to any one of embodiments 1-10 in the manufacture of a medicament.

45. Use of a bacterium according to 44 in the manufacture of a medicament for treatment or prevention of a disorder of the gastrointestinal tract of a subject, for example a subject according to any one of embodiments 23-27.

46. The use of a bacterium according to embodiment 44 or 45 in the manufacture of a medicament for the treatment of an inflammatory disorder.

47. The use of a bacterium according to embodiment 46, wherein said disorder is selected from the group consisting of: inflammatory bowel disease, Crohn's disease, irritable bowel syndrome, ulcerative colitis, obesity, diarrhea, bloating, flatulence, abdominal cramping, abdominal pain, constipation, and any combination thereof.

48. Use of a bacterium according to any one of embodiments 1-10 as a medicament.

49. The use of a bacterium according to embodiment 48, wherein the medicament is for treating or preventing a disorder of the gastrointestinal tract of a subject, for example a subject according to any one of embodiments 23-27.

50. The use of a bacterium according to embodiment 48 or 49, wherein the disorder is an inflammatory disorder.

51. The use of a bacterium according to embodiment 50, wherein said gastrointestinal disorder is selected from the group consisting of: inflammatory bowel disease, Crohn's disease, irritable bowel syndrome, ulcerative colitis, obesity, diarrhea, bloating, flatulence, abdominal cramping, abdominal pain, constipation, and any combination thereof.

Non-Numbered Embodiments

According to a first aspect there is provided a recombinant or isolated bacterium genetically modified to decrease the display of lipoteichoic acid (LTA) on the surface of said bacterium.

In one embodiment, the recombinant or isolated bacterium has been genetically modified to decrease the expression of a phosphoglycerol transferase. In a specific embodiment the recombinant or isolated bacterium has been genetically modified to decrease the expression of a phosphoglycerol transferase by about 3%-15%, 10%-25%, 20% to 35%, 30% to 45%, 40%-55%, 50%-65%, 60%-75%, 70%-90%, 70% to 80%, 70%-85%, 80%-95%, 90%-100% when compared to an unmodified control.

In a further embodiment, the recombinant or isolated bacterium has been genetically modified to decrease the expression of a polynucleotide comprising a nucleotide sequence having at least 70%, 80%, 90%, 91%, 92%, 93%, 94%, 95%, 96%, 97%, 98%, 99%, or 100% sequence identity to the nucleic acid sequence as set forth in any of SEQ ID NO: 1, 3, 5, 7, 9, 11, 13 or 15 or a fragment or variant thereof.

In a further embodiment, the recombinant or isolated bacterium of has been genetically modified to decrease the expression of a polynucleotide comprising the nucleotide sequence of SEQ ID NO: 1, 3, 5, 7, 9, 11, 13 or 15 or a fragment or variant thereof.

According to a second aspect there is provided a method of making a recombinant or isolated bacterium, said method comprising genetically modifying a bacterium to decrease the display of lipoteichoic acid on the surface of the bacterium. In a specific embodiment, the bacterium is modified by site-directed mutagenesis.

In a further embodiment, said recombinant or isolated bacterium has been modified to decrease the expression of a phosphoglycerol transferase.

It will be understood that the decrease in expression of the phosphoglycerol transferase may be as a result of disruption at the DNA, RNA or post translational level, suitable methods for achieving such a decrease in expression are known in the art and are discussed in further detail herein.

In another embodiment, said recombinant or isolated bacterium has been genetically modified to decrease the expression of a polynucleotide comprising the nucleotide sequence having at least 70%, 80%, 90%, 91%, 92%, 93%, 94%, 95%, 96%, 97%, 98%, 99%, or 100% sequence identity to the nucleic acid sequence as set forth in any of SEQ ID NO: 1, 3, 5, 7, 9, 11, 13 or 15 or a fragment or variant thereof.

In a further embodiment the *Lactobacillus acidophilus* has been modified to decrease the expression of a polynucleotide comprising the nucleotide sequence set forth in SEQ ID NO: 1, 3, 5, 7, 9, 11, 13 or 15 or a fragment or variant thereof.

In further embodiments, the recombinant or isolated bacterium is a probiotic bacterium. Specifically, a lactic acid bacterium. More specifically, *Lactobacillus* particularly *Lactobacillus acidophilus*. Even more specifically the genetic modification is performed on *L. acidophilus* NCFM.

In a specific embodiment, the recombinant or isolated bacterium is *Lactobacillus acidophilus* NCK2025, deposited under ATCC accession number PTA-11587.

In a third aspect there is provided a method of decreasing inflammation in a subject comprising, administering to said subject a therapeutically effective amount of the recombinant or isolated bacterium described elsewhere herein.

In one embodiment, the decrease in inflammation treats or prevents a disease of the heart such as coronary artery disease or heart failure.

In a fourth aspect there is provided a method of treating or preventing an inflammatory disorder of the gastrointestinal tract comprising, administering to a subject a therapeutically effective amount of the recombinant or isolated bacterium described elsewhere herein.

In one embodiment the subject is an animal, more specifically a mammal.

In another embodiment the subject is a human.

In a further embodiment the subject is a domestic animal.

In a still further embodiment, the subject is an agricultural animal.

In a further embodiment the subject has a gastrointestinal disorder.

In a specific embodiment, the gastrointestinal disorder is selected from the group consisting of: inflammatory bowel disease, Crohn's disease, irritable bowel syndrome, ulcerative colitis, obesity, diarrhea, bloating, flatulence, abdominal cramping, abdominal pain, constipation, and any combination thereof.

It will be understood that the bacterium may increase the production of one or more anti-inflammatory cytokines in the subject.

In a specific embodiment, the anti-inflammatory cytokine is IL-10.

In another embodiment, the bacterium decreases production of one or more pro-inflammatory cytokines in the subject.

In a further embodiment, the pro-inflammatory cytokine is selected from the group consisting of: IL-12, IL-6, IFNγ, TNFα, or any combination thereof.

In a further embodiment, the bacterium is administered in a therapeutically effective amount, wherein the therapeutically effective amount of the bacterium is about $10^8$ to $10^{12}$ CFU/day.

According to a fifth aspect, there is provided a pharmaceutical composition comprising the recombinant or isolated bacterium described herein.

According to a sixth aspect, there is provided the recombinant or isolated bacterium described herein for use as a medicament.

According to a seventh aspect, there is provided a recombinant or isolated bacterium described herein for use in treating or preventing a disorder of the gastrointestinal tract of a subject.

Specifically, the disorder is an inflammatory disorder.

More specifically, the gastrointestinal disorder is selected from the group consisting of: inflammatory bowel disease, Crohn's disease, irritable bowel syndrome, ulcerative colitis, obesity, diarrhea, bloating, flatulence, abdominal cramping, abdominal pain, constipation, and any combination thereof.

In another embodiment, the recombinant or isolated bacterium for use according to the methods described herein increases the anti-inflammatory cytokine production in the subject.

In one embodiment, the anti-inflammatory cytokine is IL-10.

In another embodiment, the recombinant or isolated bacterium for use according to the methods described herein decreases production of one or more pro-inflammatory cytokines in the subject.

In a further embodiment, the pro-inflammatory cytokine is selected from the group consisting of: IL-12, IL-6, IFNγ, TNFα, or any combination thereof.

It will be understood that the bacterium is provided in a therapeutically effective amount, wherein the therapeutically effective amount of the bacterium is about $10^8$ to $10^{12}$ CFU/day.

According to an eighth aspect there is provided the use of a bacterium as described elsewhere herein in the manufacture of a medicament.

In a specific embodiment, the medicament is for treating or preventing a disorder of the gastrointestinal tract of a subject.

In a further embodiment, the disorder is an inflammatory disorder.

In a further embodiment, the gastrointestinal disorder is selected from the group consisting of: inflammatory bowel disease, Crohn's disease, irritable bowel syndrome, ulcerative colitis, obesity, diarrhea, bloating, flatulence, abdominal cramping, abdominal pain, constipation, and any combination thereof.

According to a ninth aspect, there is provided the use of a bacterium described herein as a medicament.

In a specific embodiment, the medicament is for treating or preventing a disorder of the gastrointestinal tract of a subject.

In a further embodiment, the disorder is an inflammatory disorder.

In a further embodiment, the disorder is selected from the group consisting of: inflammatory bowel disease, Crohn's disease, irritable bowel syndrome, ulcerative colitis, obesity, diarrhea, bloating, flatulence, abdominal cramping, abdominal pain, constipation, and any combination thereof.

It will be apparent that the subject in relation to any aspect described herein may be any suitable subject, for example, a subject as described in relation to the fourth aspect above.

Further aspects are described above. It will be readily apparent to a person skilled in the art that any features described in relation to one particular aspect are equally applicable to all other aspects unless specifically stated otherwise or clearly incompatible.

The following examples are offered by way of illustration and not by way of limitation.

EXPERIMENTAL

Example 1

Decreasing the Display of LTA in *Lactobacillus acidophilus*.

In *L. acidophilus* NCFM (NCK56); the genes LBA0444-LBA0447 were identified and annotated for their putative roles in LTA biosynthesis (FIG. 1B). The genes LBA0444 and LBA0448 are flanked by putative rho-independent terminators (Kingsford C, Ayanbule K, & Salzberg S (2007) *Genome Biology* 8 (2):R22), indicating that these two genes are co-transcribed and function as an operon. While LBA0444-LBA0447 genes have a putative role in LTA biosynthesis, LBA0448 is a hypothetical protein that does not appear to play a role in this cascade.

*Lactobacillus* species can effectively activate various signals in DCs that, in turn induce T cell immune responses (Mohamadzadeh M, et al. (2005) *Proc Natl Acad Sci USA* 102(8):2880-2885; Konstantinov S R, et al. (2008) *Proc Natl Acad Sci USA* 105(49):19474-19479). To further investigate the molecular mechanisms involved in modifying DC-function, we specifically deleted the phosphoglycerol transferase gene (LBA0447) in *L. acidophilus* NCK56. PCR analysis of this genomic region showed that the deletion mutant, NCK2025, lost 2 kbp (FIG. 1C-D). Sequencing over this region confirmed the elimination of LBA0447. Chromatographic analysis of cell wall extracts of the parent NCK56 and mutant NCK2025 demonstrated the absence of LTA in the mutant where the phosphoglycerol transferase gene had been deleted NCK2025 Treated-DCs.

Figure 2:
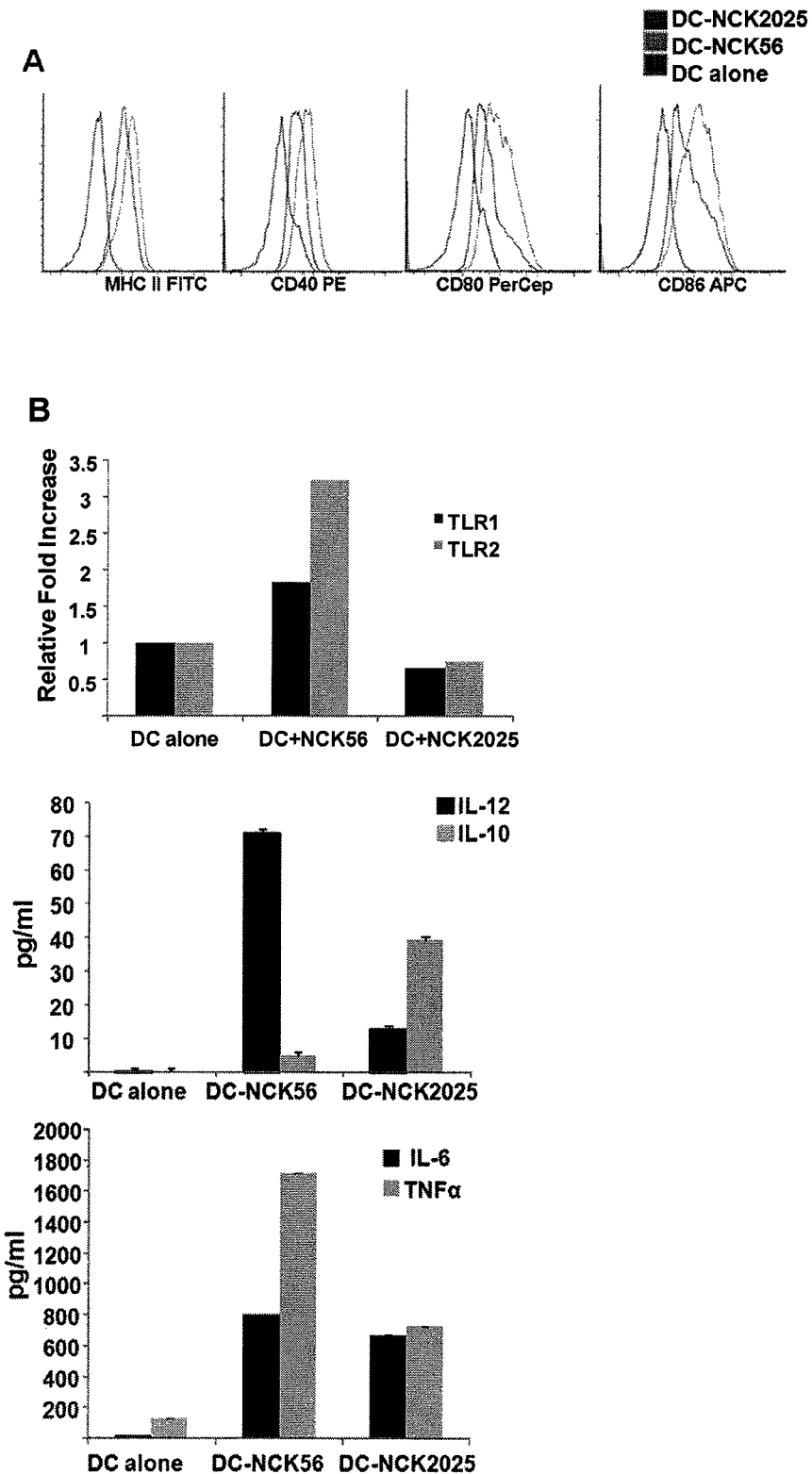
FIG. 2 (A) shows the phenotype of DCs treated with NCK56 (also designated as *L. acidophilus* NCFM) or NCK2025. Bone marrow derived DCs were co-cultured with NCK56 or NCK2025 for 24 hours. Cells were stained with corresponding antibodies, fixed and subsequently analyzed by a FACSCalibur. Panel B shows DCs cultured alone or 1:1 with either NCK56 or NCK2025 for 1 and 6 hours. RNA was extracted, reverse transcribed and real-time PCR was performed using primers for TLR1 and TLR2. Data shown represents the 1 hr DC alone, or co-cultures of these cells with NCK56 or NCK2025. Panel C shows cytokine analysis. Cytokines released in the supernatants of NCK56 or NCK2025-treated and untreated DCs were assayed by ELISA. Panel D shows T cell proliferation. Groups of C57BL/6 mice (5/group) were orally treated with NCK56 or NCK2025 for four consecutive days. Mesenteric LN-T cells were derived and co-cultured with NCK56 or NCK2025-treated and untreated DCs for four days to assay T cell proliferation using [$^3$H]thymidine incorporation. In some experiments, to restore the suppressed T cell proliferation, anti-IL-10 antibodies were added to supernatants derived from DCs that were co-cultured with NCK2025. Mesenteric LN-T cells derived from each group of mice were co-cultured with DCs that were treated or untreated with *L. acidophilus* strains to assay cytokines.

Co-culturing DCs with NCK56 or LTA-negative mutant (NCK2025) showed that NCK2025 down-regulated MHC 11, CD40, CD80 and CD86 on the surface of DCs (FIG. 2A). Moreover, treatment of DCs with NCK56 induced the transcription of TLR1 and 2 while these two pattern recognition receptors (PRRs) were not activated in NCK2025 treated-DCs (FIG. 2B). Both strains induced IL-10 production in DCs; however, the production of this cytokine was significantly increased in DCs co-cultured with NCK2025 (FIG. 2C). Concomitantly, IL-12 and TNFα were significantly reduced in NCK2025 treated-DCs (FIG. 2C). T cell proliferation was determined by co-culturing mesenteric LN derived T cells with bone marrow derived DCs treated with NCK56 or NCK2025. T cell proliferation was significantly abrogated in NCK2025 treated-DCs co-cultured with T cells relative to NCK56 (FIG. 2D). Interestingly, adding anti-IL-10 antibody to the supernatant of NCK2025 treated-DCs partially restored the proliferation of T cells indicating that IL-10 may be a pivotal factor that regulates T cell proliferation in the DC:T cell co-cultures. Analysis of harvested supernatants from DC:T cell co-cultures showed that IL-10 was highly induced in T cells while IFNγ, IL-2, and TNFα were minimally released from T cells of mice that were treated with NCK2025 (FIG. 2E).

Amelioration of DSS-Induced Colitis by NCK2025.

Figure 3A:
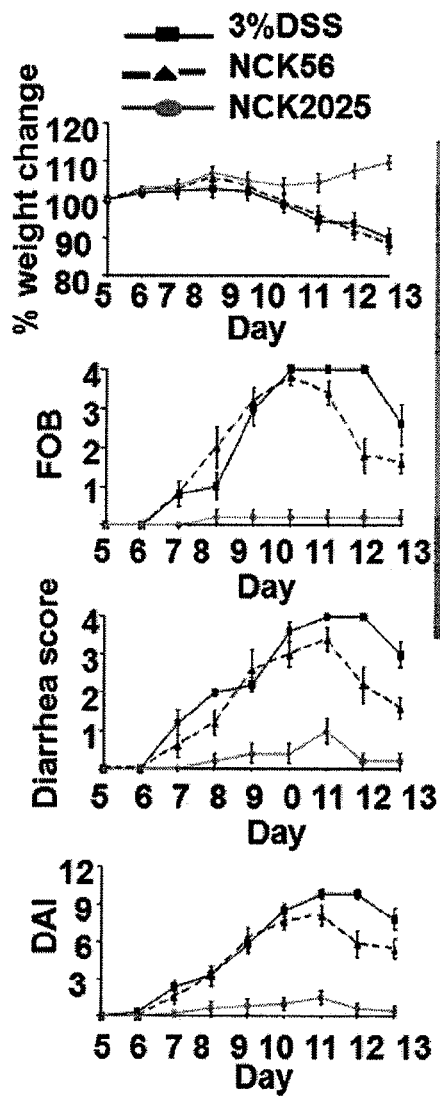
FIG. 3 shows the amelioration of DSS-induced colitis by NCK2025. Panel A shows C57BL/6 mice (n=10) orally inoculated with NCK56 or NCK2025 ($5\times10^8$ cfu/100 μl/mouse) or PBS for 4 consecutive days. These groups of mice were exposed to 3% DSS dissolved in the drinking water for 5 days followed by 7 days of plain water and assessed over time for colitis progression, including H&E staining, weight lost, diarrhea and hemoccult positivity. Panels B-E show colonic H&N staining B shows untreated mice; C shows DSS-treated mice; D shows NCK56-DSS treated mice; and E shows NCK2025-DSS treated mice. F represents the colitis score. FOB stands for fecal hemoccult blood positivity and DAI stands for disease activity index. Data are representative of at least three independent experiments. Panel G shows the colonic cytokine analysis. Colons of the mice (5/group) that were treated with NCK56 or NCK2025 or DSS were cleaned with cold PBS, cut into pieces and cultured for 18 h at 37° C. Cytokines were assayed by ELISA.
Figure 3A:
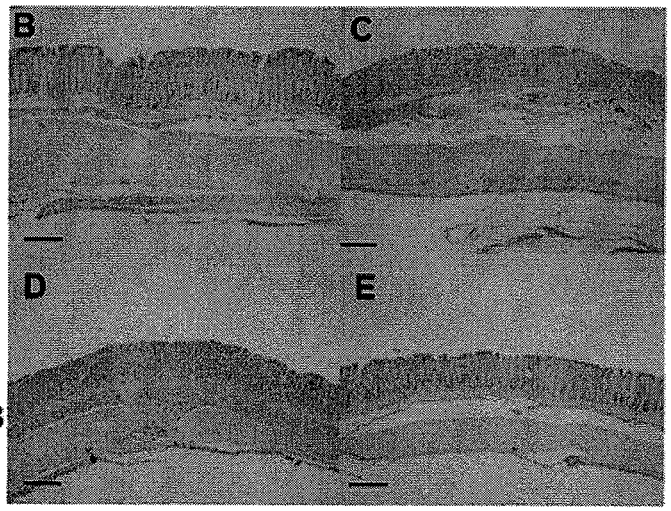
Figure 3A:
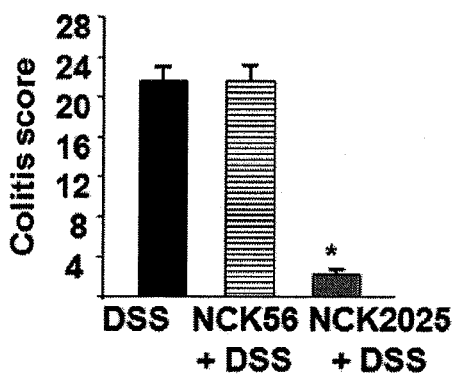
Figure 3B:
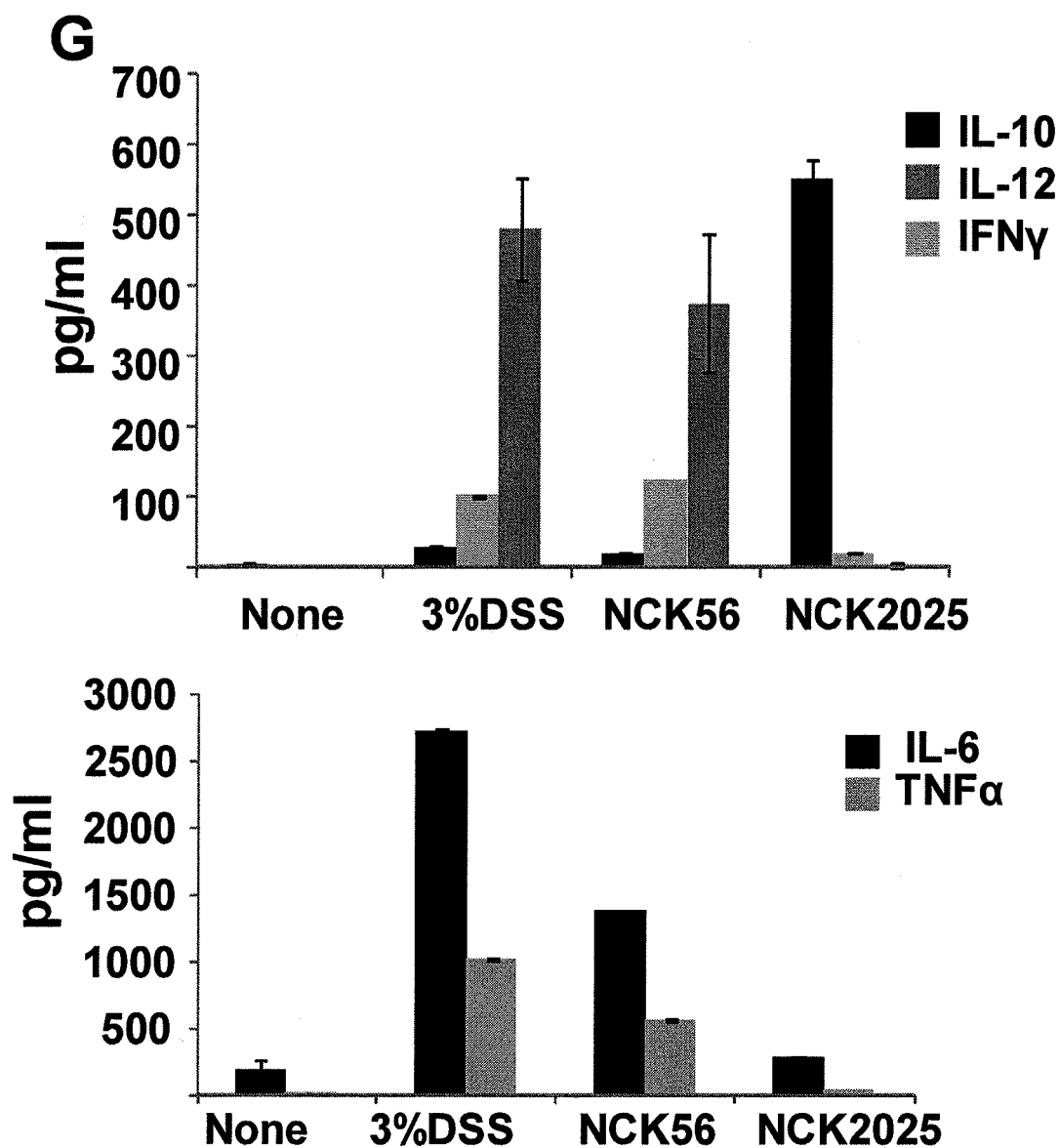

To determine the immunomodulatory properties of NCK2025 in vivo, DSS-induced colitis was analyzed in mice that were treated with NCK56 or NCK2025 for four consecutive days before (preventative) or after (therapy) exposure to 3% DSS. Data show that DSS induced clinical and histological colitis in untreated C57BL/6 mice (FIG. 3A, C) relative to baseline (FIG. 3B). Clinically, mice began to lose weight after day 9 with approximately 10% overall weight loss by day 13 and developed severe bloody diarrhea around day 10 to 11 (FIG. 3A). By contrast, oral inoculation of the mice with NCK2025 significantly prevented weight loss, reduced diarrhea and hemoccult positivity (FIG. 3A). Overall, the "Disease Activity Index" (DAI) was significantly reduced from day 2 forward. Moreover, pretreatment of the mice with NCK2025 reduced histological colitis scores up to 90% (21.5±1.4 to 2.3±0.5) (FIG. 3B-F). Accordingly, FIG. 3E represents intact, non-ulcerated epithelium with limited inflammation confined to the mucosa. To specifically address the role of LTA deletion in the prevention of colitis by NCK2025, a third group of mice were treated with NCK56. The wild type $L.$ $acidophilus$ NCK56 did not prevent the onset of colitis (FIGS. 3A and 3D) and the mice developed similar clinical and histological colitis to non-treated mice. To elucidate the cytokines expressed by colonic tissues, the colons were extracted from each group of mice and cultured overnight. Colonic cytokine analysis shows the levels of IL-6, IL-12, TNFα and IFNγ were higher in colons derived from NCK56- and DSS-treated mice (FIG. 3G). By contrast, IL-10 production was significantly elevated in colonic cultures derived from NCK2025 treated mice. IL-12, IL-6, IFNγ and TNFα were significantly reduced in the colons of the mice treated with NCK2025 (FIG. 3G).

Figure 7B:
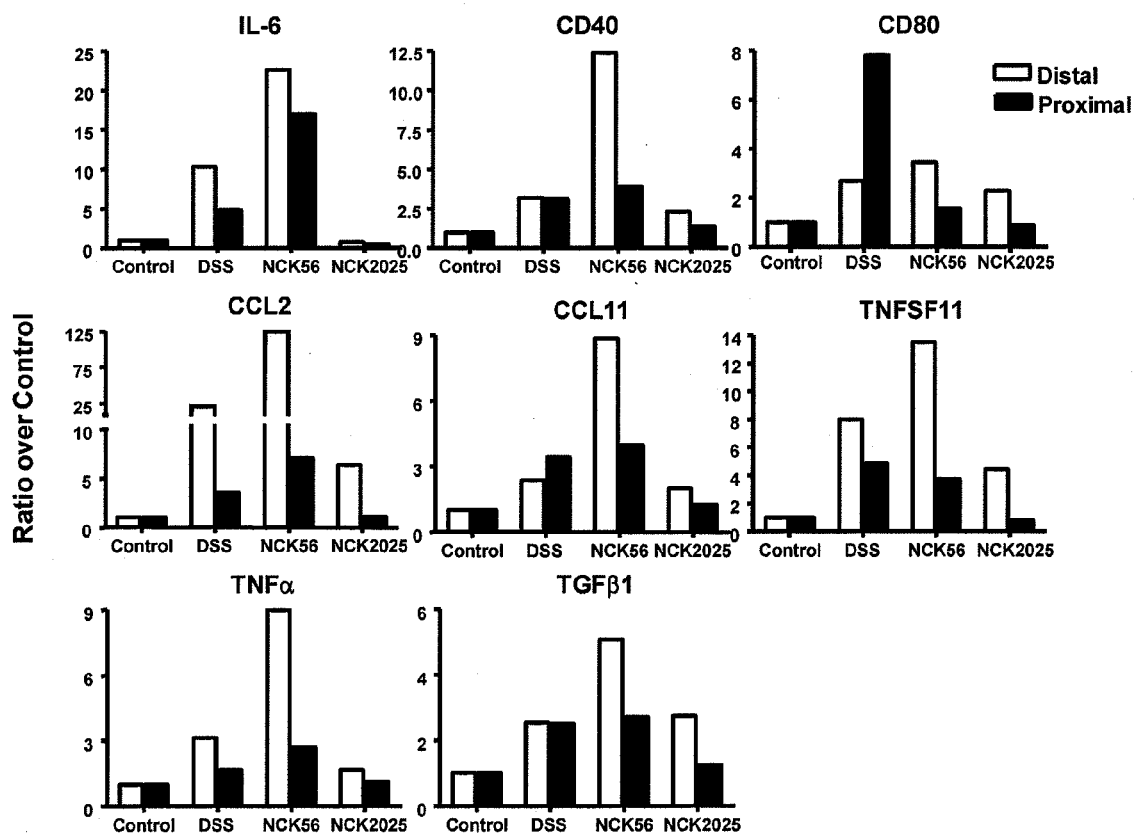
FIG. 7 shows regulation of genes in DSS induced colitis in mice upon treatment with NCK56 or NCK2025 or no treatment. Panels A-B show mice (5/group) given NCK56, NCK2025, or left untreated, for four days before DSS induction of colitis. Proximal or distal colonic regions were isolated and RNA extracted. cDNA microarray analysis reveals differential gene expression patterns in pathways involving immune regulatory/stimulatory, signaling, proliferation, apoptosis, angiogenesis, and adhesion in the colon of mice. Values represent fold increase in expression (>1.0) or fold decrease in expression (<1.0) of genes exposed to experimental conditions compared to control mice.
Figure 7C:
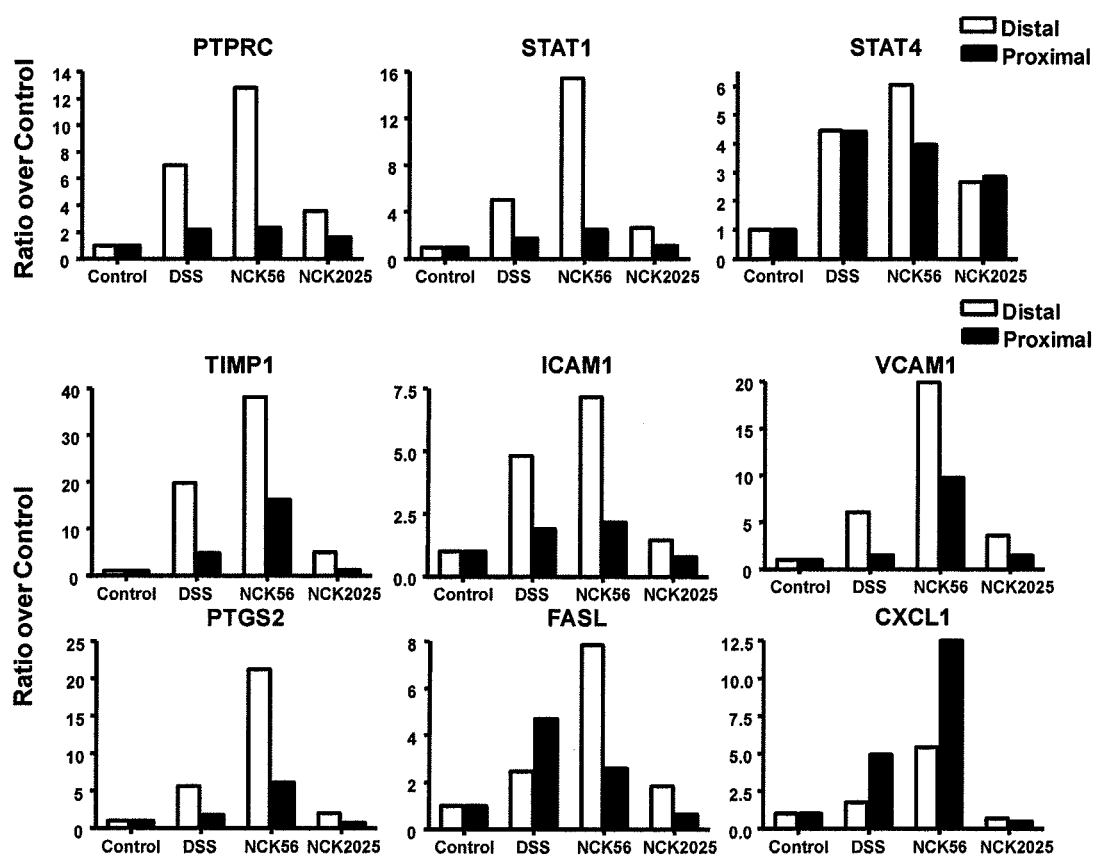

In addition, investigation of genes in distal and proximal regions of mice that were inoculated with NCK56 versus NCK2025 in DSS induced colitis revealed the upregulation of immune stimulatory (i.e. CD40, CCL11), signaling (i.e. Stat1, Stat4), and proliferation/apoptosis/angiogenesis/proteinase (i.e. TIMP1, FASL, ICAM1) genes suggesting active inflammatory responses in NCK56, but not in NCK2025-treated mice (FIGS. 7A and 7B). Interestingly, various regulatory, signaling and anti-inflammatory genes [i.e. platelet activating factor acetylhydrolase (PLA2G7), serum response factor (SRF), TGFβ, (p21-activated kinases PAK1, RAFT, tissue inhibitor of matrix metalloproteinase (TIMP1), Tyk2] were highly regulated in colonic distal (not proximal) regions in NCK2025, but not NCK56- or DSS alone treated mice (FIG. 7A). This implies that such genes become significantly activated to exert their regulatory functions in the distal colon where DSS-induced colitis is more severe.

Therapeutic Effects of NCK2025 on DSS-Induced Colitis.

Figure 4A:
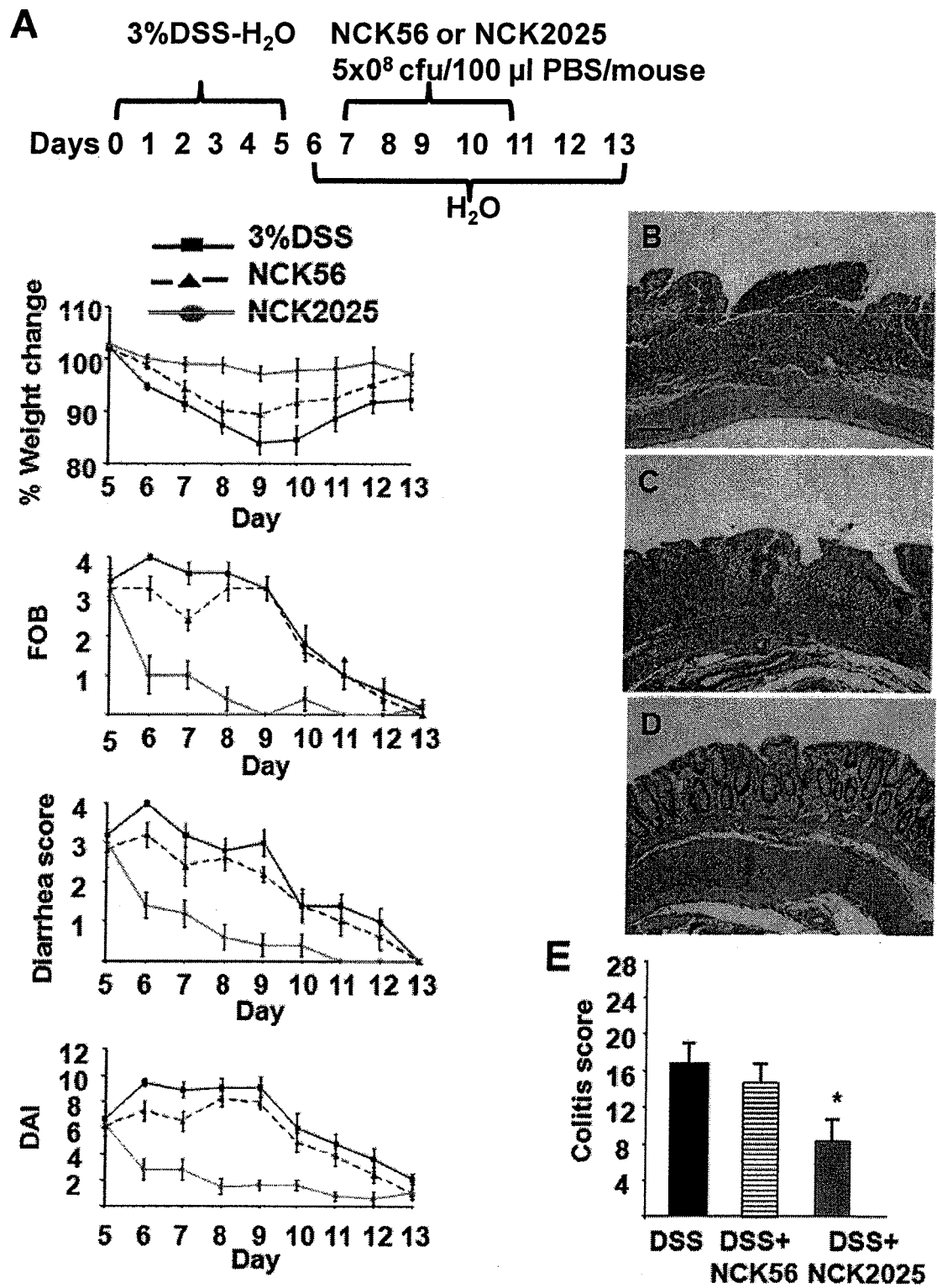
FIG. 4 shows mitigation of established colitis by NCK2025. Panels A-D show three groups of C57BL/6 mice (10/group) that first received a five-day cycle of 3% DSS dissolved in sterile water to initiate colitis, and two of the groups were subsequently treated orally with NCK56 or NCK2025 for four consecutive days. Disease progression was monitored to day 13 of the protocol when mice were sacrificed, and colons assessed. Panels B-D show colonic H&N staining Panel B shows DSS-treated mice; Panel C shows DSS-NCK56 treated mice; Panel D shows DSS-NCK025 treated mice. Panel E represents the colitis score. FOB stands for fecal hemoccult blood positivity and DAI stands for disease activity index. Data are representative of at least three independent experiments. Panel F shows the colonic cytokine analysis. Colons of each group of mice were washed, cut into pieces and cultured for 18 h at 37° C. Cytokines were assayed by ELISA.
Figure 4B:
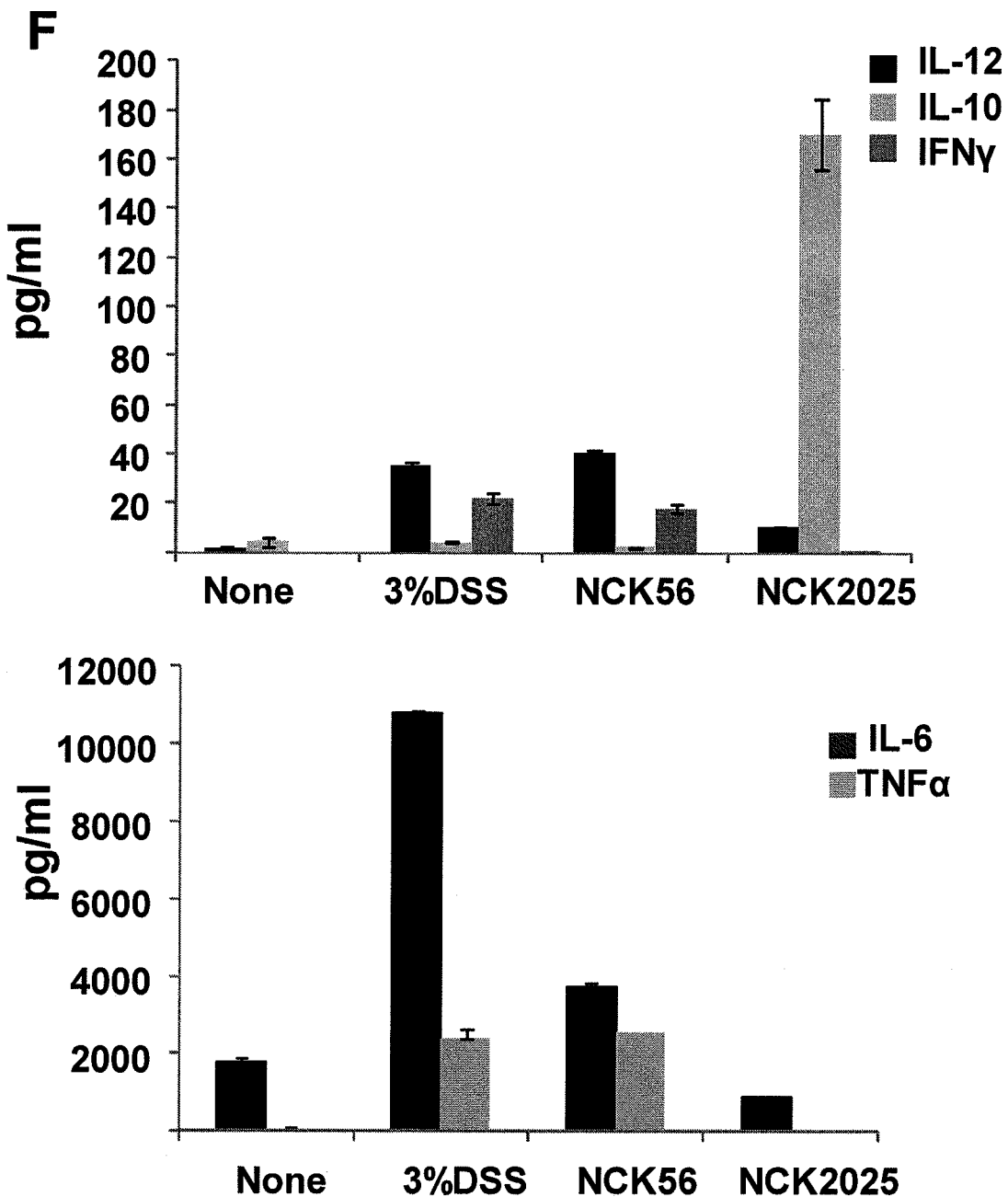

To address the effects of NCK2025 exposure in mice with established colitis, mice were first exposed to 3% DSS before treatment with NCK56 or NCK2025. Once disease symptoms occurred, mice received NCK56 or NCK2025 for four consecutive days (FIG. 4A). Data show that both NCK56 and NCK2025 attenuated established colitis, but to a significantly different degree. Treatment of mice with NCK2025 resulted in stabilization of body weight and rapid resolution of diarrhea and blood loss, while NCK56-treated mice continued to lose weight, albeit at a slower rate, and was significantly slower to resolve diarrhea and blood loss (FIG. 4A). Histological analysis revealed ongoing, active colitis and ulceration with a colitis score of 16.8±2.2 in DSS-treated mice at day 13 (FIG. 4B, E). Mice treated with NCK2025 had significantly improved colitis scores (8.4±2.2, p=0.01), demonstrating accelerated healing, including rare ulceration, regenerated crypt structures, and inflammation primarily limited to the mucosa (FIG. 4D, E). Once again, NCK56 treatment mildly improved histological colitis scores (14.7±2.0, p=NS) with restitution of the epithelium, but limited crypt regeneration and ongoing active inflammation within the mucosa and submucosa (FIG. 4C, E). Interestingly, cytokine analysis of the mice treated with NCK2025 shows upregulation of IL-10 and minimal release of IL-12, TNFα, IL-6 and IFNγ in the colons of these mice (FIG. 4F). By contrast, IL-12, TNFα, IFNγ, and IL-6 were highly induced in the colons of mice treated with NCK56 or DSS alone, and IL-10 was minimally released in these groups of mice (FIG. 4F).

Induction of Colonic CD4$^+$FoxP3$^+$T Cells by NCK2025.

Figure 5:
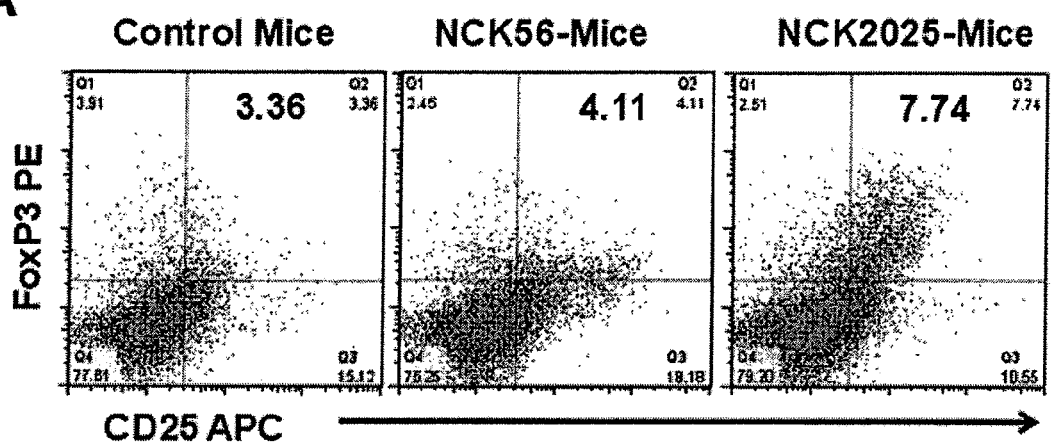
FIG. 5 shows induction of Treg cells by NCK2025. Panels A-B show C57BL/6 mice (5/group) orally inoculated with NCK56 or NCK2025 ($5 \times 10^8$ cfu/100 µl/mouse) or PBS for 4 consecutive days. On day five, mice were sacrificed, and isolated colons were cleaned. Colonic single cell-suspensions were prepared from each group of mice and enriched by Percol gradient. Lymphocytes were stained with corresponding or isotype match antibodies and analyzed by FACSCalibur. Experiments were repeated at least 7 times.
Figure 5:
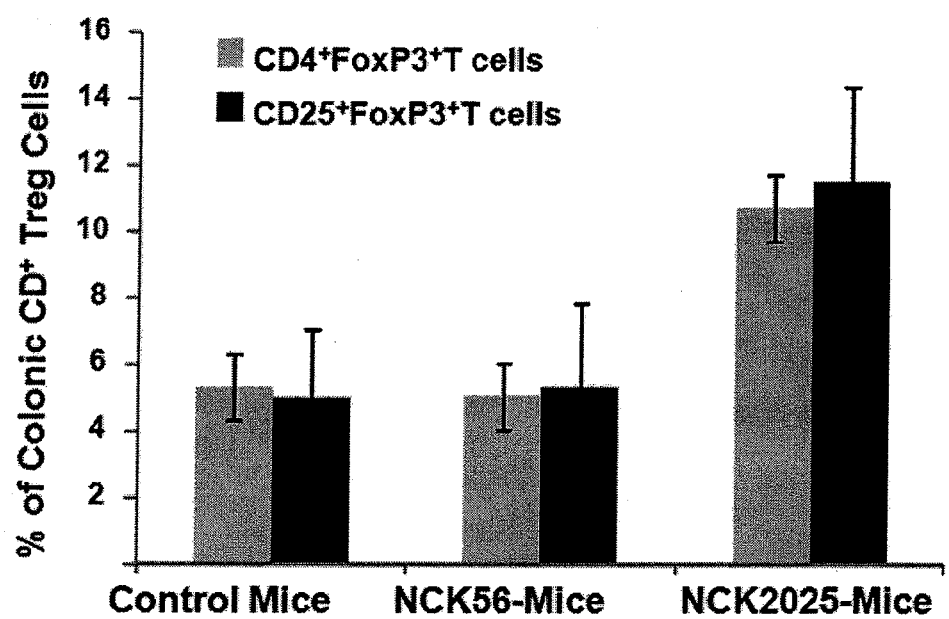

The role of CD4$^+$ Treg cells has recently been highlighted in suppressing deregulated immune responses to self and to commensal microbiota (Fontenot J D, Gavin M A, & Rudensky A Y (2003) $Nat$ $Immunol$ 4(4):330-336). Accordingly, NCK2025, that induces IL-10 in DCs and in the colonic microenvironment of treated mice, was investigated to determine if it enhances colonic CD4$^+$FoxP3$^+$ Treg cells in C57BL/6 mice when compared to NCK56. Indeed, FIGS. 5A & B show that Treg cells were significantly induced in the colons of the mice treated with NCK2025 compared to NCK56 suggesting that the suppressor effects of these cells may impact exaggerated inflammation induced by DSS at the mucosa.

Regulatory Effect of IL-10.

Figure 6:
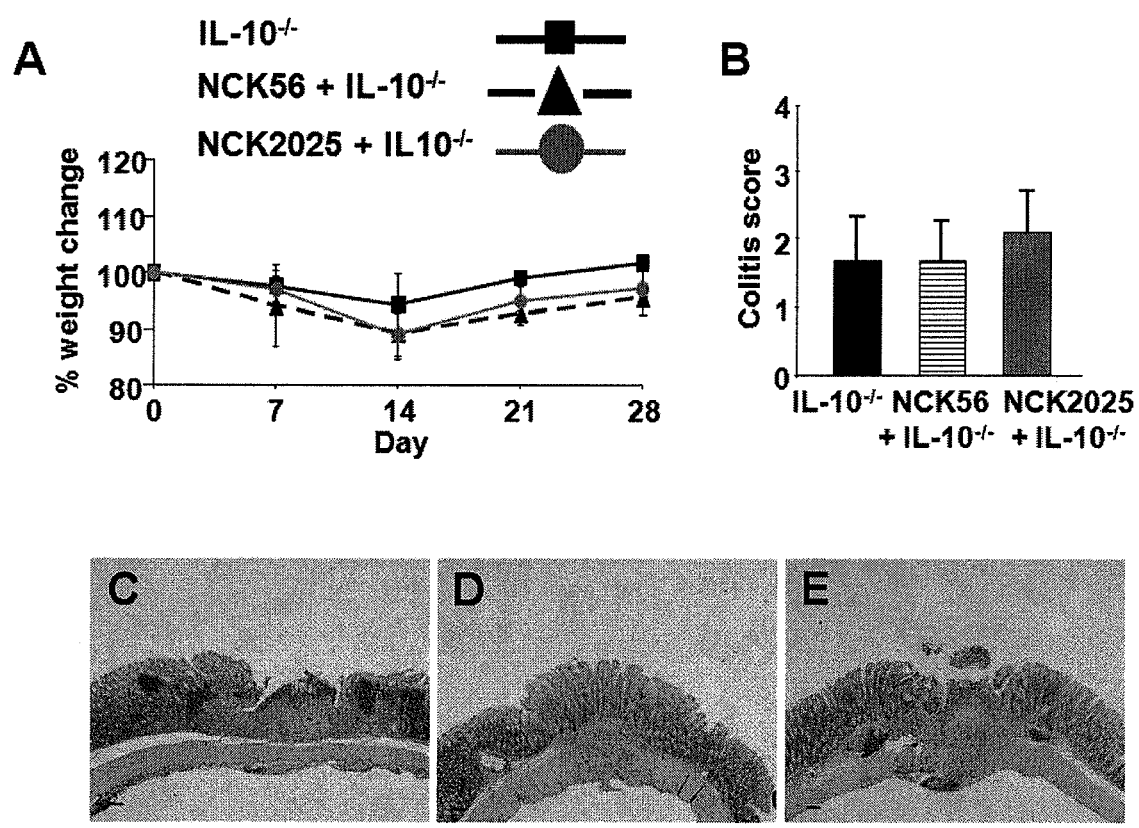
FIG. 6 shows induction of Colitis in $IL-10^{-/-}$ mice. A-B: C57BL/6 $IL-10^{-/-}$ mouse groups (10/group) were housed conventionally for 1 week. Mice were inoculated with NCK56 or NCK2025 for four consecutive days and then fed low dose piroxicam for 1 week, followed by high dose piroxicam for 1 week to accelerate and induce the onset of colitis. Weight lost was determined and two weeks later mice were sacrificed, colon cross-sectional Swiss rolls and tissue sections were prepared for H&E staining C shows Piroxicam alone treated mice; D shows NCK56-piroxicam treated mice; and E shows NCK2025-piroxicam treated mice. The scores were blindly determined on a scale from 0 to 4.

Data from in vitro studies, as well as cytokine analysis in vivo, suggest the effect of NCK2025 to ameliorate colitis is dependent on the induction of IL-10 at the mucosa (Kuhn R, Lohler J, Rennick D, Rajewsky K, & Muller W (1993) $Cell$ 75(2):263-274). To confirm these observations, "preventative" and therapeutic studies were performed as above in IL-10$^{-/-}$ mice. IL-10$^{-/-}$ mice develop spontaneous Th1-mediated colitis upon exposure to commensal bacteria, with deep, transmural ulcerating lesions similar to human Crohn's disease (Berg D J, et al. (1996) *J Clin Invest* 98(4):1010-1020). Prior to the onset of colitis, mice were inoculated with NCK56 or NCK2025 (or no treatment as a control group) for four consecutive days. The onset of colitis was induced by treatment with piroxicam as described above. Clinically, weight loss was monitored over 28 days, and colons were isolated after sacrifice to assess the degree of histologic colitis. There was no protection from expected weight loss seen during the first two weeks of induced colitis by either NCK56 or NCK2025 (FIG. 6A). Collectively, all three groups developed similar histological colitis and colitis scores (FIGS. 6B-E), suggesting that endogenous IL-10 is required for NCK2025's immunomodulatory properties.

Discussion

Breakdown in the immune mechanisms controlling intestinal immune tolerance leads to chronic IBD (Macdonald T T & Monteleone G (2005) *Science* 307(5717):1920-1925; MacDonald T T & Gordon J N (2005) *Gastroenterol Clin North Am* 34(3):401-412, vii-viii). Increased numbers of IFNγ$^+$ T cells in the lamina propria of patients with CD strongly suggests the involvement of Th1 polarization in the pathogenesis of IBD (Fuss I J, et al. (1996) *J Immunol* 157 (3):1261-1270; 25-27; Neurath M F, Duchmann R, & Meyer zum Buschenfelde K H (1996) *Dtsch Med Wochenschr* 121 (22):735-741 (in ger); Neurath M F, et al. (1996) *J Exp Med* 183(6):2605-2616) leading to uncontrolled gut inflammation and tissue destruction (Powrie F (1995) *Immunity* 3(2):171-174). Both CD8$^+$ (Cheroutre H (2006) *Gastroenterology* 131 (2):667-670; Vezys V & Lefrancois L (2002) *J Immunol* 169 (12):6677-668) and CD4$^+$ T cells (Elson C O, et al. (2005) *Immunol Rev* 206:260-276; Wirtz S & Neurath M F (2000) *Int J Colorectal Dis* 15(3):144-160) trigger intestinal inflammation when peripherally activated by inflammatory cytokines (i.e. IL-12) released from highly activated DCs. Thus, an efficacious immunotherapy requires a deep understanding of the immune signaling mechanisms that underlie the immune tolerance breakdown generally sustained by regulatory signals (Wirtz S, et al. (1999) *J Immunol* 162(4):1884-1888).

Recently, sequencing and annotation of the *L. acidophilus* genome has allowed genetic manipulation of this bacterium's cell surface components that may affect mucosal cellular and molecular events, ultimately leading to therapeutic applications (Konstantinov S R, et al. (2008) *Proc Natl Acad Sci USA* 105(49):19474-19479; Altermann E, et al. (2005) *Proc Natl Acad Sci USA* 102(11):3906-3912). The cell wall and cell surface proteins of *L. acidophilus* comprise components that are critical for the maintenance of cell shape and activation of immune cells, including DCs (Konstantinov S, et al. (2008) *Proc Natl Acad Sci USA* 105(49):19474-19479). To study the complex crosstalk between bacteria and innate cells (i.e. DCs) and its relevance to colitis, the gene encoding the phosphoglycerol transferase that synthesizes the glycerol chain of LTA in *L. acidophilus* was deleted. Data show that the *L. acidophilus* LTA-negative mutant, NCK2025, induced regulatory signals (i.e. IL-10) and less co-stimulatory molecules (CD40, CD86) in mouse DCs, in effect converting these cells to regulatory DCs (Belkaid Y & Oldenhove G (2008) *Immunity* 29(3):362-371). Subsequent interaction of such regulatory DCs with CD4$^+$ T cells significantly altered T cell activation. Furthermore, NCK2025 treatment ameliorated DSS-induced colitis indicating that pretreatment of the animal with this bacterial strain induced regulatory immunity that resists DSS-challenge as demonstrated by colonic histology, weight loss, reduced diarrhea and hemoccult positivity.

One of the mechanisms that regulates overt inflammatory responses within the mucosa is IL-10 (Kraus T A, et al. (2005) *J Clin Invest* 115(8):2234-2243; Kraus T A & Mayer L (2005) *Curr Opin Gastroenterol* 21(6):692-696). Our data clearly show that this cytokine is highly secreted not only by DCs, but also by colonic tissues of the mice treated with NCK2025, a phenomenon seen in both preventive and therapeutic strategies for treatment of DSS colitis. It has previously been shown that IL-10 modulates both innate and adaptive immune responses via its ability to exert anti-inflammatory effects (Moore K W, de Waal Malefyt R, Coffman R L, & O'Garra A (2001) *Annu Rev Immunol* 19:683-765; Trinchieri G (2007) *J Exp Med* 204(2):239-243). This cytokine functionally suppresses T cells by down-regulating MHC II, co-stimulatory molecules and the production of IL-12 in DCs, all of which are strongly involved in T cell differentiation and activation (Moore K W, de Waal Malefyt R, Coffman R L, & O'Garra A (2001) *Annu Rev Immunol* 19:683-765; de Waal Malefyt R, Abrams J, Bennett B, Figdor C G, & de Vries J E (1991) *J Exp Med* 174(5):1209-1220). Additionally, IL-10 also regulates CD8$^+$ cytotoxic T lymphocytes (CTL), B cells and Th1 polarization (Moore K W, de Waal Malefyt R, Coffman R L, & O'Garra A (2001) *Annu Rev Immunol* 19:683-765) via its activated IL-10 receptors that initiate multiple signaling cascades, including Jak1, Tyk2, and Stat3 pathways in lymphocytes (Finbloom D S & Winestock K D (1995) *J Immunol* 155(3):1079-1090). These observations demonstrate that the regulation and maintenance of mucosal tolerance is critically governed by IL-10 that profoundly modifies pathogenic CD4$^+$ T immune responses, consistent with findings presented here. In addition, the pivotal role of IL-10 in response to innocuous antigens was recently demonstrated using IL-10-deficient mice that develop severe colitis (Kuhn R, Lohler J, Rennick D, Rajewsky K, & Muller W (1993) *Cell* 75(2):263-274). As seen above, the immunomodulatory effects of NCK2025 were not sufficient to completely reverse established colitis in IL-10$^{-/-}$; however, it did abrogate the induction of colitis when given in a preventative/therapeutic manner, highlighting the critical role of IL-10 in regulating the onset of inflammation.

Importantly, mounting evidence supports the notion that IL-10 secreting Treg cells control the inflammatory properties of DCs (Lund J M, Hsing L, Pham T T, & Rudensky A Y (2008) *Science* 320(5880):1220-1224) that in turn regulate the induction of an efficient T cell immunity to control collateral tissue damage (Matarese G, De Rosa V, & La Cava A (2008) *Trends Immunol* 29(1):12-17). In this regard, we show that the *L. acidophilus* LTA-negative mutant treatment increased the number of CD4$^+$FoxP3$^+$ Treg cells in the colons of the mice. These observations strongly support the critical role of Treg cells in inflammatory disorders, as demonstrated previously in both human and rodent models where mutations in the FoxP3 gene result in uncontrolled proliferation and significant elevation of Th1 and Th2 cytokine signals (Fontenot J D, Gavin M A, & Rudensky A Y (2003) *Nat Immunol* 4(4):330-336). Additional mechanisms that may regulate IL-10 and its subsequent effects on innate and T cells remain to be determined. Complete deletion of the entire gene involved in LTA synthesis in *L. acidophilus* results in a derivative bacterium that significantly impacts the intestinal microenvironment, inducing regulatory signals (i.e. IL-10, Treg cells) and can restore cellular coexistence during induced inflammatory immune responses. *L. acidophilus* presents a unique display of S-layer proteins that profoundly alter DC functions (Konstantinov S R, et al. (2008) *Proc Natl Acad Sci USA* 105(49):19474-19479, Mohamadzadeh M, Duong T, Sandwick S J, Hoover T, & Klaenhammer T R (2009) *Proc Natl Acad Sci USA* 106(11):4331-4336). The S-layer of *L. acidophilus* is composed of three S-layer A, B and X genes (Goh Y J, et al. (2009) *Appl Environ Microbiol*

75(10):3093-3105, Goh Y J & Klaenhammer T R (2009) *Front Biosci* 14:1362-1386) whereupon the "self assembling" S-layer proteins A or B are the major proteins covering the surface of this bacterium. Gene modification in an allochthonous bacterium that does not permanently colonize the gut may offer more therapeutic options when immune responses are regulated (i.e. active IBD) or left unperturbed (i.e. intestinal infections) by administering probiotic microbes. This would facilitate development of therapeutic vehicles that may optimize the regulation of oral immune responses. Accordingly, establishing such a probiotic intervention against autoimmune diseases must be carefully orchestrated from various immunological perspectives to achieve better clinical outcomes.

First, dominant regulation of inflammation should not be constant as inflammation is a part of regular immunity (Nathan C (2002) *Nature* 420(6917):846-852). A bacterium that colonizes the gut may impair immune responses that are required to maintain the intestinal regulatory/co-stimulatory immune balance. For example, during infection, the inflammation process allows for recognition of the pathogen, and activation of innate and adaptive immune responses that facilitate recovery from infection. Thus, inflammation orchestrating series of events must be properly phased and regulated to achieve microbe elimination yet prevent unnecessary tissue damage due to presence of various immune cascades and the pathogen. Such an inflammatory process can be controlled via specific checkpoints and feedback loops that can provoke escalation, suppression or regulation of the inflammatory response. Such positive and negative feedback loops rely on a variety of molecules that mediate inflammatory responses, ultimately playing a regulatory role in its control. Importantly, an active immunity that mobilizes signals toward bacterial clearance requires optimal cellular co-stimulation controlled by regulatory signals (i.e. IL-10) that is partly induced by inflammatory signals.

Second, to achieve transient regulatory immunity, tools, including the bacteria species, must be carefully selected and used. In this regard, genetic construction of a LTA-deletion derivative of the widely used probiotic microbe, *L. acidophilus* NCFM, to dampen inflammation was instrumental in our approach. Because this bacterium harbors no new genes or DNA sequences and does not permanently colonize the gut; it can serve as an ideal vehicle to induce regulatory immune responses when orally inoculated. This implies that once the goal of tuning down inflammation is achieved, any the probiotic supplement can be stopped to re-establish "normal" immunity in the gut. Finally, these studies, establish how the deletion of LTA in *L. acidophilus* initiates regulatory mechanisms in innate cells without neglecting the required co-stimulatory signals for efficacious immune activation in diseases such as infection.

Together, targeted preventive or therapeutic strategies will be effective when cellular interactions are understood, in depth, and critical molecules identified that culminate in autoimmunity, inflammation, or anti-inflammatory responses.

Methods

Reagents.

Piroxicam and Sulindac were obtained from Sigma (St. Louis, Mo.). Dextran Sulfate Sodium (DSS) was obtained from MP Biochemicals (Solon, Ohio). NS-398 was obtained from Cayman Chemical Company (Ann Arbor, Mich.). Monoclonal antibodies for CD4, CD25, FoxP3, CD3, CD11c, CD11b, CD40, CD80, CD86, IL-10, and mouse GM-CSF were purchased from Invitrogen (Carlsbad, Calif.) and eBioscience (San Diego, Calif.).

Bacterial Strains.

*L. acidophilus* NCK56 and NCK2025 were inoculated at 1% and propagated in de Man, Rogosa, and Sharpe broth (MRS, Difco) at 37° C. for 15 h. Subsequently, 1 ml of each culture was transferred to 50 ml of fresh MRS and incubated at 37° C. for 18 hrs. The number of colony-forming units (CFU) of *L. acidophilus* strains was determined by measuring the optical density at 600 nm (Greene J D & Klaenhammer T R (1994) *Appl Environ Microbiol* 60(12):4487-4494). Cells were harvested by centrifugation, washed twice with sterile PBS, resuspended at $5 \times 10^8$ CFU/ml PBS containing 20% glycerol, and subsequently stored at −80 until used to stimulate immature DCs (1:1) in vitro. For oral inoculation of the mice, grown bacteria for 48 hrs were washed twice with sterile PBS, resuspended at $5 \times 10^9$/ml of PBS, and used for oral inoculation of mice ($5 \times 10^8$ cfu/100 µl PBS/mouse).

Mice.

Six to 8-week-old C57BL/6, and IL-10$^{-/-}$ (C57BL/6 background) mice were purchased from Jackson Laboratories (Bar Harbor, Me.), and Germantown, N.Y. Mice were maintained in microisolator cages under specific pathogen-free, Helicobacter-free conditions at the animal care facility at the Northwestern University. We did not observe any spontaneous signs of inflammation in the colons of IL-10$^{-/-}$ mice. Experiments were performed in an accredited establishment according to NIH guidelines in the Guide for Care and Use of Laboratory Animals (NIH-72-23), and animal protocols were approved by the local ethics committee.

Phosphoglycerol Transferase Targeting.

A mutant strain of *L. acidophilus* NCK56 was constructed with a deletion of phosphoglycerol transferase (LBA0447) using standard integration and excision methods, tools and strains (Pfeiler E A & Klaenhammer T R (2009) *Appl Environ Microbiol* 75(18):6013-6016, Russell W M & Klaenhammer T R (2001) *Appl Environ Microbiol* 67(9):4361-4364). A pORI28 deletion vector was constructed containing two targeting fragments, Del1_SphI and Del2_BglII that flank LBA0447. Following a double crossover integration and excision event, NCK2025 was recovered that harbored a 1,984 bp deletion of LBA0447 in the genome. PCR amplicons and DNA sequencing over the LBA0447 region in NCK2025 confirmed the loss of ~2 kbp and revealed no additional mutations in the genes surrounding the deletion.

LTA Biochemical Analysis.

*L. acidophilus* NCK56 ($5 \times 10^8$/cfu/10 ml) and NCK2025 ($5 \times 10^8$/cfu/10 ml) were propagated from frozen stocks (−80° C.) in deMan, Rogosa, and Sharpe broth (MRS, Difco, Lawrence, Kans.) without ERM at 37° C. Subsequently, the expression of LTA in NCK56 and NCK2025 was analyzed as described previously (Morath S, Geyer A, & Hartung T (2001) *J Exp Med* 193(3):393-397). Briefly, the frozen extracts of both strains NCK56 and NCK2025 were dissolved in the citrate buffer (0.05 M) at pH 4.7, followed by syndication for 15 minutes. The bacteria lysates (30 ml) was mixed with an equal volume of n-butanol under stirring for 20 minutes at room temperature. Subsequently, centrifugation (17, 200×g) for 40 minutes aqueous phase was collected before the addition of fresh citrate buffer for a second extraction. This re-extraction was conducted twice, and three aqueous phases were pooled and lyophilized. After resuspension of the samples in chromatography start buffer (35 ml, 15% n-propanol in 0.1 M ammonium acetate, pH 4.7), all samples were centrifuged (26,900×g for 1 h) and filtered (0.2 µm). Lyophilized material from both bacterial strains was dissolved in 0.7% trifluoracetic acid and 0.45 mg of extract from each strain was analyzed by HPLC. Chromatographs were obtained by continuously monitoring absorbance at 260 nm.

Cell Culture.

Mice femurs were removed and mechanically purified from surrounding tissues and bone marrow was flushed using cold PBS. Cells were treated with Tris-buffered ammonium chloride to lyse erythrocytes. Subsequently, B cells, T cells, IA$^+$ cells, and Gr-1$^+$ granulocytes were removed positively by specific antibodies against CD19, CD3, MHC II and Gr-1 (PharMingen, San Diego, Calif.). The remaining cells were I-A$^-$, and were cultured in RPMI 1640 complete medium plus 10% fetal bovine serum (FBS) with mouse GM-CSF alone (25 ng/ml) in 6-well plates for 6 days. Every other day cultures were fed with fresh media containing GM-CSF. On day 6, cells were harvested and used for different experiments. To study T cell activation and proliferation, NCK56 or NCK2025 was administrated (at $5 \times 10^8$ CFU/100 µl/mouse) to C57BL/6 mice for four consecutive days. A week later, mice were sacrificed to isolate mesenteric LNs of each group of mice. Mesenteric T cells were enriched by negative magnetic bead depletion. To assay T cell activation and proliferation, NCK56 or NCK2025 treated and untreated DCs ($10^4$/well of 96-well plate) were cultured at graded doses with isolated mesenteric LN CD4$^+$ T cells ($10^5$/well) for 5 days in serum free media. Afterwards, 25 µA of each well of 96-well plate were harvested and frozen for cytokine analysis. Cells were then pulsed for the last 16 h with 0.5 µCi [$^3$H]thymidine per well (New England Nuclear) (Pulendran B, et al. (2004) *Eur J Immunol* 34(1):66-73). In some experiments anti-IL-10 antibody (final concentration 100 ng/ml) was used in DC:T cell co cultures, respectively.

DSS-Induced Colitis.

For vaccination/prevention studies, groups of C57BL/6 mice (10 mice/group) were inoculated orally with NCK56 or NCK2025 ($5 \times 10^8$ cfu/100 µl PBS/mouse) for four consecutive days. These groups of mice and the control mice received one 6-day cycle of 3% DSS in drinking water, followed by 1 day of regular drinking water and then were sacrificed on day 8. Acute colitis was observed after the first cycle of DSS in the non-inoculated group. Disease progression, including weight lost, diarrhea and fecal hemoccult blood positivity (FOB), was monitored throughout the study. Thereafter, mice were sacrificed and colon cross-sectional Swiss rolls were fixed in 10% formaldehyde and embedded in paraffin. Tissue sections (4 µm) were stained with hematoxyhylin and eosin (H&E), and blindly scored as described previously (Cooper H S, et al. (1993) *Lab Invest* 69(2):238-249, Murthy S N, et al. (1993) *Dig Dis Sci* 38(9):1722-1734). The grading based on a scale from 0 to 28 takes into account the degree of inflammatory infiltrate, the presence of erosion, ulceration, or necrosis, and the depth and surface extension of the lesion. For treatment studies, 3 groups of C57BL/6 mice (10/group) first received a 5-day cycle of 3% DSS to initiate colitis, and 2 of the groups were subsequently treated via oral gavage with NCK56 or NCK2025 ($5 \times 10^8$ cfu/100 µA PBS/mouse) for four consecutive days. Disease progression was monitored to day 13 of the protocol when mice were sacrificed, and colons assessed as above.

Colonic Tissue Cultures.

Colonic tissue cultures were performed as previously described (Sellon R K, et al. (1998) *Infect Immun* 66(11): 5224-5231). Briefly, colonic tissues of each mouse group treated with *L. acidophilus* strains before or after 3% DSS application were thoroughly cleaned with cold PBS. Tissues were cut into 1-cm pieces and shaken in complete RPMI 1640 containing gentamicin (50 µg/ml) for 30 minutes at 280 rpm. Colonic tissues were cultured in RPMI 1640 medium supplemented with 5% fetal calf serum (FCS), 50 µg/ml gentamicin, and 1% penicillin/streptomycin/amphotericin B for 18 hours at 37° C. Supernatants were then collected and stored at −80° C. before use for cytokine analysis.

IL-10$^{-/-}$ Colitis.

Groups of C57BL/6 IL-10$^{-/-}$ (10/group) were transferred from pathogen free housing to conventional housing and allowed to acclimate for 1 week. Mice were then inoculated with NCK56 or NCK2025 ($5 \times 10^8$ cfu/100 µl PBS/mouse) for four consecutive days and then fed low dose piroxicam for 1 week, followed by high dose piroxicam for 1 week to accelerate and synchronize the onset of colitis, as previously described (Berg D J, et al. (2002) *Gastroenterology* 123(5): 1527-1542). After 2 weeks on standard chow (day 28), mice were sacrificed, and colon cross-sectional Swiss rolls were fixed in 10% formaldehyde and embedded in paraffin. Tissue sections (4 µm) were stained with H&E, and blindly scored on a scale from 0 to 4, as described previously (Berg D J, et al. (2002) *Gastroenterology* 123(5):1527-1542).

Flow Cytometry.

*L. acidophilus* treated- and untreated-DCs ($5 \times 10^5$) were incubated with surface marker monoclonal antibodies for 30 minutes at 4° C., washed extensively with PBS plus 0.1% FCS, fixed with 0.1% paraformaldehyde, and analyzed by a FACSCalibur four-laser cytometry by using standard CELLQUEST acquisition analysis software (Becton Dickinson). At least $10^4$ gated events per condition were acquired. In some experiment to derive colonic lymphocytes groups of mice (5 mice/group) were inoculated with NCK56 or NCK2025 ($5 \times 10^8$ cfu/100 µl of sterile PBS/mouse) for 4 consecutive days. Mice were sacrificed; colons cleaned and single cells were isolated from the lamina propria as previously described (Haddad W, et al. (2003) *J Exp Med* 198(3): 369-377). Lymphocytes were enriched using Percol and stained with anti-CD4 FITC, CD25 APC antibodies and 7AAD. Subsequently, stained cells were fixed, permeabilized, stained with anti-FoxP3 PE or isotype antibodies and analyzed by FACSCalibur.

Real Time PCR.

Total RNA was isolated from bone marrow DCs using the RNeasy Mini Kit (Qiagen, MD). The high capacity cDNA reverse transcription kit was used to synthesize cDNA from 5 ug RNA and expression of TLR1 and TLR2 genes determined by real time semi-quantitative PCR using the ABI 7500 real-time PCR system with Power Syber green 2×PCR master mix (Applied Biosystems, Foster City, Calif.). Primers for TLR1 (Forward-TTAATGAGTGTTTGTGAATGCAGTTG (SEQ ID NO: 17); Reverse-GAGCATTGCCACATGGGTATAG (SEQ ID NO: 18)) and TLR2 (Forward-CAAAGCGT-CAAATCTCAGAGGAT (SEQ ID NO: 19); Reverse-ACAC-CCCAGAAGCATCACATG (SEQ ID NO: 20)) were selected for regions spanning intron junctions to exclude amplification of genomic DNA. Results reflect the fold increase relative to the control sample using the ddCT method using Gapdh as the endogenous control (Forward-GTCGTG-GATCTGACGTGCC (SEQ ID NO: 21); Reverse-TGCCT-GCTTCACCACCTTC (SEQ ID NO: 22)).

Low Density cDNA Microarray:

Colonic distal and proximal regions of each group of mice (5×/group) that were treated with DSS alone, NCK56-DSS or NCK2025-DSS were flushed with PBS, and immediately immersed in RNALater (Qiagen, Md.) for RNA stabilization. RNA was extracted with the RNeasy Mini Kit (Qiagen, Md.) and quality assessed using Agilent Nanochip Bioanalysis (Agilent, Santa Clara, Calif.). All samples used had RNA Integrity Numbers (RIN) greater than 7. Reverse transcription and hybridization for the microarrays was carried out as described by the manufacturer (Eppendorf DualChip microarray, Germany). Briefly, 6 ug of RNA was reverse transcribed by first incubating the samples with Oligo(dT)$_{12\text{-}18}$ Primer (Invitrogen) at 70° C. for 10 minutes followed by the addition of the RT mix (Superscript III, dNTPs (Invitrogen), biotin-labeled ATP and CTP (Perkin Elmer, Waltham, Mass.) and incubation at 42° C. for 90 minutes then 70° C. for 15 minutes. RNase H was added and the samples incubated at 37° C. for 20 minutes followed by 95° C. for 3 minutes to terminate the reaction. Resulting cDNA was loaded into the hybridization chamber and incubated overnight at 60° C. mixing at 1400 rpm in an Eppendorf thermomixer. Slides were washed and RNA levels determined by detection of biotin incorporation using the Silverquant detection system as described by the manufacturer (Eppendorf, Germany). Analysis was performed by comparison of samples to a control from the same colon region using Silverquant analysis software (Eppendorf, Germany).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant or isolated bacterium having been genetically modified to decrease the display of lipoteichoic acid (LTA) on the surface of said bacterium, wherein the genetic modification comprises deletion or substitution of at least one base pair such that the expression of at least one polynucleotide encoding a phosphoglycerol transferase is decreased,
wherein said polynucleotide encoding a phosphoglycerol transferase comprises a nucleotide sequence having at least 85% sequence identity to the nucleic acid sequence as set forth in SEQ ID NO:1; and
wherein decreasing the expression of the at least one polynucleotide encoding a phosphoglycerol transferase decreases the display of LTA on the surface of the bacterium.

2. The recombinant or isolated bacterium of claim 1, wherein said polynucleotide encoding a phosphoglycerol transferase comprises a nucleotide sequence having at least 90% sequence identity to the nucleic acid sequence as set forth in SEQ ID NO:1.

3. The recombinant or isolated bacterium of claim 1, wherein said recombinant or isolated bacterium is a probiotic bacterium.

4. The recombinant or isolated bacterium of claim 3, wherein said probiotic bacterium is a lactic acid bacterium.

5. The recombinant or isolated bacterium of claim 4, wherein said lactic acid bacterium is a *Lactobacillus*.

6. The recombinant bacterium of claim 5, wherein said *Lactobacillus* is *Lactobacillus acidophilus*.

7. The recombinant or isolated bacterium of claim 6, wherein said genetic modification was performed on *Lactobacillus acidophilus* NCFM.

8. The recombinant or isolated bacterium of claim 6, wherein said *Lactobacillus acidophilus* is *Lactobacillus acidophilus* NCK2025, deposited under ATCC accession number PTA-11587.

9. A method of making a recombinant or isolated bacterium, said method comprising genetically modifying a bacterium to decrease the display of lipoteichoic acid (LTA) on the surface of said bacterium,
wherein the genetic modification comprises deletion or substitution of at least one base pair such that the expression of at least one polynucleotide encoding a phosphoglycerol transferase is decreased,
wherein said polynucleotide encoding a phosphoglycerol transferase comprises a nucleotide sequence having at least 85% sequence identity to the nucleic acid sequence as set forth in SEQ ID NO:1; and
wherein decreasing the expression of the at least one polynucleotide encoding a phosphoglycerol transferase decreases the display of LTA on the surface of the bacterium.

10. The method of claim 9, wherein said recombinant or isolated bacterium has been genetically modified to decrease the expression of a polynucleotide comprising a nucleotide sequence having at least 90% sequence identity to the nucleotide sequence as set forth in SEQ ID NO:1.

11. The method of claim 9, wherein said recombinant bacterium is a probiotic bacterium.

12. The method of claim 11, wherein said probiotic bacterium is a lactic acid bacterium.

13. A pharmaceutical composition comprising the recombinant or isolated bacterium according to claim 1.

14. The recombinant or isolated bacterium of claim 1, wherein said polynucleotide encoding a phosphoglycerol transferase comprises the nucleotide sequence as set forth in SEQ ID NO: 1.

15. The recombinant or isolated bacterium of claim 1, wherein said deletion or substitution comprises a deletion or substitution of at least one base pair of said polynucleotide encoding a phosphoglycerol transferase.

16. The method of claim 9, wherein said polynucleotide encoding a phosphoglycerol transferase comprises the nucleotide sequence as set forth in SEQ ID NO: 1.

17. The method of claim 9, wherein said deletion or substitution comprises a deletion or substitution of at least one base pair of said polynucleotide encoding a phosphoglycerol transferase.

* * * * *

SEQUENCE LISTING

```
<160> NUMBER OF SEQ ID NOS: 22

<210> SEQ ID NO 1
<211> LENGTH: 2058
<212> TYPE: DNA
<213> ORGANISM: Lactobacillus acidophilus
<220> FEATURE:
<221> NAME/KEY: misc_feature
<222> LOCATION: (1)...(2058)
<223> OTHER INFORMATION: LBA0447  Phosphoglycerol transferase
      GenBank Accession No. AAV42337
<220> FEATURE:
<221> NAME/KEY: CDS
<222> LOCATION: (1)...(2058)

<400> SEQUENCE: 1 atg gaa cgt acc aaa tct ttt ttt aaa tgg ttg acg caa act aag ctg        48
Met Glu Arg Thr Lys Ser Phe Phe Lys Trp Leu Thr Gln Thr Lys Leu
 1               5                  10                  15 gga ttt ttt aca ata gtt tta gta ttg ttt tgg cta aaa aca tat tat        96
Gly Phe Phe Thr Ile Val Leu Val Leu Phe Trp Leu Lys Thr Tyr Tyr
             20                  25                  30 att tat tta act aag ttc aac ttg ggt gca gtt ggt cct atg cag caa       144
Ile Tyr Leu Thr Lys Phe Asn Leu Gly Ala Val Gly Pro Met Gln Gln
         35                  40                  45 ttt ttg ctt tta att aac cct att cca tca ggg atg ctg cta cta ggt       192
Phe Leu Leu Leu Ile Asn Pro Ile Pro Ser Gly Met Leu Leu Leu Gly
     50                  55                  60 att ggc cta ttt ttt aag gga cga aaa tct tat tgg att att ctg ata       240
Ile Gly Leu Phe Phe Lys Gly Arg Lys Ser Tyr Trp Ile Ile Leu Ile
 65                  70                  75                  80 atc gat ttt tta tta acg ctg tgg ctt ttt tct aat att tta tat tat       288
Ile Asp Phe Leu Leu Thr Leu Trp Leu Phe Ser Asn Ile Leu Tyr Tyr
                 85                  90                  95 cga gaa ttt tct aat ttc ttg tct ttt tca att att aag aca tca gga       336
Arg Glu Phe Ser Asn Phe Leu Ser Phe Ser Ile Ile Lys Thr Ser Gly
            100                 105                 110 tcg aca tcc gat aat ctg gga aaa agt att gca gga ata act tta gca       384
Ser Thr Ser Asp Asn Leu Gly Lys Ser Ile Ala Gly Ile Thr Leu Ala
        115                 120                 125 agt gat ttt tta gca ttt ttg gat att gca gtt att att gcg tta tta       432
Ser Asp Phe Leu Ala Phe Leu Asp Ile Ala Val Ile Ile Ala Leu Leu
    130                 135                 140 gct act aaa gtt att aaa atg gat gtg cgt cca tta aag tta aaa gtg       480
Ala Thr Lys Val Ile Lys Met Asp Val Arg Pro Leu Lys Leu Lys Val
145                 150                 155                 160 agt ctt tta att gaa ttt ttg gca ctt agt tta atg gga ctt aat tta       528
Ser Leu Leu Ile Glu Phe Leu Ala Leu Ser Leu Met Gly Leu Asn Leu
                165                 170                 175
```

-continued

| | | |
|---|---|---|
| ttg atg gcc caa aaa gat aga tca ggt ctt tta act aga acc ttt gat<br>Leu Met Ala Gln Lys Asp Arg Ser Gly Leu Leu Thr Arg Thr Phe Asp<br>          180                        185                            190 | 576 |
| aat aac tat att gtt aaa tat cta gga att aat gaa tac gct att tat<br>Asn Asn Tyr Ile Val Lys Tyr Leu Gly Ile Asn Glu Tyr Ala Ile Tyr<br>          195                        200                          205 | 624 |
| gat gga tat aaa aca gcc caa aca agc gcc caa atg gct aag gca aac<br>Asp Gly Tyr Lys Thr Ala Gln Thr Ser Ala Gln Met Ala Lys Ala Asn<br>210                        215                        220 | 672 |
| gta tct gat tta aaa tct gta cgt aat tat tta aat gca aac aag gta<br>Val Ser Asp Leu Lys Ser Val Arg Asn Tyr Leu Asn Ala Asn Lys Val<br>225                        230                                    240 | 720 |
| aaa cct aat cca gaa tat acg ggt gta gca aaa gga aaa aac gtt tta<br>Lys Pro Asn Pro Glu Tyr Thr Gly Val Ala Lys Gly Lys Asn Val Leu<br>                    245                        250                        255 | 768 |
| gtt att cac ctt gaa agt ttt caa caa ttt tta att ggc tat aaa tgg<br>Val Ile His Leu Glu Ser Phe Gln Gln Phe Leu Ile Gly Tyr Lys Trp<br>                    260                        265                        270 | 816 |
| aag ggt aaa gaa gta aca cct aat tta aat aaa ata tat cat caa aaa<br>Lys Gly Lys Glu Val Thr Pro Asn Leu Asn Lys Ile Tyr His Gln Lys<br>        275                        280                        285 | 864 |
| gat acg att agc ttt gat aat ttc ttt aac cag gta gga caa ggt aaa<br>Asp Thr Ile Ser Phe Asp Asn Phe Phe Asn Gln Val Gly Gln Gly Lys<br>290                        295                        300 | 912 |
| act tca gat gct gaa atg atg tta gaa aat tca tta tat ggt ttg cag<br>Thr Ser Asp Ala Glu Met Met Leu Glu Asn Ser Leu Tyr Gly Leu Gln<br>305                        310                        315                        320 | 960 |
| tct ggg tca gct atg tct act tat ggc acg tca aat acg ttt gaa agt<br>Ser Gly Ser Ala Met Ser Thr Tyr Gly Thr Ser Asn Thr Phe Glu Ser<br>                    325                        330                        335 | 1008 |
| gca cca gcg att ttg cac caa caa gca ggt tat act act gca gta atg<br>Ala Pro Ala Ile Leu His Gln Gln Ala Gly Tyr Thr Thr Ala Val Met<br>                    340                        345                        350 | 1056 |
| cat ggt ggt gca gga tcg ttc tgg aat aga aat aat gca tat aaa tca<br>His Gly Gly Ala Gly Ser Phe Trp Asn Arg Asn Asn Ala Tyr Lys Ser<br>        355                        360                        365 | 1104 |
| ttt ggt tat caa tat ttt atg cca tta tca ttt tat gaa aat aaa ccc<br>Phe Gly Tyr Gln Tyr Phe Met Pro Leu Ser Phe Tyr Glu Asn Lys Pro<br>370                        375                        380 | 1152 |
| agc tat tat att gga tat ggt tta aaa gat aag att ttc ttt gat caa<br>Ser Tyr Tyr Ile Gly Tyr Gly Leu Lys Asp Lys Ile Phe Phe Asp Gln<br>385                        390                        395                        400 | 1200 |
| tca att aaa tat att gaa cgt tta cca cag cca ttt tat tta aag atg<br>Ser Ile Lys Tyr Ile Glu Arg Leu Pro Gln Pro Phe Tyr Leu Lys Met<br>                    405                        410                        415 | 1248 |
| atc aca gta act aat cat tat cca tac gat att gac aag aag aat caa<br>Ile Thr Val Thr Asn His Tyr Pro Tyr Asp Ile Asp Lys Lys Asn Gln<br>                  420                        425                        430 | 1296 |
| tcc att gct aag act aat act ggg gat gaa act gtt gat ggt tac gtt<br>Ser Ile Ala Lys Thr Asn Thr Gly Asp Glu Thr Val Asp Gly Tyr Val<br>                  435                        440                        445 | 1344 |
| caa aca gcg cat tat ctt gat caa gca att gga gaa cta atg agc tgg<br>Gln Thr Ala His Tyr Leu Asp Gln Ala Ile Gly Glu Leu Met Ser Trp<br>450                        455                        460 | 1392 |
| atg aag aag act gga cta gat aaa aag aca ttg att gtc ttt tat ggc<br>Met Lys Lys Thr Gly Leu Asp Lys Lys Thr Leu Ile Val Phe Tyr Gly<br>465                        470                        475                        480 | 1440 |
| gat cac tat ggt att tct gga aat cac cat aaa gct agt gca caa ctt<br>Asp His Tyr Gly Ile Ser Gly Asn His His Lys Ala Ser Ala Gln Leu | 1488 |

```
                     485                 490                 495
ctt aag aaa aaa tca ttt aat gat ttt gat aat ttg cag ttt caa aga    1536
Leu Lys Lys Lys Ser Phe Asn Asp Phe Asp Asn Leu Gln Phe Gln Arg
            500                 505                 510 gtg cct tta atg ttt cat atg aaa gga tta aag ggt gga ata aat cat    1584
Val Pro Leu Met Phe His Met Lys Gly Leu Lys Gly Gly Ile Asn His
        515                 520                 525 act tat ggt ggt gaa att gat gtt tta cca act ttg tta aat tta ctc    1632
Thr Tyr Gly Gly Glu Ile Asp Val Leu Pro Thr Leu Leu Asn Leu Leu
    530                 535                 540 ggt att aaa gat agc gat act att caa ttt ggc tac gat tta ctt agc    1680
Gly Ile Lys Asp Ser Asp Thr Ile Gln Phe Gly Tyr Asp Leu Leu Ser
545                 550                 555                 560 aaa aac gca ccc caa att gta gcc caa aga aat gga gac ttt att aca    1728
Lys Asn Ala Pro Gln Ile Val Ala Gln Arg Asn Gly Asp Phe Ile Thr
                565                 570                 575 cca gaa tat tca aaa gtt ggt agc gat tat tat tac act aag act ggt    1776
Pro Glu Tyr Ser Lys Val Gly Ser Asp Tyr Tyr Tyr Thr Lys Thr Gly
            580                 585                 590 aaa aga att aag cct aat aag aaa tta aaa gct gaa ttg acg gca att    1824
Lys Arg Ile Lys Pro Asn Lys Lys Leu Lys Ala Glu Leu Thr Ala Ile
        595                 600                 605 tct aac act gtg aca acg cag ctt tct tta tca gat cgt gta att aac    1872
Ser Asn Thr Val Thr Thr Gln Leu Ser Leu Ser Asp Arg Val Ile Asn
    610                 615                 620 ggt aat tta tta cgg ttt tat cgt cct aag tgg ttt act aag gtt aag    1920
Gly Asn Leu Leu Arg Phe Tyr Arg Pro Lys Trp Phe Thr Lys Val Lys
625                 630                 635                 640 cca aaa gac tac gat tat aat aag gaa cca tcg tta aaa cgt tta ttt    1968
Pro Lys Asp Tyr Asp Tyr Asn Lys Glu Pro Ser Leu Lys Arg Leu Phe
                645                 650                 655 aat gat cca agt aaa acg tct cta tgg tat caa aat cat aaa aag acg    2016
Asn Asp Pro Ser Lys Thr Ser Leu Trp Tyr Gln Asn His Lys Lys Thr
            660                 665                 670 acg caa aaa gat ttt aaa act gat gcg cct gag ttg aaa aaa            2058
Thr Gln Lys Asp Phe Lys Thr Asp Ala Pro Glu Leu Lys Lys
        675                 680                 685

<210> SEQ ID NO 2
<211> LENGTH: 686
<212> TYPE: PRT
<213> ORGANISM: Lactobacillus acidophilus

<400> SEQUENCE: 2

Met Glu Arg Thr Lys Ser Phe Phe Lys Trp Leu Thr Gln Thr Lys Leu
1               5                   10                  15

Gly Phe Phe Thr Ile Val Leu Val Leu Phe Trp Leu Lys Thr Tyr Tyr
            20                  25                  30

Ile Tyr Leu Thr Lys Phe Asn Leu Gly Ala Val Gly Pro Met Gln Gln
        35                  40                  45

Phe Leu Leu Ile Asn Pro Ile Pro Ser Gly Met Leu Leu Leu Gly
    50                  55                  60

Ile Gly Leu Phe Phe Lys Gly Arg Lys Ser Tyr Trp Ile Ile Leu Ile
65                  70                  75                  80

Ile Asp Phe Leu Leu Thr Leu Trp Leu Phe Ser Asn Ile Leu Tyr Tyr
                85                  90                  95

Arg Glu Phe Ser Asn Phe Leu Ser Phe Ser Ile Ile Lys Thr Ser Gly
            100                 105                 110
```

```
Ser Thr Ser Asp Asn Leu Gly Lys Ser Ile Ala Gly Ile Thr Leu Ala
        115                 120                 125
Ser Asp Phe Leu Ala Phe Leu Asp Ile Ala Val Ile Ala Leu Leu
130                 135                 140
Ala Thr Lys Val Ile Lys Met Asp Val Arg Pro Leu Lys Leu Lys Val
145                 150                 155                 160
Ser Leu Leu Ile Glu Phe Leu Ala Leu Ser Leu Met Gly Leu Asn Leu
                165                 170                 175
Leu Met Ala Gln Lys Asp Arg Ser Gly Leu Leu Thr Arg Thr Phe Asp
            180                 185                 190
Asn Asn Tyr Ile Val Lys Tyr Leu Gly Ile Asn Glu Tyr Ala Ile Tyr
        195                 200                 205
Asp Gly Tyr Lys Thr Ala Gln Thr Ser Ala Gln Met Ala Lys Ala Asn
210                 215                 220
Val Ser Asp Leu Lys Ser Val Arg Asn Tyr Leu Asn Ala Asn Lys Val
225                 230                 235                 240
Lys Pro Asn Pro Glu Tyr Thr Gly Val Ala Lys Gly Lys Asn Val Leu
                245                 250                 255
Val Ile His Leu Glu Ser Phe Gln Gln Phe Leu Ile Gly Tyr Lys Trp
            260                 265                 270
Lys Gly Lys Glu Val Thr Pro Asn Leu Asn Lys Ile Tyr His Gln Lys
        275                 280                 285
Asp Thr Ile Ser Phe Asp Asn Phe Phe Asn Gln Val Gly Gln Gly Lys
290                 295                 300
Thr Ser Asp Ala Glu Met Met Leu Glu Asn Ser Leu Tyr Gly Leu Gln
305                 310                 315                 320
Ser Gly Ser Ala Met Ser Thr Tyr Gly Thr Ser Asn Thr Phe Glu Ser
                325                 330                 335
Ala Pro Ala Ile Leu His Gln Ala Gly Tyr Thr Thr Ala Val Met
            340                 345                 350
His Gly Gly Ala Gly Ser Phe Trp Asn Arg Asn Asn Ala Tyr Lys Ser
        355                 360                 365
Phe Gly Tyr Gln Tyr Phe Met Pro Leu Ser Phe Tyr Glu Asn Lys Pro
370                 375                 380
Ser Tyr Tyr Ile Gly Tyr Gly Leu Lys Asp Lys Ile Phe Phe Asp Gln
385                 390                 395                 400
Ser Ile Lys Tyr Ile Glu Arg Leu Pro Gln Pro Phe Tyr Leu Lys Met
                405                 410                 415
Ile Thr Val Thr Asn His Tyr Pro Tyr Asp Ile Asp Lys Lys Asn Gln
            420                 425                 430
Ser Ile Ala Lys Thr Asn Thr Gly Asp Glu Thr Val Asp Gly Tyr Val
        435                 440                 445
Gln Thr Ala His Tyr Leu Asp Gln Ala Ile Gly Glu Leu Met Ser Trp
450                 455                 460
Met Lys Lys Thr Gly Leu Asp Lys Lys Thr Leu Ile Val Phe Tyr Gly
465                 470                 475                 480
Asp His Tyr Gly Ile Ser Gly Asn His His Lys Ala Ser Ala Gln Leu
                485                 490                 495
Leu Lys Lys Lys Ser Phe Asn Asp Phe Asn Leu Gln Phe Gln Arg
            500                 505                 510
Val Pro Leu Met Phe His Met Lys Gly Leu Lys Gly Gly Ile Asn His
        515                 520                 525
Thr Tyr Gly Gly Glu Ile Asp Val Leu Pro Thr Leu Leu Asn Leu Leu
```

-continued

```
                530             535             540
Gly Ile Lys Asp Ser Asp Thr Ile Gln Phe Gly Tyr Asp Leu Leu Ser
545                 550                 555                 560

Lys Asn Ala Pro Gln Ile Val Ala Gln Arg Asn Gly Asp Phe Ile Thr
                565                 570                 575

Pro Glu Tyr Ser Lys Val Gly Ser Asp Tyr Tyr Thr Lys Thr Gly
            580                 585                 590

Lys Arg Ile Lys Pro Asn Lys Lys Leu Lys Ala Glu Leu Thr Ala Ile
                595                 600                 605

Ser Asn Thr Val Thr Thr Gln Leu Ser Leu Ser Asp Arg Val Ile Asn
610                 615                 620

Gly Asn Leu Leu Arg Phe Tyr Arg Pro Lys Trp Phe Thr Lys Val Lys
625                 630                 635                 640

Pro Lys Asp Tyr Asp Tyr Asn Lys Glu Pro Ser Leu Lys Arg Leu Phe
                645                 650                 655

Asn Asp Pro Ser Lys Thr Ser Leu Trp Tyr Gln Asn His Lys Lys Thr
                660                 665                 670

Thr Gln Lys Asp Phe Lys Thr Asp Ala Pro Glu Leu Lys Lys
            675                 680                 685

<210> SEQ ID NO 3
<211> LENGTH: 1161
<212> TYPE: DNA
<213> ORGANISM: Lactobacillus acidophilus
<220> FEATURE:
<221> NAME/KEY: misc_feature
<222> LOCATION: (1)...(1161)
<223> OTHER INFORMATION: LBA0444 Glycosyltransferase
      GenBank Accession No. AAV42334
<220> FEATURE:
<221> NAME/KEY: CDS
<222> LOCATION: (1)...(1161)

<400> SEQUENCE: 3 atg aat att ggt ctt tat acc gat aca tat ttt ccc caa ata agt ggc     48
Met Asn Ile Gly Leu Tyr Thr Asp Thr Tyr Phe Pro Gln Ile Ser Gly
1               5                   10                  15 gta gct act tct att agg acg cta aaa gat gcg ctt gaa aga cag ggg     96
Val Ala Thr Ser Ile Arg Thr Leu Lys Asp Ala Leu Glu Arg Gln Gly
                20                  25                  30 cat aat gta ttt att ttt aca act aca gat cca aat gta gaa aag ggc    144
His Asn Val Phe Ile Phe Thr Thr Thr Asp Pro Asn Val Glu Lys Gly
            35                  40                  45 act gtt gag cca aat gtt ttt cgt ttt agc agt ata cct ttt gtt tca    192
Thr Val Glu Pro Asn Val Phe Arg Phe Ser Ser Ile Pro Phe Val Ser
        50                  55                  60 ttc aca gat cgt aga att gca ttt aga ggc tta ttt gaa gca act aag    240
Phe Thr Asp Arg Arg Ile Ala Phe Arg Gly Leu Phe Glu Ala Thr Lys
65                  70                  75                  80 gta gct aag gaa gta aat ttg gat att gta cat aca caa act gaa ttt    288
Val Ala Lys Glu Val Asn Leu Asp Ile Val His Thr Gln Thr Glu Phe
                85                  90                  95 gct tta ggt aca att ggc aaa tat gta gcc cac caa tta gat att cct    336
Ala Leu Gly Thr Ile Gly Lys Tyr Val Ala His Gln Leu Asp Ile Pro
                100                 105                 110 gca att cat act tat cac aca atg tat gaa gat tat ttg cat tat att    384
Ala Ile His Thr Tyr His Thr Met Tyr Glu Asp Tyr Leu His Tyr Ile
            115                 120                 125 tta aat ggt cac tta ttg cga cca tat cat gtt aaa caa ttc gta aaa    432
Leu Asn Gly His Leu Leu Arg Pro Tyr His Val Lys Gln Phe Val Lys
```

```
agc tat tta aaa aat atg gat ggc tgt att gcc cca agt gga cgt gta      480
Ser Tyr Leu Lys Asn Met Asp Gly Cys Ile Ala Pro Ser Gly Arg Val
145                 150                 155                 160 gaa gat ttg tta aag cga tat ggc gtg caa att cca att agg gta att      528
Glu Asp Leu Leu Lys Arg Tyr Gly Val Gln Ile Pro Ile Arg Val Ile
                165                 170                 175 cct act gga gta gat ttg cag gga atg aat ggc gat gct gaa cgt gat      576
Pro Thr Gly Val Asp Leu Gln Gly Met Asn Gly Asp Ala Glu Arg Asp
            180                 185                 190 gta cgt cag gaa tta gga atc gac aaa gat gct cct gta att tta act      624
Val Arg Gln Glu Leu Gly Ile Asp Lys Asp Ala Pro Val Ile Leu Thr
        195                 200                 205 tta agt aga att gca gca gaa aag aaa ata aat cat att ctt aat gtg      672
Leu Ser Arg Ile Ala Ala Glu Lys Lys Ile Asn His Ile Leu Asn Val
    210                 215                 220 atg cca gca att gta gaa gaa ttt cca aat att aaa ttt gta att gcc      720
Met Pro Ala Ile Val Glu Glu Phe Pro Asn Ile Lys Phe Val Ile Ala
225                 230                 235                 240 ggt gat gga cct gat gtt aaa gtg ctg aaa gaa caa gtt gaa cgt tta      768
Gly Asp Gly Pro Asp Val Lys Val Leu Lys Glu Gln Val Glu Arg Leu
                245                 250                 255 act tta gaa gat tat gtt tta ttt gtc ggt aac gtt gat cat gga gat      816
Thr Leu Glu Asp Tyr Val Leu Phe Val Gly Asn Val Asp His Gly Asp
            260                 265                 270 gta ggc aat tat tat cga atg gcc gat ctt ttt gtt tct gcc agt gac      864
Val Gly Asn Tyr Tyr Arg Met Ala Asp Leu Phe Val Ser Ala Ser Asp
        275                 280                 285 act gaa acc caa ggt ctt act tat ata gaa gct ttg gct gca ggt aca      912
Thr Glu Thr Gln Gly Leu Thr Tyr Ile Glu Ala Leu Ala Ala Gly Thr
    290                 295                 300 cca tgt gta gtt tac gac act gat tac act gaa aat att ttt gat aat      960
Pro Cys Val Val Tyr Asp Thr Asp Tyr Thr Glu Asn Ile Phe Asp Asn
305                 310                 315                 320 gat gtc ttt gga cgt act ttt gtt aca cag aag gaa atg ttg caa gaa     1008
Asp Val Phe Gly Arg Thr Phe Val Thr Gln Lys Glu Met Leu Gln Glu
                325                 330                 335 att att gaa tta ttg aaa aaa gga cac aat aga att cca caa gat ctt     1056
Ile Ile Glu Leu Leu Lys Lys Gly His Asn Arg Ile Pro Gln Asp Leu
            340                 345                 350 tta caa aat aaa ttg cag aag att tca tcg gag caa ttt gct aca aat     1104
Leu Gln Asn Lys Leu Gln Lys Ile Ser Ser Glu Gln Phe Ala Thr Asn
        355                 360                 365 gtc cat gat ttt tat aaa tac gcg att gat cat tat caa cct aaa cat     1152
Val His Asp Phe Tyr Lys Tyr Ala Ile Asp His Tyr Gln Pro Lys His
    370                 375                 380 gaa gaa ata                                                         1161
Glu Glu Ile
385

<210> SEQ ID NO 4
<211> LENGTH: 387
<212> TYPE: PRT
<213> ORGANISM: Lactobacillus acidophilus

<400> SEQUENCE: 4

Met Asn Ile Gly Leu Tyr Thr Asp Thr Tyr Phe Pro Gln Ile Ser Gly
1               5                   10                  15

Val Ala Thr Ser Ile Arg Thr Leu Lys Asp Ala Leu Glu Arg Gln Gly
            20                  25                  30
```

His Asn Val Phe Ile Phe Thr Thr Thr Asp Pro Asn Val Glu Lys Gly
          35                  40                  45

Thr Val Glu Pro Asn Val Phe Arg Phe Ser Ser Ile Pro Phe Val Ser
 50                  55                  60

Phe Thr Asp Arg Arg Ile Ala Phe Arg Gly Leu Phe Glu Ala Thr Lys
 65                  70                  75                  80

Val Ala Lys Glu Val Asn Leu Asp Ile Val His Thr Gln Thr Glu Phe
                 85                  90                  95

Ala Leu Gly Thr Ile Gly Lys Tyr Val Ala His Gln Leu Asp Ile Pro
             100                 105                 110

Ala Ile His Thr Tyr His Thr Met Tyr Glu Asp Tyr Leu His Tyr Ile
             115                 120                 125

Leu Asn Gly His Leu Leu Arg Pro Tyr His Val Lys Gln Phe Val Lys
         130                 135                 140

Ser Tyr Leu Lys Asn Met Asp Gly Cys Ile Ala Pro Ser Gly Arg Val
145                 150                 155                 160

Glu Asp Leu Leu Lys Arg Tyr Gly Val Gln Ile Pro Ile Arg Val Ile
                 165                 170                 175

Pro Thr Gly Val Asp Leu Gln Gly Met Asn Gly Asp Ala Glu Arg Asp
             180                 185                 190

Val Arg Gln Glu Leu Gly Ile Asp Lys Asp Ala Pro Val Ile Leu Thr
             195                 200                 205

Leu Ser Arg Ile Ala Ala Glu Lys Lys Ile Asn His Ile Leu Asn Val
         210                 215                 220

Met Pro Ala Ile Val Glu Phe Pro Asn Ile Lys Phe Val Ile Ala
225                 230                 235                 240

Gly Asp Gly Pro Asp Val Lys Val Leu Lys Glu Gln Val Glu Arg Leu
                 245                 250                 255

Thr Leu Glu Asp Tyr Val Leu Phe Val Gly Asn Val Asp His Gly Asp
             260                 265                 270

Val Gly Asn Tyr Tyr Arg Met Ala Asp Leu Phe Val Ser Ala Ser Asp
         275                 280                 285

Thr Glu Thr Gln Gly Leu Thr Tyr Ile Glu Ala Leu Ala Ala Gly Thr
     290                 295                 300

Pro Cys Val Val Tyr Asp Thr Asp Tyr Thr Glu Asn Ile Phe Asp Asn
305                 310                 315                 320

Asp Val Phe Gly Arg Thr Phe Val Thr Gln Lys Glu Met Leu Gln Glu
                 325                 330                 335

Ile Ile Glu Leu Leu Lys Lys Gly His Asn Arg Ile Pro Gln Asp Leu
             340                 345                 350

Leu Gln Asn Lys Leu Gln Lys Ile Ser Ser Gln Phe Ala Thr Asn
         355                 360                 365

Val His Asp Phe Tyr Lys Tyr Ala Ile Asp His Tyr Gln Pro Lys His
     370                 375                 380

Glu Glu Ile
385

<210> SEQ ID NO 5
<211> LENGTH: 1041
<212> TYPE: DNA
<213> ORGANISM: Lactobacillus acidophilus
<220> FEATURE:
<221> NAME/KEY: misc_feature
<222> LOCATION: (1)...(1041)
<223> OTHER INFORMATION: LBA0445  Glycosyltransferase GenBank Accession No. AAV42335
<220> FEATURE:
<221> NAME/KEY: CDS
<222> LOCATION: (1)...(1041)

<400> SEQUENCE: 5

```
atg att aga att aat atg ttc tca caa gct gat tca gtt aaa ggt caa      48
Met Ile Arg Ile Asn Met Phe Ser Gln Ala Asp Ser Val Lys Gly Gln
 1               5                  10                  15 gga gtg ggc tca gcc tac aat gaa ttg atc aaa tta ttg aga acc cgc      96
Gly Val Gly Ser Ala Tyr Asn Glu Leu Ile Lys Leu Leu Arg Thr Arg
             20                  25                  30 tta gta gat gag ttt tat gta aca att aat aga tat ggt aat agt gat     144
Leu Val Asp Glu Phe Tyr Val Thr Ile Asn Arg Tyr Gly Asn Ser Asp
         35                  40                  45 tta acg cac tat cat aca att aat cca act tat ttc gta aat agt ttt     192
Leu Thr His Tyr His Thr Ile Asn Pro Thr Tyr Phe Val Asn Ser Phe
     50                  55                  60 tca cct gct cgt gga aga aaa ata gga tat gtt cac ttt ttg cct gat     240
Ser Pro Ala Arg Gly Arg Lys Ile Gly Tyr Val His Phe Leu Pro Asp
 65                  70                  75                  80 aca tta gat gga tcg ctt aag ttg ccg gga ata gct aaa aat gtg gtt     288
Thr Leu Asp Gly Ser Leu Lys Leu Pro Gly Ile Ala Lys Asn Val Val
                 85                  90                  95 tat gat tac gtg att gat ttt tat aag cga atg gat caa atc gta gtt     336
Tyr Asp Tyr Val Ile Asp Phe Tyr Lys Arg Met Asp Gln Ile Val Val
            100                 105                 110 gta aat cca att ttt att gat aaa ttg gtt gat tat ggc att gaa cgc     384
Val Asn Pro Ile Phe Ile Asp Lys Leu Val Asp Tyr Gly Ile Glu Arg
        115                 120                 125 gat agg gtt aaa tac att cct aat ttt gtt tct aaa gaa gaa ttt tat     432
Asp Arg Val Lys Tyr Ile Pro Asn Phe Val Ser Lys Glu Glu Phe Tyr
    130                 135                 140 gaa gaa tca ttg gca agt aag aat gcc ttt cga cat gaa tta aag att     480
Glu Glu Ser Leu Ala Ser Lys Asn Ala Phe Arg His Glu Leu Lys Ile
145                 150                 155                 160 cca ctt gat aag ttt gtt gtt ttt ggt gat gga caa gtt caa gaa cgt     528
Pro Leu Asp Lys Phe Val Val Phe Gly Asp Gly Gln Val Gln Glu Arg
                165                 170                 175 aaa gga att gat gat ttt gta aaa atg gct aaa gct aat cca gat gtt     576
Lys Gly Ile Asp Asp Phe Val Lys Met Ala Lys Ala Asn Pro Asp Val
            180                 185                 190 cag ttt att tgg gct ggt gga ttt tcg ttt ggc aaa att aca gat gga     624
Gln Phe Ile Trp Ala Gly Gly Phe Ser Phe Gly Lys Ile Thr Asp Gly
        195                 200                 205 tat aat cac tat aaa gaa atg gtg gat aat cca cct gaa aat ttg att     672
Tyr Asn His Tyr Lys Glu Met Val Asp Asn Pro Pro Glu Asn Leu Ile
    210                 215                 220 ttt aca gga atc gta gat cgt aca aaa tta gtt aag tat ttg aat att     720
Phe Thr Gly Ile Val Asp Arg Thr Lys Leu Val Lys Tyr Leu Asn Ile
225                 230                 235                 240 gct gat tta ttt gtt tta cca tca tac gat gaa cta ttc cca atg tct     768
Ala Asp Leu Phe Val Leu Pro Ser Tyr Asp Glu Leu Phe Pro Met Ser
                245                 250                 255 gtt ctt gaa gcg ttt agt tgt ggg aca cca gtg ctt ttg cgc gat ctt     816
Val Leu Glu Ala Phe Ser Cys Gly Thr Pro Val Leu Leu Arg Asp Leu
            260                 265                 270 gac tta tat aag gca att att gat ggc tat tat atg agt gga aaa gac     864
Asp Leu Tyr Lys Ala Ile Ile Asp Gly Tyr Tyr Met Ser Gly Lys Asp
        275                 280                 285
```

```
ttt agt gaa atg aat caa att ttg caa aac gta att aaa aat cca caa      912
Phe Ser Glu Met Asn Gln Ile Leu Gln Asn Val Ile Lys Asn Pro Gln
    290                 295                 300 tta ttg aaa aaa tat agt gat tta tcg ttg aag gcc agc caa gaa tat      960
Leu Leu Lys Lys Tyr Ser Asp Leu Ser Leu Lys Ala Ser Gln Glu Tyr
305                 310                 315                 320 tca gaa gaa cga tta gct aaa att tgg aat gaa ttt tat cat gag caa     1008
Ser Glu Glu Arg Leu Ala Lys Ile Trp Asn Glu Phe Tyr His Glu Gln
                325                 330                 335 tat aaa ttg ggc aaa gaa cta gga caa att cat                         1041
Tyr Lys Leu Gly Lys Glu Leu Gly Gln Ile His
            340                 345
```

<210> SEQ ID NO 6
<211> LENGTH: 347
<212> TYPE: PRT
<213> ORGANISM: Lactobacillus acidophilus

<400> SEQUENCE: 6

```
Met Ile Arg Ile Asn Met Phe Ser Gln Ala Asp Ser Val Lys Gly Gln
1               5                   10                  15

Gly Val Gly Ser Ala Tyr Asn Glu Leu Ile Lys Leu Leu Arg Thr Arg
            20                  25                  30

Leu Val Asp Glu Phe Tyr Val Thr Ile Asn Arg Tyr Gly Asn Ser Asp
        35                  40                  45

Leu Thr His Tyr His Thr Ile Asn Pro Thr Tyr Phe Val Asn Ser Phe
    50                  55                  60

Ser Pro Ala Arg Gly Arg Lys Ile Gly Tyr Val His Phe Leu Pro Asp
65                  70                  75                  80

Thr Leu Asp Gly Ser Leu Lys Leu Pro Gly Ile Ala Lys Asn Val Val
                85                  90                  95

Tyr Asp Tyr Val Ile Asp Phe Tyr Lys Arg Met Asp Gln Ile Val Val
            100                 105                 110

Val Asn Pro Ile Phe Ile Asp Lys Leu Val Asp Tyr Gly Ile Glu Arg
        115                 120                 125

Asp Arg Val Lys Tyr Ile Pro Asn Phe Val Ser Lys Glu Glu Phe Tyr
    130                 135                 140

Glu Glu Ser Leu Ala Ser Lys Asn Ala Phe Arg His Glu Leu Lys Ile
145                 150                 155                 160

Pro Leu Asp Lys Phe Val Val Phe Gly Asp Gly Gln Val Gln Glu Arg
                165                 170                 175

Lys Gly Ile Asp Asp Phe Val Lys Met Ala Lys Ala Asn Pro Asp Val
            180                 185                 190

Gln Phe Ile Trp Ala Gly Gly Phe Ser Phe Gly Lys Ile Thr Asp Gly
        195                 200                 205

Tyr Asn His Tyr Lys Glu Met Val Asp Asn Pro Glu Asn Leu Ile
    210                 215                 220

Phe Thr Gly Ile Val Asp Arg Thr Lys Leu Val Lys Tyr Leu Asn Ile
225                 230                 235                 240

Ala Asp Leu Phe Val Leu Pro Ser Tyr Asp Glu Leu Phe Pro Met Ser
                245                 250                 255

Val Leu Glu Ala Phe Ser Cys Gly Thr Pro Val Leu Leu Arg Asp Leu
            260                 265                 270

Asp Leu Tyr Lys Ala Ile Ile Asp Gly Tyr Tyr Met Ser Gly Lys Asp
        275                 280                 285

Phe Ser Glu Met Asn Gln Ile Leu Gln Asn Val Ile Lys Asn Pro Gln
```

```
                    290                 295                 300
Leu Leu Lys Lys Tyr Ser Asp Leu Ser Leu Lys Ala Ser Gln Glu Tyr
305                 310                 315                 320

Ser Glu Glu Arg Leu Ala Lys Ile Trp Asn Glu Phe Tyr His Glu Gln
                325                 330                 335

Tyr Lys Leu Gly Lys Glu Leu Gly Gln Ile His
            340                 345

<210> SEQ ID NO 7
<211> LENGTH: 1023
<212> TYPE: DNA
<213> ORGANISM: Lactobacillus acidophilus
<220> FEATURE:
<221> NAME/KEY: misc_feature
<222> LOCATION: (1)...(1023)
<223> OTHER INFORMATION: LBA0446  Integral membrane protein
      GenBank Accession No. AAV42336
<220> FEATURE:
<221> NAME/KEY: CDS
<222> LOCATION: (1)...(1023)

<400> SEQUENCE: 7 atg aat aaa aaa cat atg tgg ggc atc ttg gtt gtt ttg gca atc agt      48
Met Asn Lys Lys His Met Trp Gly Ile Leu Val Val Leu Ala Ile Ser
  1               5                  10                  15 gtc ttt gta ctt tat aca gat cta aag tct aca cca tta tct gac att      96
Val Phe Val Leu Tyr Thr Asp Leu Lys Ser Thr Pro Leu Ser Asp Ile
             20                  25                  30 ttg aag gct gct cat ggc ttg aat gtt gga gca ttg ata atg gtg ttt     144
Leu Lys Ala Ala His Gly Leu Asn Val Gly Ala Leu Ile Met Val Phe
         35                  40                  45 tgc tta atg ctt ttg tct tat gta tgc gaa gca gga att ctt gcc gtt     192
Cys Leu Met Leu Leu Ser Tyr Val Cys Glu Ala Gly Ile Leu Ala Val
     50                  55                  60 tta gca cat cga aaa tca gag cct aag cga tcg gca tgg tct ttt tta     240
Leu Ala His Arg Lys Ser Glu Pro Lys Arg Ser Ala Trp Ser Phe Leu
 65                  70                  75                  80 cgt atc cct att att caa gca cta ttt aat gcg ata act cct atg tct     288
Arg Ile Pro Ile Ile Gln Ala Leu Phe Asn Ala Ile Thr Pro Met Ser
                 85                  90                  95 aca gga gga cag cct tcg caa ctt gca gct atg att caa atg gga atg     336
Thr Gly Gly Gln Pro Ser Gln Leu Ala Ala Met Ile Gln Met Gly Met
            100                 105                 110 gaa ggt ggt cga tcg act tct att ttg tta atg aaa ttt att att tat     384
Glu Gly Gly Arg Ser Thr Ser Ile Leu Leu Met Lys Phe Ile Ile Tyr
        115                 120                 125 caa ata gtt gtt tta ttt gcc tat gta ttt acc att tta ttt ggt ttc     432
Gln Ile Val Val Leu Phe Ala Tyr Val Phe Thr Ile Leu Phe Gly Phe
    130                 135                 140 cat atg gta atg acc aag ttt gca ggt ctc gct att ttt att gca att     480
His Met Val Met Thr Lys Phe Ala Gly Leu Ala Ile Phe Ile Ala Ile
145                 150                 155                 160 ggc ttt tta atc cat gtc agt tca att atc ttt ttg tta gca att atg     528
Gly Phe Leu Ile His Val Ser Ser Ile Ile Phe Leu Leu Ala Ile Met
                165                 170                 175 ttt gcc tat cgc ttt act aaa aga act act aat tgg att atg gat tta     576
Phe Ala Tyr Arg Phe Thr Lys Arg Thr Thr Asn Trp Ile Met Asp Leu
            180                 185                 190 ttg gct aaa ttt atg aaa aaa gaa cgc gtt gaa aaa tgg cgt acg gca     624
Leu Ala Lys Phe Met Lys Lys Glu Arg Val Glu Lys Trp Arg Thr Ala
        195                 200                 205
```

|   |   |
|---|---|
| act tta gaa aaa ata gat aca ttt tat gct gaa agc caa aag tta aaa<br>Thr Leu Glu Lys Ile Asp Thr Phe Tyr Ala Glu Ser Gln Lys Leu Lys<br>210                            215                         220 | 672 |
| aaa gag aag aag aag tta att atg gct tcg att tta acg att cta caa<br>Lys Glu Lys Lys Lys Leu Ile Met Ala Ser Ile Leu Thr Ile Leu Gln<br>225                          230                     235                  240 | 720 |
| tta ctc ttt ttc tac tca att cca ttt atg att ttg tca gct ctt aat<br>Leu Leu Phe Phe Tyr Ser Ile Pro Phe Met Ile Leu Ser Ala Leu Asn<br>                   245                     250                  255 | 768 |
| gtt cca tgt tca tgg ctt agt gtt acg cag atg aat att atg att att<br>Val Pro Cys Ser Trp Leu Ser Val Thr Gln Met Asn Ile Met Ile Ile<br>260                            265                        270 | 816 |
| atg ttt atg gca att att cca att cca ggc gca tcc ggt gga gca gaa<br>Met Phe Met Ala Ile Ile Pro Ile Pro Gly Ala Ser Gly Gly Ala Glu<br>         275                     280                     285 | 864 |
| tat agt ttt cag acg tta ttt tca aca ttt att tct acg cat ggt gcc<br>Tyr Ser Phe Gln Thr Leu Phe Ser Thr Phe Ile Ser Thr His Gly Ala<br>290                            295                     300 | 912 |
| tta att ttg gca atg ttt atc tgg cgt ttt tca act tat ttc ttt gga<br>Leu Ile Leu Ala Met Phe Ile Trp Arg Phe Ser Thr Tyr Phe Phe Gly<br>305                          310                     315                  320 | 960 |
| atg atc tta gga ata ttt ggt tgg att ttt aag cct aaa aag ata aaa<br>Met Ile Leu Gly Ile Phe Gly Trp Ile Phe Lys Pro Lys Lys Ile Lys<br>                   325                     330                  335 | 1008 |
| agc tca gaa agt aat<br>Ser Ser Glu Ser Asn<br>340 | 1023 |

<210> SEQ ID NO 8
<211> LENGTH: 341
<212> TYPE: PRT
<213> ORGANISM: Lactobacillus acidophilus

<400> SEQUENCE: 8

Met Asn Lys Lys His Met Trp Gly Ile Leu Val Val Leu Ala Ile Ser
1               5                   10                  15

Val Phe Val Leu Tyr Thr Asp Leu Lys Ser Thr Pro Leu Ser Asp Ile
            20                  25                  30

Leu Lys Ala Ala His Gly Leu Asn Val Gly Ala Leu Ile Met Val Phe
        35                  40                  45

Cys Leu Met Leu Ser Tyr Val Cys Glu Ala Gly Ile Leu Ala Val
    50                  55                  60

Leu Ala His Arg Lys Ser Glu Pro Lys Arg Ser Ala Trp Ser Phe Leu
65                  70                  75                  80

Arg Ile Pro Ile Ile Gln Ala Leu Phe Asn Ala Ile Thr Pro Met Ser
                85                  90                  95

Thr Gly Gly Gln Pro Ser Gln Leu Ala Ala Met Ile Gln Met Gly Met
            100                 105                 110

Glu Gly Gly Arg Ser Thr Ser Ile Leu Leu Met Lys Phe Ile Ile Tyr
        115                 120                 125

Gln Ile Val Val Leu Phe Ala Tyr Val Phe Thr Ile Leu Phe Gly Phe
    130                 135                 140

His Met Val Met Thr Lys Phe Ala Gly Leu Ala Ile Phe Ile Ala Ile
145                 150                 155                 160

Gly Phe Leu Ile His Val Ser Ser Ile Ile Phe Leu Leu Ala Ile Met
                165                 170                 175

Phe Ala Tyr Arg Phe Thr Lys Arg Thr Thr Asn Trp Ile Met Asp Leu
            180                 185                 190

-continued

```
Leu Ala Lys Phe Met Lys Lys Glu Arg Val Glu Lys Trp Arg Thr Ala
        195                 200                 205

Thr Leu Glu Lys Ile Asp Thr Phe Tyr Ala Glu Ser Gln Lys Leu Lys
    210                 215                 220

Lys Glu Lys Lys Lys Leu Ile Met Ala Ser Ile Leu Thr Ile Leu Gln
225                 230                 235                 240

Leu Leu Phe Phe Tyr Ser Ile Pro Phe Met Ile Leu Ser Ala Leu Asn
                245                 250                 255

Val Pro Cys Ser Trp Leu Ser Val Thr Gln Met Asn Ile Met Ile Ile
            260                 265                 270

Met Phe Met Ala Ile Ile Pro Ile Pro Gly Ala Ser Gly Gly Ala Glu
        275                 280                 285

Tyr Ser Phe Gln Thr Leu Phe Ser Thr Phe Ile Ser Thr His Gly Ala
    290                 295                 300

Leu Ile Leu Ala Met Phe Ile Trp Arg Phe Ser Thr Tyr Phe Phe Gly
305                 310                 315                 320

Met Ile Leu Gly Ile Phe Gly Trp Ile Phe Lys Pro Lys Lys Ile Lys
                325                 330                 335

Ser Ser Glu Ser Asn
            340

<210> SEQ ID NO 9
<211> LENGTH: 1512
<212> TYPE: DNA
<213> ORGANISM: Lactobacillus acidophilus
<220> FEATURE:
<221> NAME/KEY: misc_feature
<222> LOCATION: (1)...(1512)
<223> OTHER INFORMATION: LBA1926  D-alanine--D-alanyl carrier protein
      ligase, DltA
      GenBank Accession No. AAV43723
<220> FEATURE:
<221> NAME/KEY: CDS
<222> LOCATION: (1)...(1512)

<400> SEQUENCE: 9 atg att caa gat gtt att aag aga att gac gag ata gct gaa aat gaa      48
Met Ile Gln Asp Val Ile Lys Arg Ile Asp Glu Ile Ala Glu Asn Glu
1               5                   10                  15 cca gat cgt gta gtt tac gat tat ctc ggt gaa acc aat aca tat ggt      96
Pro Asp Arg Val Val Tyr Asp Tyr Leu Gly Glu Thr Asn Thr Tyr Gly
            20                  25                  30 gac ctt aag aag cgt tca aac gct tgg gca cac aag att gct agt atg     144
Asp Leu Lys Lys Arg Ser Asn Ala Trp Ala His Lys Ile Ala Ser Met
        35                  40                  45 gat atc cca gaa cat gca cca atc atg atc tgg ggt ggt caa aca ttt     192
Asp Ile Pro Glu His Ala Pro Ile Met Ile Trp Gly Gly Gln Thr Phe
    50                  55                  60 gaa atg att gct agt ttc tta ggt tgt gtt aaa tca ggc cac gca tat     240
Glu Met Ile Ala Ser Phe Leu Gly Cys Val Lys Ser Gly His Ala Tyr
65                  70                  75                  80 att cca att gca agt tat tca aat gct gaa cgt tta aca atg att caa     288
Ile Pro Ile Ala Ser Tyr Ser Asn Ala Glu Arg Leu Thr Met Ile Gln
                85                  90                  95 gat gtt tca aaa tca cct atg gtt ttg gaa att gat cca ttg cca gac     336
Asp Val Ser Lys Ser Pro Met Val Leu Glu Ile Asp Pro Leu Pro Asp
            100                 105                 110 gtt aat tta gac ggc atc aag gta ctt aaa gct aat gaa gtt gaa gat     384
Val Asn Leu Asp Gly Ile Lys Val Leu Lys Ala Asn Glu Val Glu Asp
        115                 120                 125
```

| | | |
|---|---|---|
| ggc gac ttt aca gtt gat gaa agt aat ttc gtt gaa ggc gac gaa aat<br>Gly Asp Phe Thr Val Asp Glu Ser Asn Phe Val Glu Gly Asp Glu Asn<br>130                        135                        140 | | 432 |
| tac tat att atc ttt act tca ggt act act ggt aag cca aag ggt gta<br>Tyr Tyr Ile Ile Phe Thr Ser Gly Thr Thr Gly Lys Pro Lys Gly Val<br>145                        150                        155                        160 | | 480 |
| caa atc agt cat gat aat ttg ttg agt ttt gta aac tgg gaa tta tca<br>Gln Ile Ser His Asp Asn Leu Leu Ser Phe Val Asn Trp Glu Leu Ser<br>                        165                        170                        175 | | 528 |
| gat ttt aat ttg cca gaa cac cca agc ttt ttg gca caa gct cca tac<br>Asp Phe Asn Leu Pro Glu His Pro Ser Phe Leu Ala Gln Ala Pro Tyr<br>                        180                        185                        190 | | 576 |
| tca ttt gac ttg tca gtt atg agc ctt tat cct gca ctt gtt tca gca<br>Ser Phe Asp Leu Ser Val Met Ser Leu Tyr Pro Ala Leu Val Ser Ala<br>195                        200                        205 | | 624 |
| gga aag ctt gtt gtt tta cca cat gat gtt acg caa aac ttt ggt caa<br>Gly Lys Leu Val Val Leu Pro His Asp Val Thr Gln Asn Phe Gly Gln<br>          210                        215                        220 | | 672 |
| ttg ttc caa act tta cca aaa atg caa ttt aat gtt tgg gta tca act<br>Leu Phe Gln Thr Leu Pro Lys Met Gln Phe Asn Val Trp Val Ser Thr<br>225                        230                        235                        240 | | 720 |
| cca tca ttt gca caa atg tgt ttc tta gat aaa acc ttt gat gca gaa<br>Pro Ser Phe Ala Gln Met Cys Phe Leu Asp Lys Thr Phe Asp Ala Glu<br>                            245                        250                        255 | | 768 |
| cat cat cca gac tta act cac ttc tta ttc tgt ggt gaa gaa tta cca<br>His His Pro Asp Leu Thr His Phe Leu Phe Cys Gly Glu Glu Leu Pro<br>                    260                        265                        270 | | 816 |
| cat agt gaa gct gat atg ctt aag aag aag ttc cca gaa agt cat att<br>His Ser Glu Ala Asp Met Leu Lys Lys Lys Phe Pro Glu Ser His Ile<br>        275                        280                        285 | | 864 |
| ttt aat act tac ggt cct act gaa act aca gtt gct gtg act caa gta<br>Phe Asn Thr Tyr Gly Pro Thr Glu Thr Thr Val Ala Val Thr Gln Val<br>          290                        295                        300 | | 912 |
| gag atc act gat gaa ata ctt gaa aag tat gat cgt cta cca att ggt<br>Glu Ile Thr Asp Glu Ile Leu Glu Lys Tyr Asp Arg Leu Pro Ile Gly<br>305                        310                        315                        320 | | 960 |
| aga gta aaa gaa gac act aag att act att gat act tca aag gga gat<br>Arg Val Lys Glu Asp Thr Lys Ile Thr Ile Asp Thr Ser Lys Gly Asp<br>                        325                        330                        335 | | 1008 |
| aag cct ggc gaa ggt gaa atc att atc agt ggt cct agc gtt tca aaa<br>Lys Pro Gly Glu Gly Glu Ile Ile Ile Ser Gly Pro Ser Val Ser Lys<br>          340                        345                        350 | | 1056 |
| ggg tac atg aat aac cct gaa aag acc gaa gct gct ttc ttc caa aat<br>Gly Tyr Met Asn Asn Pro Glu Lys Thr Glu Ala Ala Phe Phe Gln Asn<br>                    355                        360                        365 | | 1104 |
| gag ggc gac aag tat cgc agc tac cgt agt gga gat gct gga ttc ttt<br>Glu Gly Asp Lys Tyr Arg Ser Tyr Arg Ser Gly Asp Ala Gly Phe Phe<br>        370                        375                        380 | | 1152 |
| gat ggt gat atg cta ttt tat cgc ggt aga atc gac ttc caa atc aag<br>Asp Gly Asp Met Leu Phe Tyr Arg Gly Arg Ile Asp Phe Gln Ile Lys<br>385                        390                        395                        400 | | 1200 |
| ttc aat ggt tac aga atc gaa ctt gaa gaa att aat ttc tac ttg tca<br>Phe Asn Gly Tyr Arg Ile Glu Leu Glu Glu Ile Asn Phe Tyr Leu Ser<br>                        405                        410                        415 | | 1248 |
| aag aat gaa ttt gta cgt tat ggt gtc gca gca cct aaa tac aat aaa<br>Lys Asn Glu Phe Val Arg Tyr Gly Val Ala Ala Pro Lys Tyr Asn Lys<br>                    420                        425                        430 | | 1296 |
| gat cat act gta aag caa att gtt gct gaa atc gaa ttg aag cat ggc<br>Asp His Thr Val Lys Gln Ile Val Ala Glu Ile Glu Leu Lys His Gly | | 1344 |

```
                           435                   440                   445
gtt cgt cgt aag tat tct gat gca caa ctt act aag ttg att cgt gaa      1392
Val Arg Arg Lys Tyr Ser Asp Ala Gln Leu Thr Lys Leu Ile Arg Glu
        450                 455                 460 gac tta gct aag aac gtg atg cct tac atg att cca cag cgt tat gtt      1440
Asp Leu Ala Lys Asn Val Met Pro Tyr Met Ile Pro Gln Arg Tyr Val
465                 470                 475                 480 tac caa gat aca tta cca att tct caa aac ggt aag gtg gat att aag      1488
Tyr Gln Asp Thr Leu Pro Ile Ser Gln Asn Gly Lys Val Asp Ile Lys
                485                 490                 495 gca gtt att aag gag gtt aat aag                                      1512
Ala Val Ile Lys Glu Val Asn Lys
            500
```

<210> SEQ ID NO 10
<211> LENGTH: 504
<212> TYPE: PRT
<213> ORGANISM: Lactobacillus acidophilus

<400> SEQUENCE: 10

```
Met Ile Gln Asp Val Ile Lys Arg Ile Asp Glu Ile Ala Glu Asn Glu
1               5                   10                  15

Pro Asp Arg Val Val Tyr Asp Tyr Leu Gly Glu Thr Asn Thr Tyr Gly
                20                  25                  30

Asp Leu Lys Lys Arg Ser Asn Ala Trp Ala His Lys Ile Ala Ser Met
            35                  40                  45

Asp Ile Pro Glu His Ala Pro Ile Met Ile Trp Gly Gly Gln Thr Phe
        50                  55                  60

Glu Met Ile Ala Ser Phe Leu Gly Cys Val Lys Ser Gly His Ala Tyr
65                  70                  75                  80

Ile Pro Ile Ala Ser Tyr Ser Asn Ala Glu Arg Leu Thr Met Ile Gln
                85                  90                  95

Asp Val Ser Lys Ser Pro Met Val Leu Glu Ile Asp Pro Leu Pro Asp
            100                 105                 110

Val Asn Leu Asp Gly Ile Lys Val Leu Lys Ala Asn Glu Val Glu Asp
        115                 120                 125

Gly Asp Phe Thr Val Asp Glu Ser Asn Phe Val Glu Gly Asp Glu Asn
    130                 135                 140

Tyr Tyr Ile Ile Phe Thr Ser Gly Thr Thr Gly Lys Pro Lys Gly Val
145                 150                 155                 160

Gln Ile Ser His Asp Asn Leu Leu Ser Phe Val Asn Trp Glu Leu Ser
                165                 170                 175

Asp Phe Asn Leu Pro Glu His Pro Ser Phe Leu Ala Gln Ala Pro Tyr
            180                 185                 190

Ser Phe Asp Leu Ser Val Met Ser Leu Tyr Pro Ala Leu Val Ser Ala
        195                 200                 205

Gly Lys Leu Val Val Leu Pro His Asp Val Thr Gln Asn Phe Gly Gln
    210                 215                 220

Leu Phe Gln Thr Leu Pro Lys Met Gln Phe Asn Val Trp Val Ser Thr
225                 230                 235                 240

Pro Ser Phe Ala Gln Met Cys Phe Leu Asp Lys Thr Phe Asp Ala Glu
                245                 250                 255

His His Pro Asp Leu Thr His Phe Leu Phe Cys Gly Glu Glu Leu Pro
            260                 265                 270

His Ser Glu Ala Asp Met Leu Lys Lys Lys Phe Pro Glu Ser His Ile
        275                 280                 285
```

```
Phe Asn Thr Tyr Gly Pro Thr Glu Thr Thr Val Ala Val Thr Gln Val
            290                 295                 300

Glu Ile Thr Asp Glu Ile Leu Glu Lys Tyr Asp Arg Leu Pro Ile Gly
305                 310                 315                 320

Arg Val Lys Glu Asp Thr Lys Ile Thr Ile Asp Thr Ser Lys Gly Asp
                325                 330                 335

Lys Pro Gly Glu Gly Glu Ile Ile Ile Ser Gly Pro Ser Val Ser Lys
                340                 345                 350

Gly Tyr Met Asn Asn Pro Glu Lys Thr Glu Ala Ala Phe Phe Gln Asn
                355                 360                 365

Glu Gly Asp Lys Tyr Arg Ser Tyr Arg Ser Gly Asp Ala Gly Phe Phe
370                 375                 380

Asp Gly Asp Met Leu Phe Tyr Arg Gly Arg Ile Asp Phe Gln Ile Lys
385                 390                 395                 400

Phe Asn Gly Tyr Arg Ile Glu Leu Glu Glu Ile Asn Phe Tyr Leu Ser
                405                 410                 415

Lys Asn Glu Phe Val Arg Tyr Gly Val Ala Ala Pro Lys Tyr Asn Lys
                420                 425                 430

Asp His Thr Val Lys Gln Ile Val Ala Glu Ile Glu Leu Lys His Gly
                435                 440                 445

Val Arg Arg Lys Tyr Ser Asp Ala Gln Leu Thr Lys Leu Ile Arg Glu
450                 455                 460

Asp Leu Ala Lys Asn Val Met Pro Tyr Met Ile Pro Gln Arg Tyr Val
465                 470                 475                 480

Tyr Gln Asp Thr Leu Pro Ile Ser Gln Asn Gly Lys Val Asp Ile Lys
                485                 490                 495

Ala Val Ile Lys Glu Val Asn Lys
                500

<210> SEQ ID NO 11
<211> LENGTH: 1236
<212> TYPE: DNA
<213> ORGANISM: Lactobacillus acidophilus
<220> FEATURE:
<221> NAME/KEY: misc_feature
<222> LOCATION: (1)...(1236)
<223> OTHER INFORMATION: LBA1925   D-alanyl transfer protein DltB
      GenBank Accession No. AAV43722
<220> FEATURE:
<221> NAME/KEY: CDS
<222> LOCATION: (1)...(1236)

<400> SEQUENCE: 11 gtg aat ttt aat ttc att aac tta caa cct tac tca aat ccg caa tat      48
Val Asn Phe Asn Phe Ile Asn Leu Gln Pro Tyr Ser Asn Pro Gln Tyr
1               5                   10                  15 ttt gtt tac ttg atg atc gcg tta att cct att att att gga ctt tac      96
Phe Val Tyr Leu Met Ile Ala Leu Ile Pro Ile Ile Ile Gly Leu Tyr
            20                  25                  30 tat ggt cat cgt ctc aag aca tat gaa gcg att ttc tca att gtt ttc     144
Tyr Gly His Arg Leu Lys Thr Tyr Glu Ala Ile Phe Ser Ile Val Phe
        35                  40                  45 tta ttc ttg att ttt gac ggt agt cac tgg caa caa ggt gta aac ttg     192
Leu Phe Leu Ile Phe Asp Gly Ser His Trp Gln Gln Gly Val Asn Leu
    50                  55                  60 cta atc tgg ctg gtt tat gaa ttt gct ttg acg ttt gct tat cag tat     240
Leu Ile Trp Leu Val Tyr Glu Phe Ala Leu Thr Phe Ala Tyr Gln Tyr
65                  70                  75                  80
```

```
tat cgt cat cat ggt aaa aat aag act tgg gta ttt agc ttg gct gta    288
Tyr Arg His His Gly Lys Asn Lys Thr Trp Val Phe Ser Leu Ala Val
            85                  90                  95 att tta gcg att att ccg ctg gct gca gtt aag tat ttg acc gca ttc    336
Ile Leu Ala Ile Ile Pro Leu Ala Ala Val Lys Tyr Leu Thr Ala Phe
            100                 105                 110 cca ctt aat tca atc aac ttt gtt att gga ttt tta ggt att tct tac    384
Pro Leu Asn Ser Ile Asn Phe Val Ile Gly Phe Leu Gly Ile Ser Tyr
            115                 120                 125 gta act ttc aaa aca gtg caa gtt att atg gaa atg cgt gac ggt gcg    432
Val Thr Phe Lys Thr Val Gln Val Ile Met Glu Met Arg Asp Gly Ala
            130                 135                 140 att aag aag gtg gat cct gta acc tat gca aga ttc tta ctc ttc ttc    480
Ile Lys Lys Val Asp Pro Val Thr Tyr Ala Arg Phe Leu Leu Phe Phe
145                 150                 155                 160 cca act att tca tca ggt cct att gat cga tat cgt aga ttt aag aaa    528
Pro Thr Ile Ser Ser Gly Pro Ile Asp Arg Tyr Arg Arg Phe Lys Lys
            165                 170                 175 gat tac gat aaa gtt cct aca aga gac gca tat att aca gat tta caa    576
Asp Tyr Asp Lys Val Pro Thr Arg Asp Ala Tyr Ile Thr Asp Leu Gln
            180                 185                 190 tat gct gta aga tat ttg ttc caa gga ttt tta tac aaa ttt att att    624
Tyr Ala Val Arg Tyr Leu Phe Gln Gly Phe Leu Tyr Lys Phe Ile Ile
            195                 200                 205 ggt tgg ttc ttt ggt act tat tgg ctt cct aag att agt gcc gct gct    672
Gly Trp Phe Phe Gly Thr Tyr Trp Leu Pro Lys Ile Ser Ala Ala Ala
210                 215                 220 tta gcg gtg gga aat gct aat ggt ggt ttg aag tta tca tgg tgg ctt    720
Leu Ala Val Gly Asn Ala Asn Gly Gly Leu Lys Leu Ser Trp Trp Leu
225                 230                 235                 240 ctt gct tac atg tat tgc tac agt atg tac ctg ttc ttt gac ttt gca    768
Leu Ala Tyr Met Tyr Cys Tyr Ser Met Tyr Leu Phe Phe Asp Phe Ala
            245                 250                 255 ggt tac tca cta ttt gct gta tca att tca tac ttc atg ggt att cat    816
Gly Tyr Ser Leu Phe Ala Val Ser Ile Ser Tyr Phe Met Gly Ile His
            260                 265                 270 acc cca atg aac ttc aac aaa cca ttt att tct aag aat att aaa gac    864
Thr Pro Met Asn Phe Asn Lys Pro Phe Ile Ser Lys Asn Ile Lys Asp
            275                 280                 285 ttc tgg aac cgt tgg cac att aca ctt tca ttc tgg ttc cgt gat tat    912
Phe Trp Asn Arg Trp His Ile Thr Leu Ser Phe Trp Phe Arg Asp Tyr
            290                 295                 300 atc tac atg cga ttc act ttc ttt gca atg aaa aaa aag ttg ttt aag    960
Ile Tyr Met Arg Phe Thr Phe Phe Ala Met Lys Lys Lys Leu Phe Lys
305                 310                 315                 320 aat cgt att aga ttg tca cag gta tca tat ttc cta tta ttc ttg ata    1008
Asn Arg Ile Arg Leu Ser Gln Val Ser Tyr Phe Leu Leu Phe Leu Ile
            325                 330                 335 atg gga ttc tgg cat ggg tta aca tgg tat tat att gtt tat ggt ata    1056
Met Gly Phe Trp His Gly Leu Thr Trp Tyr Tyr Ile Val Tyr Gly Ile
            340                 345                 350 ttc cat gcc act gct atc tgt gtc aac gat atg tgg cta aga ttt aag    1104
Phe His Ala Thr Ala Ile Cys Val Asn Asp Met Trp Leu Arg Phe Lys
            355                 360                 365 aga aag cat aag aaa caa att cca cat aac aag ttt act gaa tgg ttt    1152
Arg Lys His Lys Lys Gln Ile Pro His Asn Lys Phe Thr Glu Trp Phe
            370                 375                 380 gcc att ttc tta act ttc aat atg gta tgt ttc agt ttc ttg att ttc    1200
Ala Ile Phe Leu Thr Phe Asn Met Val Cys Phe Ser Phe Leu Ile Phe
385                 390                 395                 400
```

```
tca gga ttc ctt agt caa ttg tgg ttt ggc tgg aag                          1236
Ser Gly Phe Leu Ser Gln Leu Trp Phe Gly Trp Lys
            405                 410
```

<210> SEQ ID NO 12
<211> LENGTH: 412
<212> TYPE: PRT
<213> ORGANISM: Lactobacillus acidophilus

<400> SEQUENCE: 12

```
Val Asn Phe Asn Phe Ile Asn Leu Gln Pro Tyr Ser Asn Pro Gln Tyr
 1               5                  10                  15

Phe Val Tyr Leu Met Ile Ala Leu Ile Pro Ile Ile Gly Leu Tyr
            20                  25                  30

Tyr Gly His Arg Leu Lys Thr Tyr Glu Ala Ile Phe Ser Ile Val Phe
            35                  40                  45

Leu Phe Leu Ile Phe Asp Gly Ser His Trp Gln Gln Gly Val Asn Leu
 50                  55                  60

Leu Ile Trp Leu Val Tyr Glu Phe Ala Leu Thr Phe Ala Tyr Gln Tyr
 65                  70                  75                  80

Tyr Arg His His Gly Lys Asn Lys Thr Trp Val Phe Ser Leu Ala Val
                85                  90                  95

Ile Leu Ala Ile Ile Pro Leu Ala Ala Val Lys Tyr Leu Thr Ala Phe
            100                 105                 110

Pro Leu Asn Ser Ile Asn Phe Val Gly Phe Leu Gly Ile Ser Tyr
            115                 120                 125

Val Thr Phe Lys Thr Val Gln Val Ile Met Glu Met Arg Asp Gly Ala
130                 135                 140

Ile Lys Lys Val Asp Pro Val Thr Tyr Ala Arg Phe Leu Leu Phe Phe
145                 150                 155                 160

Pro Thr Ile Ser Ser Gly Pro Ile Asp Arg Tyr Arg Arg Phe Lys Lys
            165                 170                 175

Asp Tyr Asp Lys Val Pro Thr Arg Asp Ala Tyr Ile Thr Asp Leu Gln
            180                 185                 190

Tyr Ala Val Arg Tyr Leu Phe Gln Gly Phe Leu Tyr Lys Phe Ile Ile
            195                 200                 205

Gly Trp Phe Phe Gly Thr Tyr Trp Leu Pro Lys Ile Ser Ala Ala Ala
        210                 215                 220

Leu Ala Val Gly Asn Ala Asn Gly Gly Leu Lys Leu Ser Trp Trp Leu
225                 230                 235                 240

Leu Ala Tyr Met Tyr Cys Tyr Ser Met Tyr Leu Phe Phe Asp Phe Ala
            245                 250                 255

Gly Tyr Ser Leu Phe Ala Val Ser Ile Ser Tyr Phe Met Gly Ile His
            260                 265                 270

Thr Pro Met Asn Phe Asn Lys Pro Phe Ile Ser Lys Asn Ile Lys Asp
        275                 280                 285

Phe Trp Asn Arg Trp His Ile Thr Leu Ser Phe Trp Phe Arg Asp Tyr
        290                 295                 300

Ile Tyr Met Arg Phe Thr Phe Phe Ala Met Lys Lys Lys Leu Phe Lys
305                 310                 315                 320

Asn Arg Ile Arg Leu Ser Gln Val Ser Tyr Phe Leu Leu Phe Leu Ile
            325                 330                 335

Met Gly Phe Trp His Gly Leu Thr Trp Tyr Tyr Ile Val Tyr Gly Ile
            340                 345                 350
```

```
Phe His Ala Thr Ala Ile Cys Val Asn Asp Met Trp Leu Arg Phe Lys
            355                 360                 365

Arg Lys His Lys Lys Gln Ile Pro His Asn Lys Phe Thr Glu Trp Phe
370                 375                 380

Ala Ile Phe Leu Thr Phe Asn Met Val Cys Phe Ser Phe Leu Ile Phe
385                 390                 395                 400

Ser Gly Phe Leu Ser Gln Leu Trp Phe Gly Trp Lys
            405                 410

<210> SEQ ID NO 13
<211> LENGTH: 237
<212> TYPE: DNA
<213> ORGANISM: Lactobacillus acidophilus
<220> FEATURE:
<221> NAME/KEY: misc_feature
<222> LOCATION: (1)...(237)
<223> OTHER INFORMATION: LBA1924  D-alanine--poly(phosphoribitol) ligase
      subunit 2, DltC
      GenBank Accession No. AAV43721
<220> FEATURE:
<221> NAME/KEY: CDS
<222> LOCATION: (1)...(237)

<400> SEQUENCE: 13 atg gac act aaa caa ggc gta tta gac att tta aac gat tta act ggt        48
Met Asp Thr Lys Gln Gly Val Leu Asp Ile Leu Asn Asp Leu Thr Gly
 1               5                  10                  15 gaa gat tta tca gat caa atg gat gaa aac atc ttt gat aat ggt ttg        96
Glu Asp Leu Ser Asp Gln Met Asp Glu Asn Ile Phe Asp Asn Gly Leu
            20                  25                  30 atg gac tca atg gca agt gta caa atg ctt ttg agt tta caa gaa aaa       144
Met Asp Ser Met Ala Ser Val Gln Met Leu Leu Ser Leu Gln Glu Lys
        35                  40                  45 ttt gat att gat gtt cct gta tca gaa ttt aat cgt gaa gaa tgg gac       192
Phe Asp Ile Asp Val Pro Val Ser Glu Phe Asn Arg Glu Glu Trp Asp
    50                  55                  60 act cct aac aag att gtt gca aag gtg gaa agc tta gaa aat gag           237
Thr Pro Asn Lys Ile Val Ala Lys Val Glu Ser Leu Glu Asn Glu
65                  70                  75

<210> SEQ ID NO 14
<211> LENGTH: 79
<212> TYPE: PRT
<213> ORGANISM: Lactobacillus acidophilus

<400> SEQUENCE: 14

Met Asp Thr Lys Gln Gly Val Leu Asp Ile Leu Asn Asp Leu Thr Gly
 1               5                  10                  15

Glu Asp Leu Ser Asp Gln Met Asp Glu Asn Ile Phe Asp Asn Gly Leu
            20                  25                  30

Met Asp Ser Met Ala Ser Val Gln Met Leu Leu Ser Leu Gln Glu Lys
        35                  40                  45

Phe Asp Ile Asp Val Pro Val Ser Glu Phe Asn Arg Glu Glu Trp Asp
    50                  55                  60

Thr Pro Asn Lys Ile Val Ala Lys Val Glu Ser Leu Glu Asn Glu
65                  70                  75

<210> SEQ ID NO 15
<211> LENGTH: 1284
<212> TYPE: DNA
<213> ORGANISM: Lactobacillus acidophilus
<220> FEATURE:
<221> NAME/KEY: misc_feature
```

```
<222> LOCATION: (1)...(1284)
<223> OTHER INFORMATION: LBA1923  D-alanyl transfer protein DltD
      GenBank Accession No. AAV43720
<220> FEATURE:
<221> NAME/KEY: CDS
<222> LOCATION: (1)...(1284)

<400> SEQUENCE: 15 atg agt aat aaa cgc cgg ctg tgg caa att ttt ggc cca gtt ctt tgc      48
Met Ser Asn Lys Arg Arg Leu Trp Gln Ile Phe Gly Pro Val Leu Cys
1               5                   10                  15 gct ttt atc ctt tta tta gtt gta ttt ctt att ccc tgg gaa aga act      96
Ala Phe Ile Leu Leu Leu Val Val Phe Leu Ile Pro Trp Glu Arg Thr
            20                  25                  30 ttt tct aag caa act atc tat gaa gca gct gcc tca caa aat agt act     144
Phe Ser Lys Gln Thr Ile Tyr Glu Ala Ala Ala Ser Gln Asn Ser Thr
        35                  40                  45 gta ttt aag ggc agt aca atg aag caa gaa gct tat aaa gat ggt tat     192
Val Phe Lys Gly Ser Thr Met Lys Gln Glu Ala Tyr Lys Asp Gly Tyr
    50                  55                  60 gta cca ttc tat ggt tca agt gaa ttg tct aga ttt gat cca ctt cac     240
Val Pro Phe Tyr Gly Ser Ser Glu Leu Ser Arg Phe Asp Pro Leu His
65                  70                  75                  80 cct agt gtt att gct gaa aag tat cac aga aat tac cgt cca ttt ctt     288
Pro Ser Val Ile Ala Glu Lys Tyr His Arg Asn Tyr Arg Pro Phe Leu
                85                  90                  95 cta ggt gga cca ggt agt caa tct ttg gct caa ttc ttg ggg atg cag     336
Leu Gly Gly Pro Gly Ser Gln Ser Leu Ala Gln Phe Leu Gly Met Gln
            100                 105                 110 ggt aca act aaa cag ctt aaa aac aaa aag gct gta gtg att att tca     384
Gly Thr Thr Lys Gln Leu Lys Asn Lys Lys Ala Val Val Ile Ile Ser
        115                 120                 125 cca caa tgg ttt acc aag aaa ggc caa gat cct aat gca ttt gct tta     432
Pro Gln Trp Phe Thr Lys Lys Gly Gln Asp Pro Asn Ala Phe Ala Leu
    130                 135                 140 tat tat tca cca ctt caa gca tgt aac ttc ttg tta agt gct aag aat     480
Tyr Tyr Ser Pro Leu Gln Ala Cys Asn Phe Leu Leu Ser Ala Lys Asn
145                 150                 155                 160 aat aag act gat cgt tat gct gct aag cgt ctg ctt gat atg cca gat     528
Asn Lys Thr Asp Arg Tyr Ala Ala Lys Arg Leu Leu Asp Met Pro Asp
                165                 170                 175 gta aag ggt gaa att aga aac agt ctt aag caa att gct gca ggt aaa     576
Val Lys Gly Glu Ile Arg Asn Ser Leu Lys Gln Ile Ala Ala Gly Lys
            180                 185                 190 aag cta act act ttt gaa aga ttt tat tta gaa aat cgt cgt aga atg     624
Lys Leu Thr Thr Phe Glu Arg Phe Tyr Leu Glu Asn Arg Arg Arg Met
        195                 200                 205 tta cgt aac gaa gat aac ttc ttt agt tca ttc caa tta cgc gat cgt     672
Leu Arg Asn Glu Asp Asn Phe Phe Ser Ser Phe Gln Leu Arg Asp Arg
    210                 215                 220 gta aat aag att caa aat aga gct aaa gta tta cct aat act tat tct     720
Val Asn Lys Ile Gln Asn Arg Ala Lys Val Leu Pro Asn Thr Tyr Ser
225                 230                 235                 240 gta gct gct ttg aac aag gtg gct gaa gaa cag gct gca gca cat act     768
Val Ala Ala Leu Asn Lys Val Ala Glu Glu Gln Ala Ala Ala His Thr
                245                 250                 255 act tca aat aac ttg gga att gac aat act ttc tat aga act cgt ttg     816
Thr Ser Asn Asn Leu Gly Ile Asp Asn Thr Phe Tyr Arg Thr Arg Leu
            260                 265                 270 cct aga aag gta tta aag aga ctc aag ggt agt caa cgt cac ttt gat     864
Pro Arg Lys Val Leu Lys Arg Leu Lys Gly Ser Gln Arg His Phe Asp
        275                 280                 285
```

```
tac gtt aga tct gtt gaa tat ggc gac ttc cag tta atg ctg gaa caa      912
Tyr Val Arg Ser Val Glu Tyr Gly Asp Phe Gln Leu Met Leu Glu Gln
    290                 295                 300 ttt gcc aag caa cat act aat gtg ttg ttc att att cca cca att aat      960
Phe Ala Lys Gln His Thr Asn Val Leu Phe Ile Ile Pro Pro Ile Asn
305                 310                 315                 320 ggt aag tgg atg aag tat act ggt tta tca caa aaa atg tat caa gaa     1008
Gly Lys Trp Met Lys Tyr Thr Gly Leu Ser Gln Lys Met Tyr Gln Glu
                325                 330                 335 tca gtt gct aaa att gaa caa caa ttg act agt caa ggt ttt gaa aat     1056
Ser Val Ala Lys Ile Glu Gln Gln Leu Thr Ser Gln Gly Phe Glu Asn
            340                 345                 350 att gca gat ctt tct aaa cgt ggt aat gaa aag tac ttc atg caa gat     1104
Ile Ala Asp Leu Ser Lys Arg Gly Asn Glu Lys Tyr Phe Met Gln Asp
        355                 360                 365 act att cac ctt ggt tgg aaa ggc tgg gta gct gtt gat caa gct gtt     1152
Thr Ile His Leu Gly Trp Lys Gly Trp Val Ala Val Asp Gln Ala Val
    370                 375                 380 aga cca ttt atg aag ttg cct aac gaa cgt tac aac tat gat atg tct     1200
Arg Pro Phe Met Lys Leu Pro Asn Glu Arg Tyr Asn Tyr Asp Met Ser
385                 390                 395                 400 aac tac tac ttc tca aag aag tgg cag aat aaa gat aac gtt aaa cgt     1248
Asn Tyr Tyr Phe Ser Lys Lys Trp Gln Asn Lys Asp Asn Val Lys Arg
                405                 410                 415 gta aat tta aat aat aaa gat cgt tta aaa gtg aag                     1284
Val Asn Leu Asn Asn Lys Asp Arg Leu Lys Val Lys
            420                 425

<210> SEQ ID NO 16
<211> LENGTH: 428
<212> TYPE: PRT
<213> ORGANISM: Lactobacillus acidophilus

<400> SEQUENCE: 16

Met Ser Asn Lys Arg Arg Leu Trp Gln Ile Phe Gly Pro Val Leu Cys
1               5                   10                  15

Ala Phe Ile Leu Leu Leu Val Val Phe Leu Ile Pro Trp Glu Arg Thr
            20                  25                  30

Phe Ser Lys Gln Thr Ile Tyr Glu Ala Ala Ser Gln Asn Ser Thr
        35                  40                  45

Val Phe Lys Gly Ser Thr Met Lys Gln Glu Ala Tyr Lys Asp Gly Tyr
50                  55                  60

Val Pro Phe Tyr Gly Ser Ser Glu Leu Ser Arg Phe Asp Pro Leu His
65                  70                  75                  80

Pro Ser Val Ile Ala Glu Lys Tyr His Arg Asn Tyr Arg Pro Phe Leu
                85                  90                  95

Leu Gly Gly Pro Gly Ser Gln Ser Leu Ala Gln Phe Leu Gly Met Gln
            100                 105                 110

Gly Thr Thr Lys Gln Leu Lys Asn Lys Lys Ala Val Val Ile Ile Ser
        115                 120                 125

Pro Gln Trp Phe Thr Lys Lys Gly Gln Asp Pro Asn Ala Phe Ala Leu
    130                 135                 140

Tyr Tyr Ser Pro Leu Gln Ala Cys Asn Phe Leu Leu Ser Ala Lys Asn
145                 150                 155                 160
```

Asn Lys Thr Asp Arg Tyr Ala Ala Lys Arg Leu Leu Asp Met Pro Asp
            165                 170                 175

Val Lys Gly Glu Ile Arg Asn Ser Leu Lys Gln Ile Ala Ala Gly Lys
        180                 185                 190

Lys Leu Thr Thr Phe Glu Arg Phe Tyr Leu Glu Asn Arg Arg Met
        195                 200                 205

Leu Arg Asn Glu Asp Asn Phe Phe Ser Ser Phe Gln Leu Arg Asp Arg
    210                 215                 220

Val Asn Lys Ile Gln Asn Arg Ala Lys Val Leu Pro Asn Thr Tyr Ser
225                 230                 235                 240

Val Ala Ala Leu Asn Lys Val Ala Glu Glu Gln Ala Ala His Thr
                245                 250                 255

Thr Ser Asn Asn Leu Gly Ile Asp Asn Thr Phe Tyr Arg Thr Arg Leu
            260                 265                 270

Pro Arg Lys Val Leu Lys Arg Leu Lys Gly Ser Gln Arg His Phe Asp
        275                 280                 285

Tyr Val Arg Ser Val Glu Tyr Gly Asp Phe Gln Leu Met Leu Glu Gln
    290                 295                 300

Phe Ala Lys Gln His Thr Asn Val Leu Phe Ile Ile Pro Pro Ile Asn
305                 310                 315                 320

Gly Lys Trp Met Lys Tyr Thr Gly Leu Ser Gln Lys Met Tyr Gln Glu
                325                 330                 335

Ser Val Ala Lys Ile Glu Gln Gln Leu Thr Ser Gln Gly Phe Glu Asn
            340                 345                 350

Ile Ala Asp Leu Ser Lys Arg Gly Asn Glu Lys Tyr Phe Met Gln Asp
        355                 360                 365

Thr Ile His Leu Gly Trp Lys Gly Trp Val Ala Val Asp Gln Ala Val
    370                 375                 380

Arg Pro Phe Met Lys Leu Pro Asn Glu Arg Tyr Asn Tyr Asp Met Ser
385                 390                 395                 400

Asn Tyr Tyr Phe Ser Lys Lys Trp Gln Asn Lys Asp Asn Val Lys Arg
                405                 410                 415

Val Asn Leu Asn Asn Lys Asp Arg Leu Lys Val Lys
            420                 425

<210> SEQ ID NO 17
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(26)
<223> OTHER INFORMATION: TLR1 Forward Prilmer

<400> SEQUENCE: 17
ttaatgagtg tttgtgaatg cagttg                                    26

<210> SEQ ID NO 18
<211> LENGTH: 22
<212> TYPE: DNA
<213> ORGANISM: Artificial Sequence

```
<220> FEATURE:
<223> OTHER INFORMATION: Primer
<220> FEATURE:
<221> NAME/KEY: misc_feature
<222> LOCATION: (1)...(22)
<223> OTHER INFORMATION: TLR1 Reverse Primer

<400> SEQUENCE: 18
gagcattgcc acatgggtat ag                                              22

<210> SEQ ID NO 19
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(23)
<223> OTHER INFORMATION: TLR2 Forward Primer

<400> SEQUENCE: 19
caaagcgtca aatctcagag gat                                             23

<210> SEQ ID NO 20
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(21)
<223> OTHER INFORMATION: TLR2 Reverse Primer

<400> SEQUENCE: 20
acaccccaga agcatcacat g                                               21

<210> SEQ ID NO 21
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(19)
<223> OTHER INFORMATION: Control Forward Primer

<400> SEQUENCE: 21
gtcgtggatc tgacgtgcc                                                  19

<210> SEQ ID NO 22
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(19)
<223> OTHER INFORMATION: Control Reverse Primer

<400> SEQUENCE: 22
tgcctgcttc accaccttc                                                  19
```